US008557525B1

(12) United States Patent
Wang et al.

(10) Patent No.: US 8,557,525 B1
(45) Date of Patent: Oct. 15, 2013

(54) COMPOSITE METASTASIS SCORE WITH WEIGHTED COEFFICIENTS FOR PREDICTING BREAST CANCER METASTASIS, AND USES THEREOF

(75) Inventors: Alice Wang, Lafayette, CA (US); Robert J. Lagier, San Leandro, CA (US); Charles M. Rowland, San Francisco, CA (US)

(73) Assignee: Celera Corporation, Alameda, CA (US)

( * ) Notice: Subject to any disclaimer, the term of this patent is extended or adjusted under 35 U.S.C. 154(b) by 0 days.

(21) Appl. No.: 13/406,221

(22) Filed: Feb. 27, 2012

Related U.S. Application Data

(60) Provisional application No. 61/446,763, filed on Feb. 25, 2011.

(51) Int. Cl.
*C12Q 1/68* (2006.01)
(52) U.S. Cl.
USPC ........ 435/6.14; 435/91.2; 435/194; 536/24.3; 536/24.33
(58) Field of Classification Search
None
See application file for complete search history.

(56) References Cited

U.S. PATENT DOCUMENTS

| 7,695,915 | B2 | 4/2010 | Lau et al. |
| 2009/0203015 | A1 | 8/2009 | Chang et al. |

OTHER PUBLICATIONS

Wang, A., et al., "Correlations of Component and Composite Metastasis Scores for Early Stage Breast Cancer", abstract and poster presented at the Miami Breast Cancer Symposium, Mar. 4, 2010, 2 pages.

*Primary Examiner* — Jim Ketter
(74) *Attorney, Agent, or Firm* — Celera Corporation

(57) ABSTRACT

The present invention relates to a composite metastasis score ("cMS") based on expression of a 14-gene molecular signature (referred to as a metastasis score, or "MS") in combination with progesterone receptor (PR) expression that is useful for predicting breast cancer metastasis. In preferred embodiments, the cMS is determined by applying weighted coefficients to MS and PR. The present invention provides methods and reagents for detecting and profiling the expression levels of these genes, and methods of using the expression level information for predicting risk of breast cancer metastasis, among other embodiments.

26 Claims, 25 Drawing Sheets

Figure 2. ROC curve for predicting distant metastases in 5 years by MS(CV) in the training sample set from CPMC. AUC = 0.76 (0.65 – 0.87)

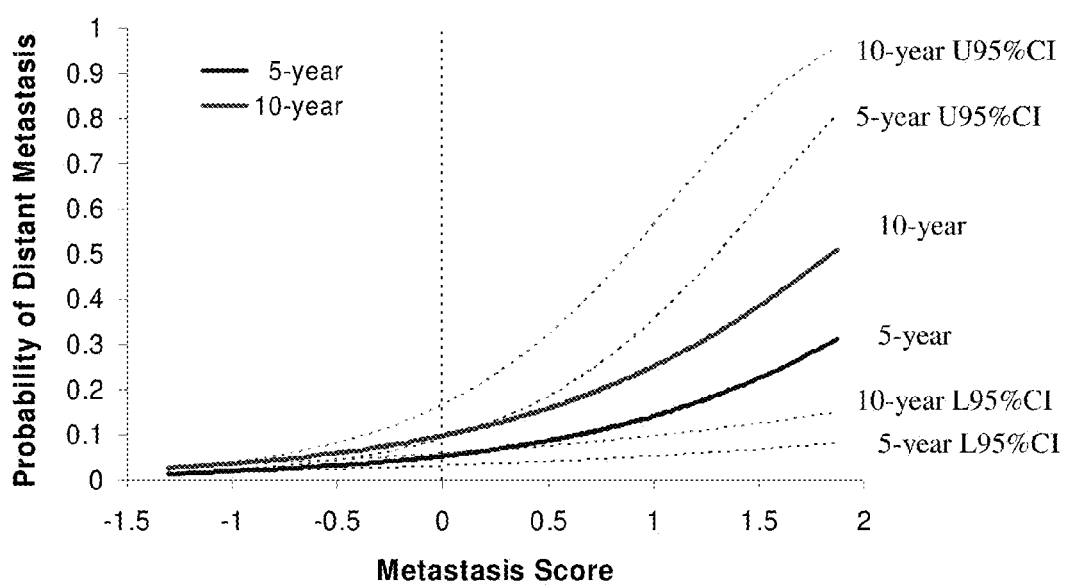
Figure 5. Probability of distant metastasis within 5 years and 10 years vs. Metastasis Score (MS) from 280 Guy's untreated patients Figure 6. Comparison of probability of distant metastasis in 10 years from 14-gene signature vs. 10-year relapse probability from Adjuvant! for untreated patients from Guy's Hospital
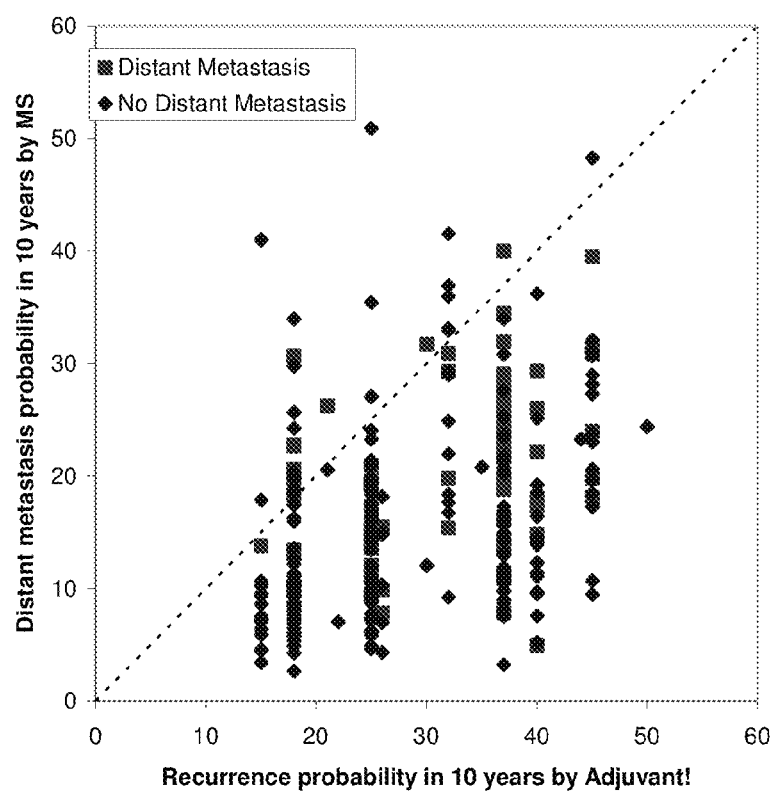

Figure 7. Kaplan-Meier curves for distant-metastasis-free survival in University of Muenster patients.
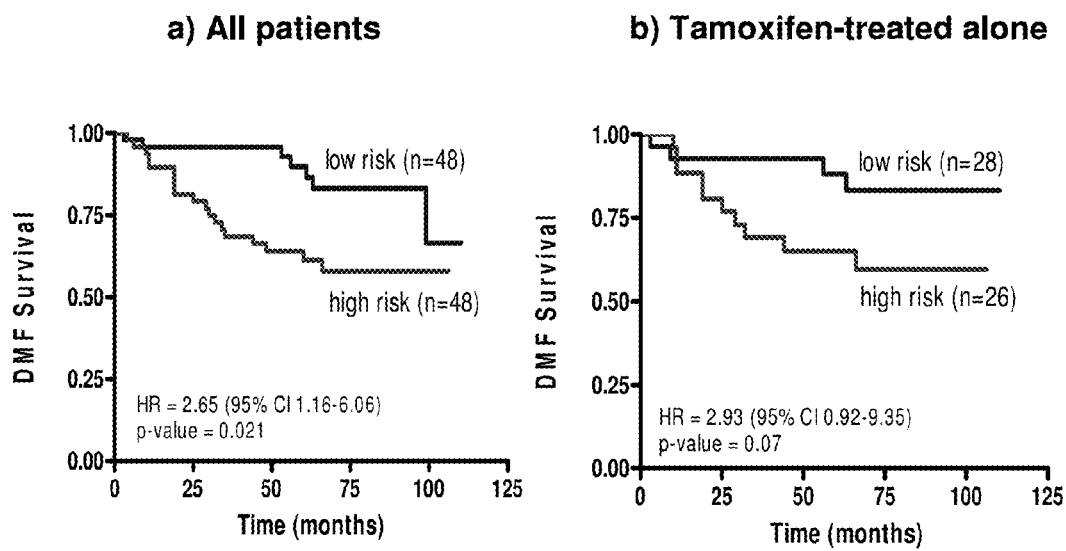

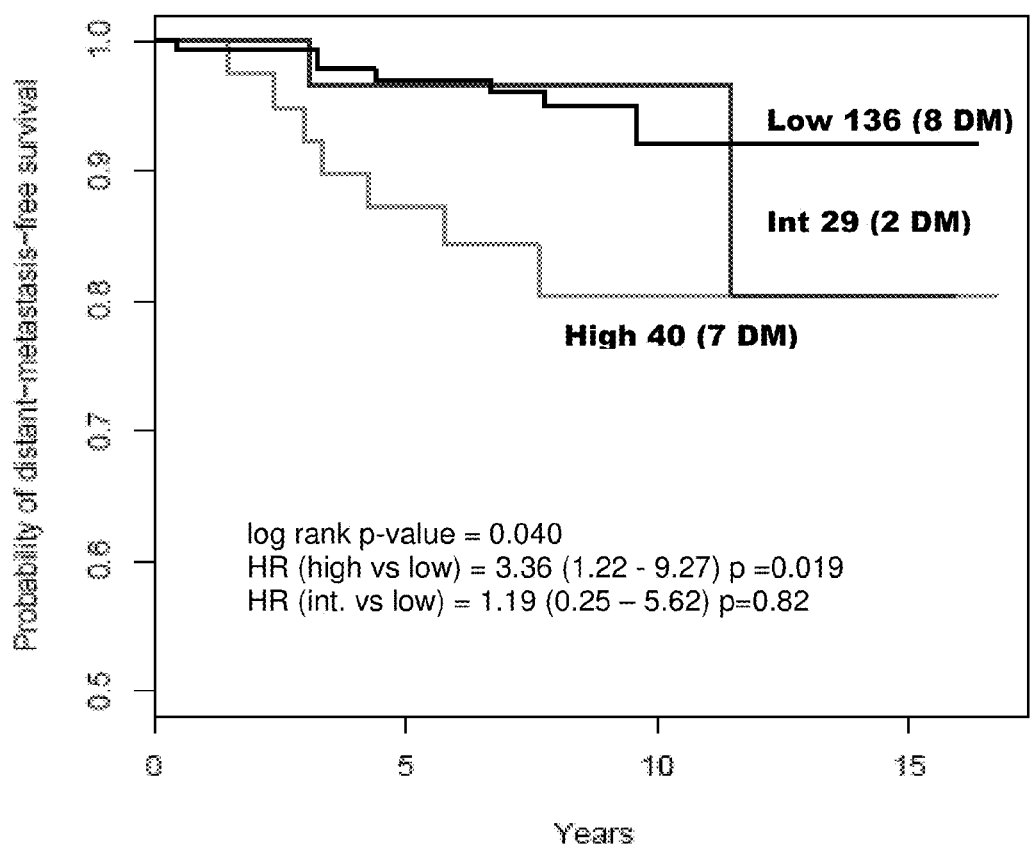
Figure 8. Kaplan-Meier curves of distant-metastasis-free survival in 3 MS groups (high, intermediate, low) for 205 treated patients from Guy's Hospital Figure 9. Kaplan-Meier curves of distant-metastasis-free survival in 2 risk groups (high and low) determined by MS for 205 treated patients from Guy's Hospital
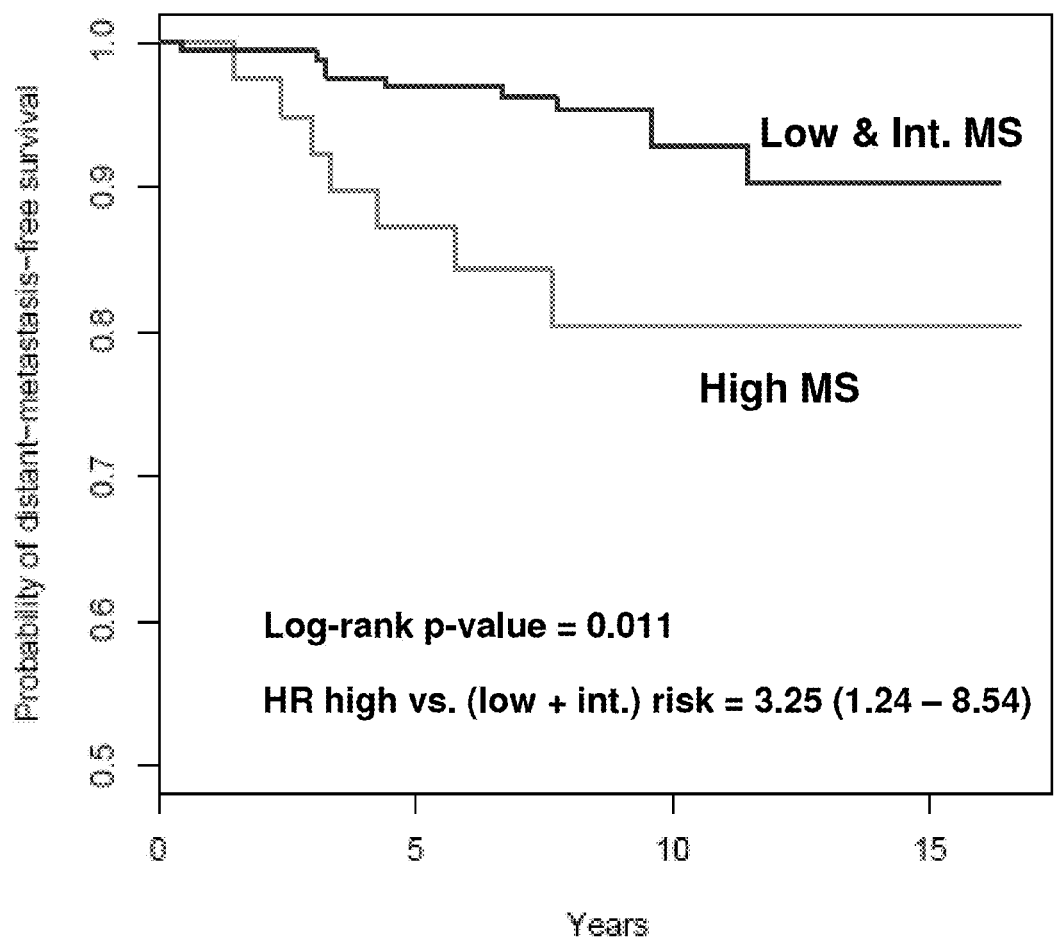

Figure 10. ROC curve of MS in Guy's treated samples, AUC = 0.7 (0.57 – 0.87)
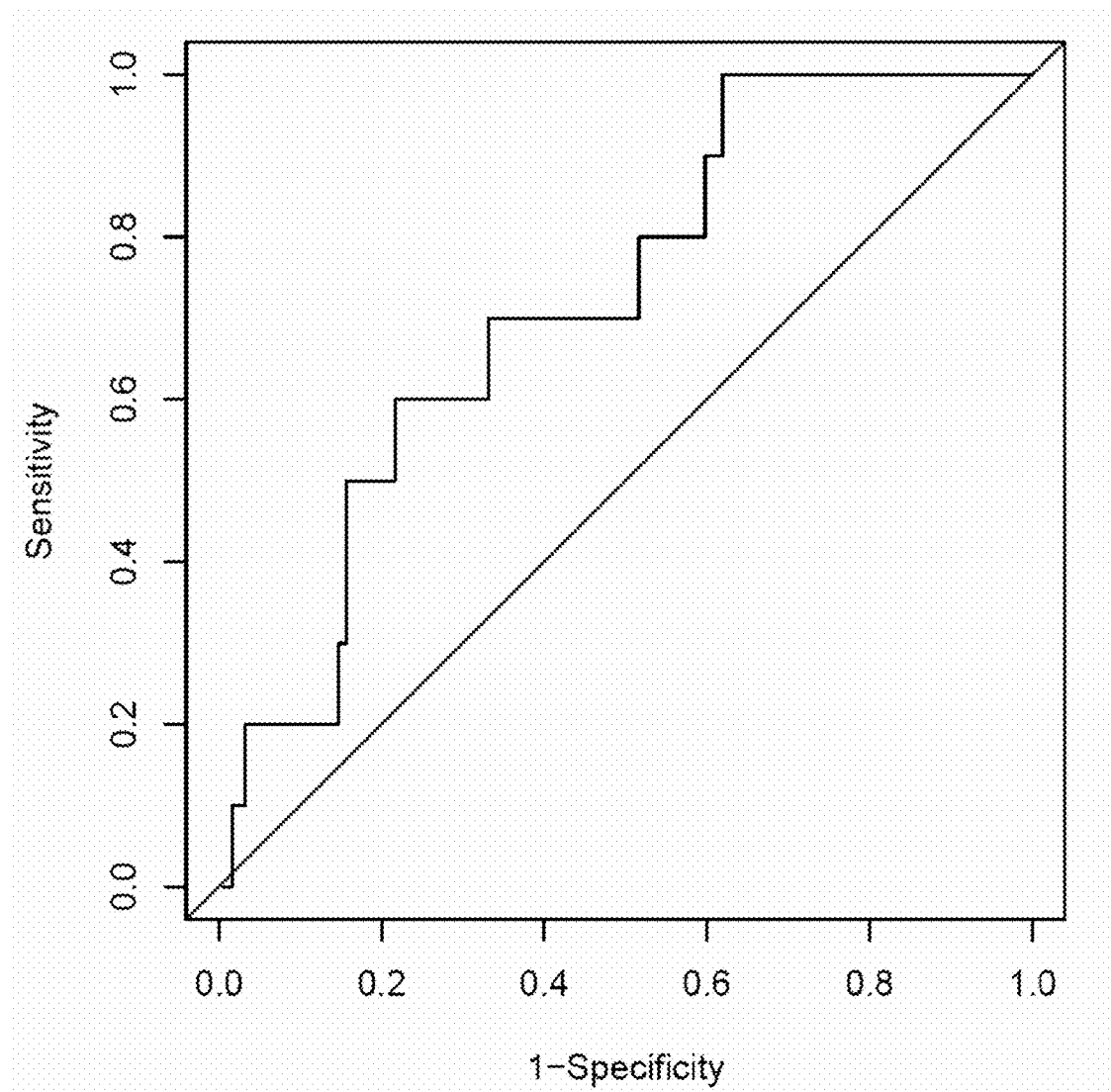

Figure 11. Time dependence of hazard ratios of high vs. low risk groups by MS in Guy's treated samples
(a)
(b)
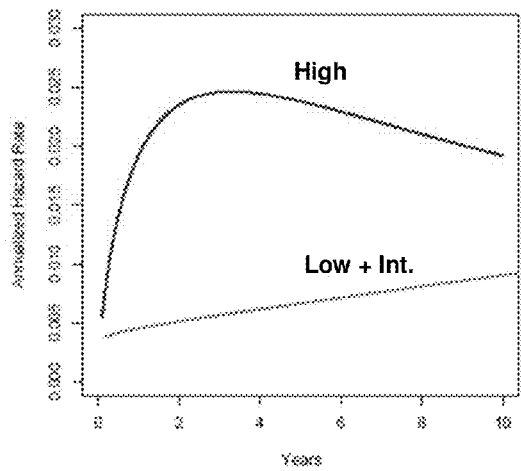
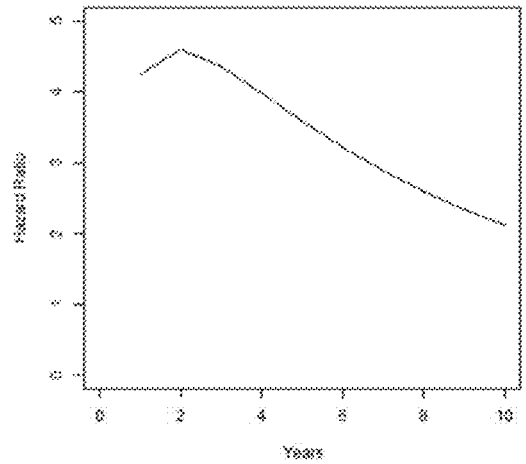

Figure 12. Kaplan-Meier curves of distant-metastasis-free survival (DMFS) for three MS groups (high, intermediate and low) in 234 Japanese samples
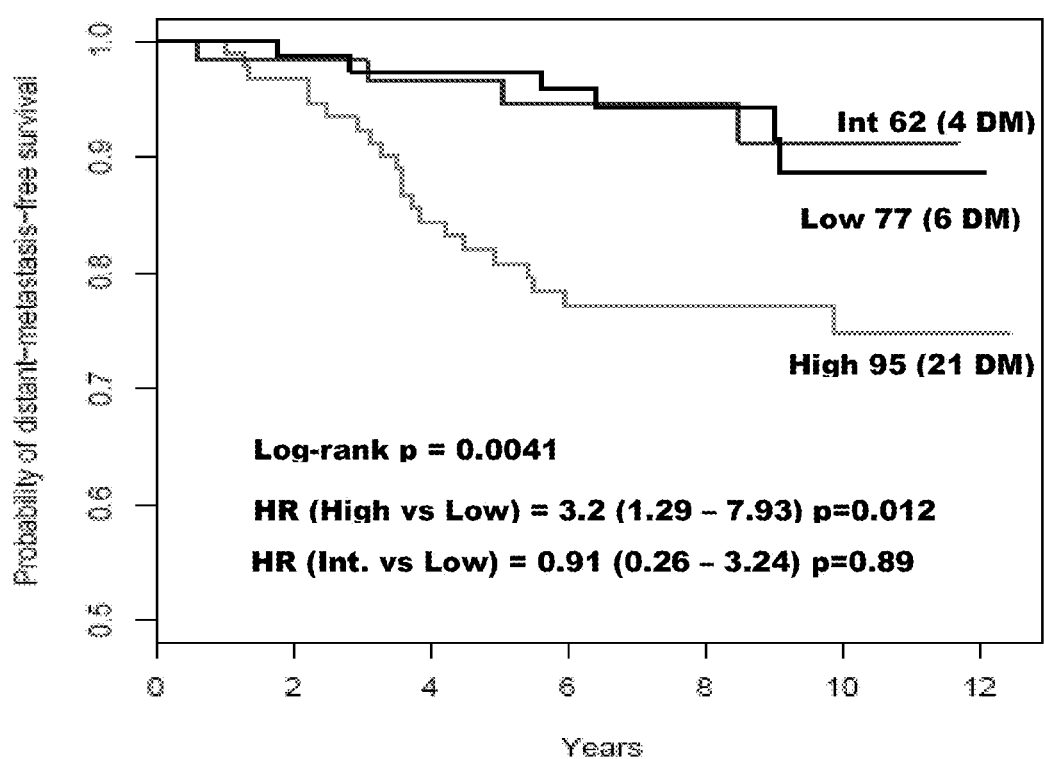

Figure 13. Kaplan-Meier curves of distant-metastasis-free survival (DMFS) for two risk groups (high MS and a combination of intermediate and low MS) in 234 Japanese samples
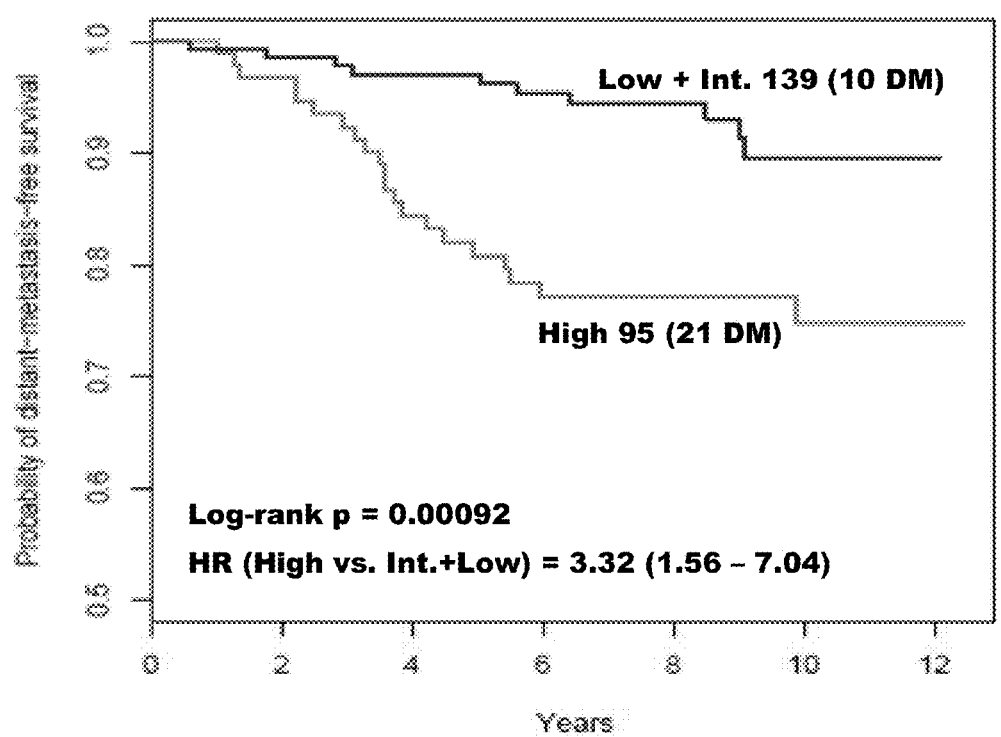

Figure 14. ROC curve of MS to predict distant metastasis in 5 years for Japanese patients. AUC = 0.73 (0.63 – 0.84)
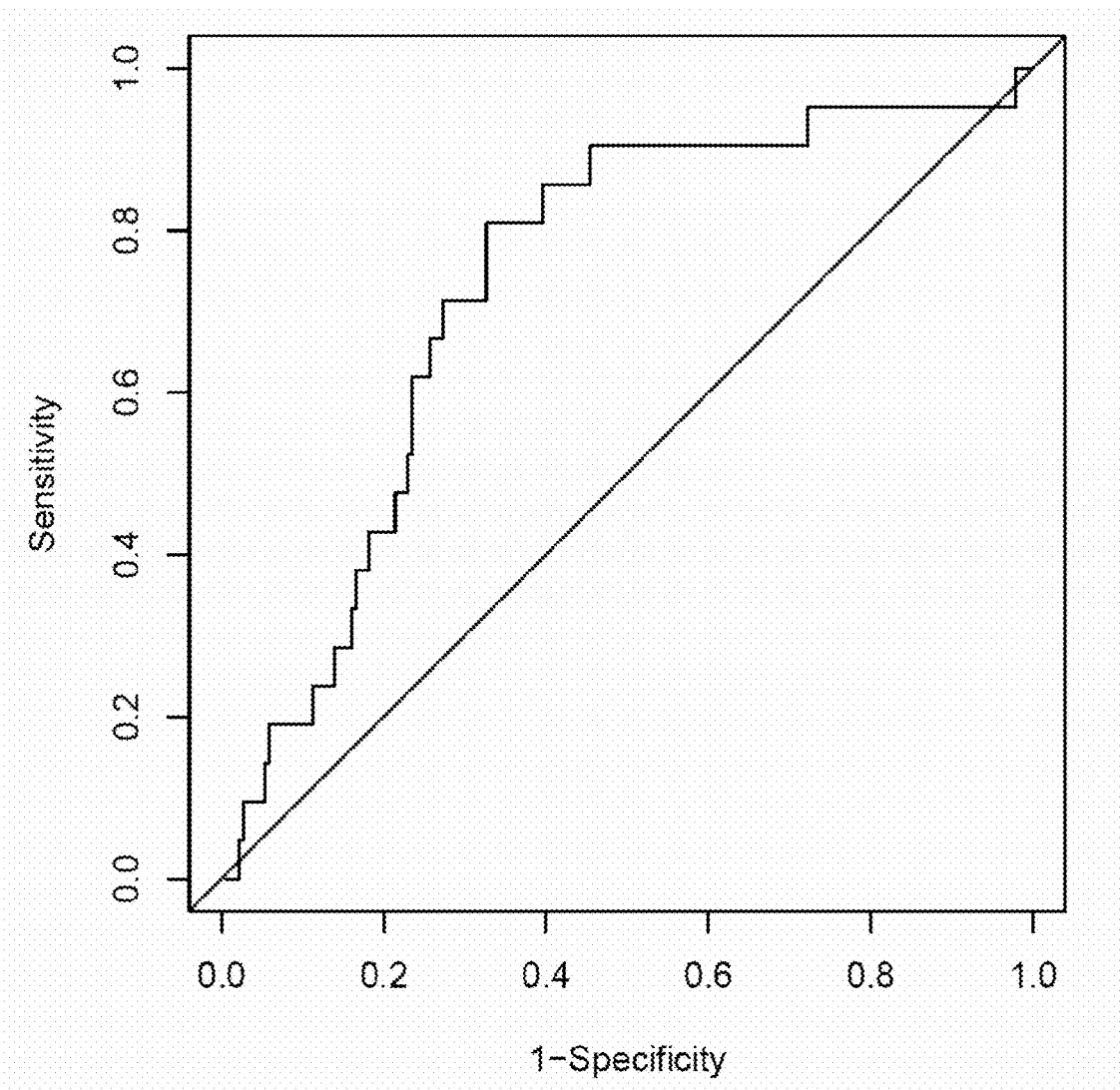

Figure 15. Annualized hazard rate for MS groups and hazard ratio of high vs. low risk groups as a function of time
(a) (b)
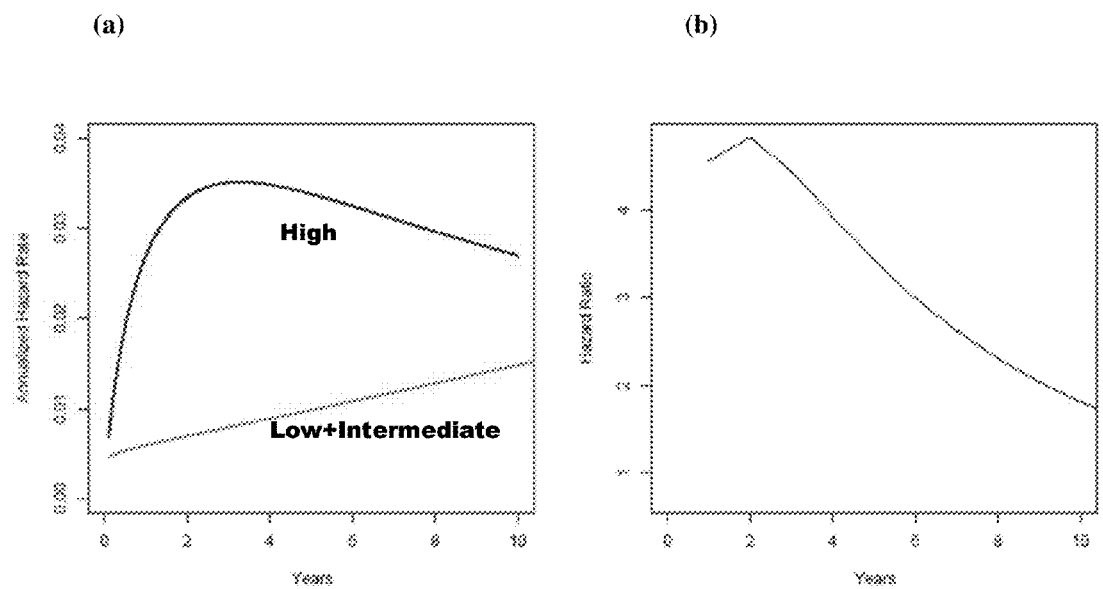

Figure 16. Composite metastasis score (cMS): Kaplan-Meier estimates of DMFS of a validation dataset by cMS
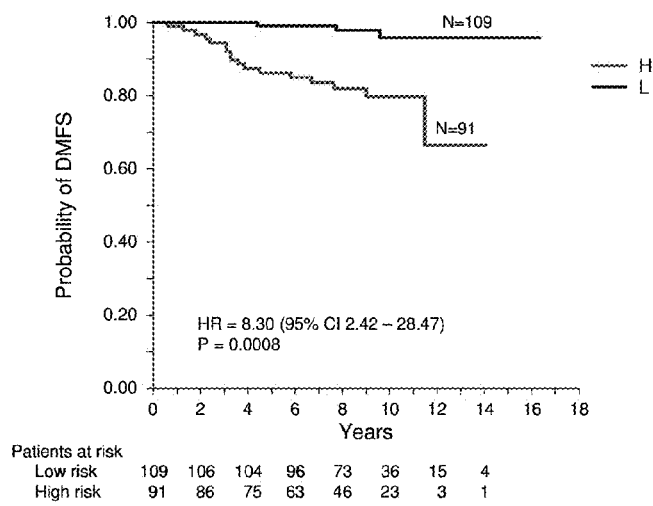
The Kaplan-Meier 9-year distant-metastasis-free survival (DMFS) estimates were 78.9% for the high risk group (the lower line, labeled "N=91") and 95.2% for the low risk group (the upper line, labeled "N= 109") by cMS.

SEQUENCE LISTING

<160> NUMBER OF SEQ ID NOS: 85

<210> SEQ ID NO 1
<211> LENGTH: 17
<212> TYPE: DNA
<213> ORGANISM: Homo sapiens

<400> SEQUENCE: 1
catggtggtg cctttcaa                                              17

<210> SEQ ID NO 2
<211> LENGTH: 23
<212> TYPE: DNA
<213> ORGANISM: Homo sapiens

<400> SEQUENCE: 2
gctgaataca tgtgagacga caa                                        23

<210> SEQ ID NO 3
<211> LENGTH: 22
<212> TYPE: DNA
<213> ORGANISM: Homo sapiens

<400> SEQUENCE: 3
gccaaatacc tgatggaact aa                                         22

<210> SEQ ID NO 4
<211> LENGTH: 20
<212> TYPE: DNA
<213> ORGANISM: Homo sapiens

<400> SEQUENCE: 4
ctcctgctgc aatttgagaa                                            20

<210> SEQ ID NO 5
<211> LENGTH: 16
<212> TYPE: DNA
<213> ORGANISM: Homo sapiens

<400> SEQUENCE: 5
cagtcggcgg agacaa                                                16

<210> SEQ ID NO 6
<211> LENGTH: 22
<212> TYPE: DNA
<213> ORGANISM: Homo sapiens

<400> SEQUENCE: 6
aagaggtgtg tgctcttctg aa                                         22

<210> SEQ ID NO 7
<211> LENGTH: 23
<212> TYPE: DNA
<213> ORGANISM: Homo sapiens

```
<400> SEQUENCE: 7
aaagtgacct gtgagagatt gaa                                            23

<210> SEQ ID NO 8
<211> LENGTH: 15
<212> TYPE: DNA
<213> ORGANISM: Homo sapiens

<400> SEQUENCE: 8
cgccctgccc aacaa                                                     15

<210> SEQ ID NO 9
<211> LENGTH: 18
<212> TYPE: DNA
<213> ORGANISM: Homo sapiens

<400> SEQUENCE: 9
ttatcccatc gccttgaa                                                  18

<210> SEQ ID NO 10
<211> LENGTH: 20
<212> TYPE: DNA
<213> ORGANISM: Homo sapiens

<400> SEQUENCE: 10
tgctccacac catgttgtaa                                                20

<210> SEQ ID NO 11
<211> LENGTH: 16
<212> TYPE: DNA
<213> ORGANISM: Homo sapiens

<400> SEQUENCE: 11
agagacgggc ccagaa                                                    16

<210> SEQ ID NO 12
<211> LENGTH: 24
<212> TYPE: DNA
<213> ORGANISM: Homo sapiens

<400> SEQUENCE: 12
caacagttga tctggattca ctaa                                           24

<210> SEQ ID NO 13
<211> LENGTH: 15
<212> TYPE: DNA
<213> ORGANISM: Homo sapiens

<400> SEQUENCE: 13
gcggagcccc atcaa                                                     15

<210> SEQ ID NO 14
<211> LENGTH: 21
<212> TYPE: DNA
<213> ORGANISM: Homo sapiens

<400> SEQUENCE: 14
catcctcatc cacaatgtca a                                              21

<210> SEQ ID NO 15
<211> LENGTH: 20
<212> TYPE: DNA
<213> ORGANISM: Homo sapiens
```

```
<400> SEQUENCE: 15
cacttctgct gcactgcttt                                              20

<210> SEQ ID NO 16
<211> LENGTH: 22
<212> TYPE: DNA
<213> ORGANISM: Homo sapiens

<400> SEQUENCE: 16
ggatgtggct accatttgt tt                                            22

<210> SEQ ID NO 17
<211> LENGTH: 18
<212> TYPE: DNA
<213> ORGANISM: Homo sapiens

<400> SEQUENCE: 17
ctacctgccc cctgagtt                                                18

<210> SEQ ID NO 18
<211> LENGTH: 21
<212> TYPE: DNA
<213> ORGANISM: Homo sapiens

<400> SEQUENCE: 18
agcatcatga caaggacaga a                                            21

<210> SEQ ID NO 19
<211> LENGTH: 19
<212> TYPE: DNA
<213> ORGANISM: Homo sapiens

<400> SEQUENCE: 19
tgtccaagct gtggtcaaa                                               19

<210> SEQ ID NO 20
<211> LENGTH: 19
<212> TYPE: DNA
<213> ORGANISM: Homo sapiens

<400> SEQUENCE: 20
tctccagggg tgatcagaa                                               19

<210> SEQ ID NO 21
<211> LENGTH: 18
<212> TYPE: DNA
<213> ORGANISM: Homo sapiens

<400> SEQUENCE: 21
gactgcgaaa agctggaa                                                18

<210> SEQ ID NO 22
<211> LENGTH: 20
<212> TYPE: DNA
<213> ORGANISM: Homo sapiens

<400> SEQUENCE: 22
ttgctcctcg cttagttgaa                                              20

<210> SEQ ID NO 23
<211> LENGTH: 19
<212> TYPE: DNA
<213> ORGANISM: Homo sapiens
```

-continued

<400> SEQUENCE: 23
tttggcagca gctagagaa                                                    19

<210> SEQ ID NO 24
<211> LENGTH: 22
<212> TYPE: DNA
<213> ORGANISM: Homo sapiens

<400> SEQUENCE: 24
cacgttcatc agatgcattt aa                                                22

<210> SEQ ID NO 25
<211> LENGTH: 20
<212> TYPE: DNA
<213> ORGANISM: Homo sapiens

<400> SEQUENCE: 25
gatggtttcc acaggaacaa                                                   20

<210> SEQ ID NO 26
<211> LENGTH: 18
<212> TYPE: DNA
<213> ORGANISM: Homo sapiens

<400> SEQUENCE: 26
ggatccaagt cccagcaa                                                     18

<210> SEQ ID NO 27
<211> LENGTH: 18
<212> TYPE: DNA
<213> ORGANISM: Homo sapiens

<400> SEQUENCE: 27
cctgctgatc caccctaa                                                     18

<210> SEQ ID NO 28
<211> LENGTH: 23
<212> TYPE: DNA
<213> ORGANISM: Homo sapiens

<400> SEQUENCE: 28
gcatactcct cgtagttctc caa                                               23

<210> SEQ ID NO 29
<211> LENGTH: 20
<212> TYPE: DNA
<213> ORGANISM: Homo sapiens

<400> SEQUENCE: 29
cactggatcc caagagtgaa                                                   20

<210> SEQ ID NO 30
<211> LENGTH: 22
<212> TYPE: DNA
<213> ORGANISM: Homo sapiens

<400> SEQUENCE: 30
tgatcccact ccaagtctag aa                                                22

<210> SEQ ID NO 31
<211> LENGTH: 22
<212> TYPE: DNA
<213> ORGANISM: Homo sapiens

```
<400> SEQUENCE: 31
tggacaagta atctctggtc aa                                              22

<210> SEQ ID NO 32
<211> LENGTH: 19
<212> TYPE: DNA
<213> ORGANISM: Homo sapiens

<400> SEQUENCE: 32
gtatccgtac ctccgcaaa                                                  19

<210> SEQ ID NO 33
<211> LENGTH: 18
<212> TYPE: DNA
<213> ORGANISM: Homo sapiens

<400> SEQUENCE: 33
tgccaatgca ggaaagaa                                                   18

<210> SEQ ID NO 34
<211> LENGTH: 25
<212> TYPE: DNA
<213> ORGANISM: Homo sapiens

<400> SEQUENCE: 34
tggtatctcc tgtgtaccta acaaa                                           25

<210> SEQ ID NO 35
<211> LENGTH: 13037
<212> TYPE: DNA
<213> ORGANISM: Homo sapiens

<400> SEQUENCE: 35
agtccacagc tgtcactaat cggggtaagc cttgttgtat ttgtgcgtgt gggtggcatt     60
ctcaatgaga actagcttca cttgtcattt gagtgaaatc tacaacccga ggcggctagt    120
gctcccgcac tactgggatc tgagatcttc ggagatgact gtcgcccgca gtacggagcc    180
agcagaagtc cgacccttcc tgggaatggg ctgtaccgag aggtccgact agccccaggg    240
ttttagtgag gggcagtgg aactcagcga gggactgaga gcttcacagc atgcacgagt    300
ttgatgccag agaaaaagtc gggagataaa ggagccgcgt gtcactaaat tgccgtcgca    360
gccgcagcca ctcaagtgcc ggacttgtga gtactctgcg tctccagtcc tcggacagaa    420
gttggagaac tctcttggag aactccccga gttaggagac gagatctcct aacaattact    480 acttttctt gcgctcccca cttgccgctc gctgggacaa acgacagcca cagttccct    540 gacgacagga tggaggccaa gggcaggagc tgaccagcgc cgccctcccc cgcccccgac    600
ccaggaggtg gagatccctc cggtccagcc acattcaaca cccactttct cctccctctg    660
cccctatatt cccgaaaccc cctcctcctt ccctttccc tcctcctgga gacggggag     720 gagaaaaggg gagtccagtc gtcatgactg agctgaaggc aaagggtccc cgggctcccc    780
acgtggcggg cggcccgccc tccccgagg tcggatcccc actgctgtgt cgcccagccg    840
caggtccgtt cccgggagc cagacctcgg acaccttgcc tgaagtttcg gccataccta    900
tctccctgga cgggctactc ttccctcggc cctgccaggg acaggacccc tccgacgaaa    960
agacgcagga ccagcagtcg ctgtcggacg tggagggcgc atattccaga gctgaagcta   1020
caaggggtgc tggaggcagc agttctagtc ccccagaaaa ggacagcgga ctgctggaca   1080
gtgtcttgga cactctgttg gcgccctcag gtcccgggca gagccaaccc agccctcccg   1140
```

```
cctgcgaggt caccagctct tggtgcctgt ttggccccga acttcccgaa gatccaccgg   1200
ctgcccccgc cacccagcgg gtgttgtccc cgctcatgag ccggtccggg tgcaaggttg   1260
gagacagctc cgggacggca gctgcccata aagtgctgcc ccggggcctg tcaccagccc   1320
ggcagctgct gctcccggcc tctgagagcc ctcactggtc cggggcccca gtgaagccgt   1380
ctccgcaggc cgctgcggtg gaggttgagg aggaggatgg ctctgagtcc gaggagtctg   1440
cgggtccgct tctgaagggc aaacctcggg ctctgggtgg cgcggcggct ggaggaggag   1500
ccgcggctgt cccgccgggg gcggcagcag gaggcgtcgc cctggtcccc aaggaagatt   1560
cccgcttctc agcgcccagg gtcgccctgg tggagcagga cgcgccgatg gcgcccgggc   1620 gctcccccgct ggccaccacg gtgatggatt tcatccacgt gcctatcctg cctctcaatc   1680
acgccttatt ggcagcccgc actcggcagc tgctggaaga cgaaagttac gacggcgggg   1740
ccggggctgc cagcgccttt gccccgccgc ggagttcacc ctgtgcctcg tccaccccgg   1800
tcgctgtagg cgacttcccc gactgcgcgt acccgcccga cgccgagccc aaggacgacg   1860
cgtaccctct ctatagcgac ttccagccgc ccgctctaaa gataaaggag gaggaggaag   1920
gcgcggaggc ctccgcgcgc tccccgcgtt cctaccttgt ggccggtgcc aacccgcag   1980 ccttcccgga tttcccgttg gggccaccgc ccccgctgcc gccgcgagcg accccatcca   2040
gacccgggga agcggcggtg acggccgcac ccgccagtgc ctcagtctcg tctgcgtcct   2100
cctcggggtc gaccctggag tgcatcctgt acaaagcgga gggcgcgccg cccagcagg   2160 gcccgttcgc gccgccgccc tgcaaggcgc cgggcgcgag cggctgcctg ctcccgcggg   2220
acggcctgcc ctccacctcc gcctctgccg ccgccgccgg gcggccccc gcgctctacc   2280 ctgcactcgg cctcaacggg ctcccgcagc tcggctacca ggccgccgtg ctcaaggagg   2340
gcctgccgca ggtctacccg ccctatctca actacctgag gccggattca gaagccagcc   2400
agagcccaca atacagcttc gagtcattac ctcagaagat ttgtttaatc tgtggggatg   2460
aagcatcagg ctgtcattat ggtgtcctta cctgtgggag ctgtaaggtc ttctttaaga   2520
gggcaatgga agggcagcac aactacttat gtgctgaag aaatgactgc atcgttgata   2580
aaatccgcag aaaaaactgc ccagcatgtc gccttagaaa gtgctgtcag gctggcatgg   2640
tccttggagg tcgaaaattt aaaaagttca ataaagtcag agttgtgaga gcactggatg   2700
ctgttgctct cccacagcca gtgggcgttc caaatgaaag ccaagccta agccagagat   2760 tcactttttc accaggtcaa gacatacagt tgattccacc actgatcaac ctgttaatga   2820
gcattgaacc agatgtgatc tatgcaggac atgacaacac aaaacctgac acctccagtt   2880
ctttgctgac aagtcttaat caactaggcg agaggcaact tctttcagta gtcaagtggt   2940
ctaaatcatt gccaggtttt cgaaacttac atattgatga ccagataact ctcattcagt   3000
attcttggat gagcttaatg gtgttttggtc taggatggag atcctacaaa cacgtcagtg   3060
ggcagatgct gtatttttgca cctgatctaa tactaaatga acagcggatg aaagaatcat   3120
cattctattc attatgcctt accatgtggc agatcccaca ggagtttgtc aagcttcaag   3180
ttagccaaga agagttcctc tgtatgaaag tattgttact tcttaataca attcctttgg   3240
aagggctacg aagtcaaacc cagtttgagg agatgaggtc aagctacatt agagagctca   3300
tcaaggcaat tggtttgagg caaaaggag ttgtgtcgag ctcacagcgt ttctatcaac   3360
ttacaaaact tcttgataac ttgcatgatc ttgtcaaaca acttcatctg tactgcttga   3420
atacatttat ccagtcccgg gcactgagtg ttgaatttcc agaaatgatg tctgaagtta   3480
ttgctgcaca attacccaag atattggcag ggatggtgaa accccttctc tttcataaaa   3540
```

```
agtgaatgtc atcttttcct tttaaagaat taaattttgt ggtatgtctt tttgttttgg    3600
tcaggattat gaggtcttga gttttttataa tgttcttctg aaagccttac atttataaca    3660
tcatagtgtg taaatttaaa agaaaaattg tgaggttcta attattttct tttataaagt    3720
ataattagaa tgtttaactg ttttgtttac ccatattttc ttgaagaatt tacaagattg    3780
aaaaagtact aaaattgtta aagtaaacta tcttatccat attatttcat accatgtagg    3840
tgaggatttt taacttttgc atctaacaaa tcatcgactt aagagaaaaa atcttacatg    3900
taataacaca aagctattat atgttatttc taggtaactc cctttgtgtc aattatattt    3960
ccaaaaatga acctttaaaa tggtatgcaa aattttgtct atatatattt gtgtgaggag    4020
gaaattcata actttcctca gattttcaaa agtatttta atgcaaaaaa tgtagaaaga    4080
gtttaaaacc actaaaatag attgatgttc ttcaaactag gcaaacaac tcatatgtta    4140
agaccatttt ccagattgga aacacaaatc tcttaggaag ttaataagta gattcatatc    4200
attatgcaaa tagtattgtg ggttttgtag gttttttaaaa taaccttttt tggggagaga    4260
attgtcctct aatgaggtat tgcgagtgga cataagaaat cagaagatta tggcctaact    4320
gtactcctta ccaactgtgg catgctgaaa gttagtcact cttactgatt ctcaattctc    4380
tcacctttga aagtagtaaa atatcttttcc tgccaattgc tcctttgggt cagagcttat    4440
taacatcttt tcaaatcaaa ggaaagaaga aagggagagg aggaggaggg aggtatcaat    4500
tcacatacct ttctcctctt tatcctccac tatcatgaat tcatattatg tttcagccat    4560
gcaaatcttt ttaccatgaa atttcttcca gaatttttccc cctttgacac aaattccatg    4620
catgtttcaa ccttcgagac tcagccaaat gtcatttctg taaaatcttc cctgagtctt    4680
ccaagcagta atttgccttc tcctagagtt tacctgccat tttgtgcaca tttgagttac    4740
agtagcatgt tattttacaa ttgtgactct cctgggagtc tgggagccat ataaagtggt    4800
caatagtgtt tgctgactga gagttgaatg acattttctc tctgtcttgg tattactgta    4860
gatttcgatc attctttggt tacatttctg catatttctg tacccatgac tttatcactt    4920
tcttctccca tgctttatct ccatcaatta tcttcattac ttttaaattt tccacctttg    4980
cttcctactt tgtgagatct ctcccttttac tgactataac atagaagaat agaagtgtat    5040
tttatgtgtc ttaaggacaa tactttagat tccttgttct aagttttttaa actgaatgaa    5100
tggaatatta tttctctccc taagcaaaat tccacaaaac aattatttct tatgtttatg    5160
tagccttaaa ttgttttgta ctgtaaacct cagcataaaa actttcttca tttctaattt    5220
cattcaacaa atattgattg aatacctggt attagcacaa gaaaaatgtg ctaataagcc    5280
ttatgagaat ttggagctga agaaagacat ataactcagg aaagttacag tccagtagta    5340
ggtataaatt acagtgcctg ataaataggc attttaatat ttgtacactc aacgtatact    5400
aggtaggtgc aaaacattta catataattt tactgatacc catgcagcac aaaggtacta    5460
actttaaata ttaaataaca cctttatgtg tcagtaattc atttgcatta aatcttattg    5520
aaaaggcttt caatatattt tccccacaaa tgtcatccca agaaaaaagt atttttaaca    5580
tctcccaaat ataatagtta caggaaatct acctctgtga gagtgacacc tctcagaatg    5640
aactgtgtga cacaagaaaa tgaatgtagg tctatccaaa aaaaccccca agaaacaaaa    5700
acaatattat tagcccttta tgcttaagtg atggactcag ggaacagttg atgttgtgat    5760
cattttatta tctgattctt gttactttga attaaaccaa tattttgatg atataaatca    5820
tttccaccag catatattta atttccataa taacttaaaa attttctaat ttcactcaac    5880
tatgagggaa tagaatgtgg tggccacagg tttggctttt gttaaaatgt ttgatatctt    5940
```

```
cgatgttgat ctctgtctgc aatgtagatg tctaaacact aggatttaat atttaaggct   6000
aagctttaaa aataaagtac cttttaaaa agaatatggc ttcaccaaat ggaaaatacc    6060
taatttctaa atcttttct ctacaaagtc ctatctacta atgtctccat tactatttag    6120
tcatcataac cattatcttc attttacatg tcgtgttctt tctggtagct ctaaaatgac   6180
actaaatcat aagaagacag gttacatatc aggaaatact tgaaggttac tgaaatagat   6240
tcttgagtta atgaaaatat tttctgtaaa aaggtttgaa aagccatttg agtctaaagc   6300
attatacctc cattatcagt agttatgtga caattgtgtg tgtgtttaat gtttaaagat   6360
gtggcacttt ttaataaggc aatgctatgc tattttttcc catttaacat taagataatt   6420
tattgctata cagatgatat ggaaatatga tgaacaatat ttttttgcc aaaactatgc    6480 cttgtaagta gccatggaat gtcaacctgt aacttaaatt atccacagat agtcatgtgt   6540
ttgatgatgg gcactgtgga gataactgac ataggactgt gcccccttc tctgccactt    6600 actagctgga tgagattaag caagtcattt aactgctctg attaaacctg cctttcccaa   6660
gtgctttgta atgaatagaa atggaaacca aaaaaaacgt atacaggcct tcagaaatag   6720
taattgctac tattttgttt tcattaagcc atagttctgg ctataatttt atcaaactca   6780
ccagctatat tctacagtga aagcaggatt ctagaaagtc tcactgtttt atttatgtca   6840
ccatgtgcta tgatatattt ggttgaattc atttgaaatt agggctggaa gtattcaagt   6900
aatttcttct gctgaaaaaa tacagtgttt tgagtttagg gcctgtttta tcaaagttct   6960
aaagagccta tcactcttcc attgtagaca tttaaaata atgacactga ttttaacatt    7020
tttaagtgtc tttttagaac agagagcctg actagaacac agcccctcca aaaacccatg   7080
ctcaaattat ttttactatg gcagcaattc cacaaaggg aacaatgggt ttagaaatta    7140
caatgaagtc atcaacccaa aaaacatccc tatccctaag aaggttatga tataaaatgc   7200
ccacaagaaa tctatgtctg ctttaatctg tcttttattg ctttggaagg atggctatta   7260 cattttagt ttttgctgtg aatacctgag cagtttctct catccatact tatccttcac    7320
acatcagaag tcaggataga atatgaatca ttttaaaaac ttttacaact ccagagccat   7380
gtgcataaga agcattcaaa acttgccaaa acatacattt tttttcaaat ttaaagatac   7440 tctattttg tattcaatag ctcaacaact gtggtcccca ctgataaagt gaagtggaca    7500
aggagacaag taatggcata agtttgtttt tcccaaagta tgcctgttca atagccattg   7560
gatgtgggaa atttctacat ctcttaaaat tttacagaaa atacatagcc agatagtcta   7620
gcaaaagttc accaagtcct aaattgctta tccttacttc actaagtcat gaaatcattt   7680
taatgaaaag aacatcacct aggttttgtg gtttcttttt ttcttattca tggctgagtg   7740
aaaacaacaa tctctgtttc tccctagcat ctgtggacta tttaatgtac cattattcca   7800
cactctatgg tccttactaa atacaaaatt gaacaaaaag cagtaaaaca actgactctt   7860
cacccatatt ataaaatata atccaagcca gattagtcaa catccataag atgaatccaa   7920
gctgaactgg gcctagatta ttgagttcag gttggatcac atccctattt attaataaac   7980
ttaggaaaga aggccttaca gaccatcagt tagctggagc taatagaacc tacacttcta   8040
aagttcggcc tagaatcaat gtggccttaa aagctgaaaa gaagcaggaa agaacagttt   8100
tcttcaataa tttgtccacc ctgtcactgg agaaaattta agaatttggg ggtgttggta   8160
gtaagttaaa cacagcagct gttcatggca gaaattattc aatacatacc ttctctgaat   8220
atcctataac caaagcaaag aaaaacacca agggggtttgt tctcctcctt ggagttgacc   8280
tcattccaag gcagagctca ggtcacaggc acaggggctg cgcccaagct tgtccgcagc   8340
```

```
cttatgcagc tgtggagtct ggaagactgt tgcaggactg ctggcctagt cccagaatgt    8400
cagcctcatt ttcgatttac tggctcttgt tgctgtatgt catgctgacc ttattgttaa    8460
acacaggttt gtttgctttt tttccactca tggagacatg ggagaggcat tatttttaag    8520
ctggttgaaa gctttaaccg ataaagcatt tttagagaaa tgtgaatcag gcagctaaga    8580
aagcatactc tgtccattac ggtaaagaaa atgcacagat tattaactct gcagtgtggc    8640
attagtgtcc tggtcaatat tcggatagat atgaataaaa tatttaaatg gtattgtaaa    8700
tagttttcag gacatatgct atagcttatt tttattatct tttgaaattg ctcttaatac    8760
atcaaatcct gatgtattca atttatcaga tataaattat tctaaatgaa gcccagttaa    8820 atgttttgt cttgtcagtt atatgttaag tttctgatct cttgtctat gacgtttact    8880 aatctgcatt tttactgtta tgaattattt tagacagcag tggtttcaag cttttgcca    8940 ctaaaatac cttttatttt ctcctccccc agaaagtct ataccttgaa gtatctatcc    9000
accaaactgt acttctatta agaaatagtt attgtgtttt cttaatgttt tgttattcaa    9060
agacatatca atgaaagctg ctgagcagca tgaataacaa ttatatccac acagatttga    9120
tatattttgt gcagccttaa cttgatagta taaaatgtca ttgcttttta aataatagtt    9180
agtcaatgga cttctatcat agctttccta aactaggtta agatccagag ctttggggtc    9240
ataatatatt acatacaatt aagttatctt tttctaaggg ctttaaaatt catgagaata    9300
accaaaaaag gtatgtggag agttaataca aacataccat attcttgttg aaacagagat    9360
gtggctctgc ttgttctcca taaggtagaa atactttcca gaatttgcct aaactagtaa    9420
gccctgaatt tgctatgatt agggatagga agagattttc acatggcaga ctttagaatt    9480
cttcacttta gccagtaaag tatctccttt tgatcttagt attctgtgta ttttaacttt    9540
tctgagttgt gcatgtttat aagaaaaatc agcacaaagg gtttaagtta aagccttttt    9600
actgaaattt gaaagaaaca gaagaaaata tcaaagttct ttgtattttg agaggattaa    9660
atatgattta caaaagttac atggagggct ctctaaaaca ttaaattaat tatttttgt    9720 tgaaaagtct tactttaggc atcattttat tcctcagcaa ctagctgtga agcctttact    9780
gtgctgtatg ccagtcactc tgctagattg tggagattac cagtgttccc gtcttctccg    9840
agcttagagt tggatgggga ataaagacag gtaaacagat agctacaata ttgtactgtg    9900
aatgcttatg ctggaggaag tacagggaac tattggagca cctaagagga gcacctacct    9960
tgaatttagg ggttagcaga ggcatcctga aaaaagtcaa agctaagcca caatctataa   10020
gcagtttagg aattagcaga acgtgcgtgg tgaggagatg ccaaaggcaa gaagagaaga   10080
gtattccaaa caggagggat tccaaagaga gaagagtatc ccaaacaaca tttgcacaaa   10140
cctgatgggg agagagaatg tggggtgggg atggatgatg agactgaaga agaaagccag   10200
gtctagataa tcagtggcct tgtacaccat gttaaagagt gtagacttga ttctgttgta   10260
aacaggaaag cagcacaatt catatgaata ttttagaaga ctcccactgg aatatggaga   10320
ataaagttgg agatgactaa tcctggaagc agggagaaca ttttttgagga agttgcacta   10380 ttttggtgaa aatgatgatc ataaacatga agaattgtag gtgatcatga cctcctctct   10440
aattttccag aagggttttg gaagatataa cataggaaca ttgacaggac tgacgaaagg   10500
agatgaaata caccatataa aattgtcaaac acaaggccag atgtctaatt attttgctta   10560
tgtgttgaaa ttacaaattt ttcatcagga aaccaaaaac tacaaaactt agttttccca   10620
agtcccagaa ttctatctgt ccaaacaatc tgtaccactc cacctatatc cctacctttg   10680
catgtctgtc caacctcaaa gtccaggtct atacacacgg gtaagactag agcagttcaa   10740
```

```
gtttcagaaa atgagaaaga ggaactgagt tgtgctgaac ccatacaaaa taaacacatt   10800
ctttgtatag attcttggaa cctcgagagg aattcaccta actcataggt atttgatggt   10860
atgaatccat ggctgggctc ggcttttaaa aagccttatc tgggattcct tctatggaac   10920
caagttccat caaagcccat ttaaaagcct acattaaaaa caaaattctt gctgcattgt   10980
atacaaataa tgatgtcatg atcaaataat cagatgccat tatcaagtgg aattacaaaa   11040
tggtataccc actccaaaaa aaaaaaaaaa gctaaattct cagtagaaca ttgtgacttc   11100
atgagccctc cacagccttg gagctgagga gggagcactg gtgagcagta ggttgaagag   11160
aaaacttggc gcttaataat ctatccatgt ttttcatct aaaagagcct tcttttgga    11220
ttaccttatt caatttccat caaggaaatt gttagttcca ctaaccagac agcagctggg   11280
aaggcagaag cttactgtat gtacatggta gctgtgggaa ggaggtttct ttctccaggt   11340
cctcactggc catacaccag tcccttgtta gttatgcctg gtcatagacc cccgttgcta   11400
tcatctcata tttaagtctt tggcttgtga atttatctat tctttcagct tcagcactgc   11460
agagtgctgg gactttgcta acttccattt cttgctggct tagcacattc ctcataggcc   11520
cagctctttt ctcatctggc cctgctgtgg agtcaccttg cccttcagg agagccatgg    11580
cttaccactg cctgctaagc ctccactcag ctgccaccac actaaatcca gcttctcta    11640
agatgttgca gactttacag gcaagcataa aaggcttgat cttcctggac ttccctttac   11700
ttgtctgaat ctcacctcct tcaactttca gtctcagaat gtaggcattt gtcctctttg   11760
ccctacatct tccttcttct gaatcatgaa agcctctcac ttcctcttgc tatgtgctgg   11820
aggcttctgt caggttttag aatgagttct catctagtcc tagtagcttt tgatgcttaa   11880
gtccacctt taaggatacc tttgagattt agaccatgtt tttcgcttga gaaagcccta   11940
atctccagac ttgcctttct gtggatttca aagaccaact gaggaagtca aagctgaat   12000
gttgactttc tttgaacatt tccgctataa caattccaat tctcctcaga gcaatatgcc   12060
tgcctccaac tgaccaggag aaaggtccag tgccaaagag aaaaacacaa agattaatta   12120
tttcagttga gcacatactt tcaaagtggt ttgggtattc atatgaggtt ttctgtcaag   12180
agggtgagac tcttcatcta tccatgtgtg cctgacagtt ctcctggcac tggctggtaa   12240
cagatgcaaa actgtaaaaa ttaagtgatc atgtatttta acgatatcat cacatactta   12300
ttttctatgt aatgttttaa atttccccta acatactttg actgttttgc acatggtaga   12360
tattcacatt ttttgtgtt gaagttgatg caatcttcaa agttatctac cccgttgctt    12420
attagtaaaa ctagtgttaa tacttggcaa gagatgcagg gaatctttct catgactcac   12480
gccctattta gttattaatg ctactaccct attttgagta agtagtaggt ccctaagtac   12540
attgtccaga gttatacttt taaagatatt tagccccata tacttcttga atctaaagtc   12600
atacaccttg ctcctcattt ctgagtggga aagacatttg agagtatgtt gacaattgtt   12660
ctgaaggttt ttgccaagaa ggtgaaactg tcctttcatc tgtgtatgcc tggggctggg   12720
tccctggcag tgatgggtg acaatgcaaa gctgtaaaaa ctaggtgcta gtgggcacct    12780
aatatcatca tcatatactt attttcaagc taatatgcaa aatcccatct ctgtttttaa   12840
actaagtgta gatttcagag aaaatatttt gtggttcaca taagaaaaca gtctactcag   12900
cttgacaagt gttttatgtt aaattggctg gtggtttgaa atgaatcatc ttcacataat   12960
gttttcttta aaaatattgt gaatttaact ctaattcttg ttattctgtg tgataataaa   13020
gaataaacta atttcta                                                  13037
```

-continued

```
<210> SEQ ID NO 36
<211> LENGTH: 2365
<212> TYPE: DNA
<213> ORGANISM: Homo sapiens

<400> SEQUENCE: 36
atgactgagc tgaaggcaaa gggtccccgg gctccccacg tggcgggcgg cccgccctcc      60
cccgaggtcg atccccact  gctgtgtcgc ccagccgcag gtccgttccc ggggagccag     120
acctcggaca ccttgcctga agtttcggcc atacctatct ccctggacgg gctactcttc     180
cctcggccct gccagggaca ggaccccctcc gacgaaaaga cgcaggacca gcagtcgctg    240
tcggacgtgg agggcgcata ttccagagct gaagctacaa ggggtgctgg aggcagcagt    300
tctagtcccc cagaaaagga cagcggactg ctggacagtg tcttggacac tctgttggcg    360
ccctcaggtc ccgggcagag ccaacccagc cctcccgcct gcgaggtcac cagctcttgg    420
tgcctgtttg gccccgaact ccccgaagat ccaccggctg cccccgccac ccagcgggtg    480
ttgtccccgc tcatgagccg gtccgggtgc aaggttggag acagctccgg gacggcagct    540
gcccataaag tgctgccccg gggcctgtca ccagcccggc agctgctgct cccggcctct    600
gagagccctc actggtccgg ggccccagtg aagccgtctc cgcaggccgc tgcggtggag    660
gttgaggagg aggatggctc tgagtccgag gagtctgcgg gtccgcttct gaagggcaaa    720
cctcgggctc tgggtggcgc ggcggctgga ggaggagccg cggctgtccc gccggggggcg   780 gcagcaggag gcgtcgccct ggtccccaag gaagattccc gcttctcagc gcccagggtc    840
gccctggtgg agcaggacgc gccgatggcg ccccgggcgct cccgctggc caccacggtg     900 atggatttca tccacgtgcc tatcctgcct ctcaatcacg ccttattggc agcccgcact    960
cggcagctgc tggaagacga aagttacgac ggcggggccg gggctgccag cgccttttgcc   1020 ccgccgcgga gttcaccctg tgcctcgtcc accccggtcg ctgtaggcga cttccccgac    1080
tgcgcgtacc cgcccgacgc cgagcccaag gacgacgcgt accctctcta tagcgacttc    1140
cagccgcccg ctctaaagat aaaggaggag gaggaaggcg cggaggcctc cgcgcgctcc    1200
ccgcgttcct accttgtggc cggtgccaac cccgcagcct tcccggattt cccgttgggg    1260
ccaccgcccc cgctgccgcc gcgagcgacc ccatccagac ccggggaagc ggcggtgacg    1320
gccgcacccg ccagtgcctc agtctcgtct gcgtcctcct cggggtcgac cctggagtgc    1380
atcctgtaca agcggagggg cgcgccgccc cagcagggcc cgttcgcgcc gccgccctgc    1440
aaggcgccgg gcgcgagcgg ctgcctgctc ccgcgggacg gcctgccctc cacctccgcc    1500
tctgccgccg ccgccggggc ggccccgcg  ctctaccctg cactcggcct caacgggctc    1560
ccgcagctcg gctaccaggc cgccgtgctc aaggagggcc tgccgcaggt ctacccgccc    1620
tatctcaact acctgaggcc ggattcagaa gccagccaga gcccacaata cagcttcgag    1680
tcattacctc agaagatttg tttaatctgt gggggatgaag catcaggctg tcattatggt    1740
gtccttacct gtgggagctg taaggtcttc tttaagaggg caatggaagg gcagcacaac    1800
tacttatgtg ctgaagaaaa tgactgcatc gttgataaaa tccgcagaaa aaactgccca    1860
gcatgtcgcc ttagaaaagtg ctgtcaggct ggcatggtcc ttggaggttt tcgaaactta    1920
catattgatg accagataac tctcattcag tattcttgga tgagcttaat ggtgtttggt    1980
ctaggatgga gatcctacaa acacgtcagt gggcagatgc tgtattttgc acctgatcta    2040
atactaaatg attcctttgg aagggctacg aagtcaaacc cagtttgagg agatgaggtc    2100
aagctacatt agagagctca tcaaggcaat tggtttgagg caaaaaggag ttgtgtcgag    2160
ctcacagcgt ttctatcaac ttacaaaact tcttgataac ttgcatgatc ttgtcaaaca    2220
```
acttcatctg tactgcttga atacatttat ccagtcccgg gcactgagtg ttgaatttcc    2280
agaaatgatg tctgaagtta ttgctgcaca attacccaag atattggcag ggatggtgaa    2340
accccttctc tttcataaaa agtga    2365

```
<210> SEQ ID NO 37
<211> LENGTH: 2392
<212> TYPE: DNA
<213> ORGANISM: Homo sapiens

<400> SEQUENCE: 37
```
atgactgagc tgaaggcaaa gggtccccgg gctccccacg tggcgggcgg cccgccctcc      60
cccgaggtcg atccccact gctgtgtcgc ccagccgcag gtccgttccc ggggagccag      120
acctcggaca ccttgcctga agtttcggcc atacctatct ccctggacgg gctactcttc      180
cctcggccct gccagggaca ggaccccctcc gacgaaaaga cgcaggacca gcagtcgctg    240
tcggacgtgg agggcgcata ttccagagct gaagctacaa ggggtgctgg aggcagcagt    300
tctagtcccc cagaaaagga cagcggactg ctggacagtg tcttggacac tctgttggcg    360
ccctcaggtc ccgggcagag ccaacccagc cctcccgcct gcgaggtcac cagctcttgg    420
tgcctgtttg gccccgaact tcccgaagat ccaccggctg ccccgccac ccagcgggtg      480 ttgtccccgc tcatgagccg gtccgggtgc aaggttggag acagtccgg gacggcagct     540 gcccataaag tgctgccccg gggcctgtca ccagcccggc agctgctgct cccggcctct    600
gagagccctc actggtccgg ggccccagtg aagccgtctc cgcaggccgc tgcggtggag    660
gttgaggagg aggatggctc tgagtccgag gagtctgcgg gtccgcttct gaagggcaaa    720
cctcgggctc tgggtggcgc ggcggctgga ggaggagccg cggctgtccc gccggggggcg    780 gcagcaggag gcgtcgccct ggtccccaag gaagattccc gcttctcagc gcccagggtc    840
gccctggtgg agcaggacgc gccgatggcg cccgggcgct ccccgctggc caccacggtg    900
atggatttca tccacgtgcc tatcctgcct ctcaatcacg ccttattggc agcccgcact    960
cggcagctgc tggaagacga aagttacgac ggcggggccg gggctgccag cgcctttgcc    1020
ccgccgcgga gttcaccctg tgcctcgtcc accccggtcg ctgtaggcga cttccccgac    1080
tgcgcgtacc cgcccgacgc cgagcccaag gacgacgcgt accctctcta tagcgacttc    1140
cagccgcccg ctctaaagat aaaggaggag gaggaaggcg cggaggcctc cgcgcgctcc    1200
ccgcgttcct accttgtggc cggtgccaac cccgcagcct tcccggattt cccgttgggg    1260
ccaccgcccc cgctgccgcc gcgagcgacc catccagac ccggggaagc ggcggtgacg     1320
gccgcacccg ccagtgcctc agtctcgtct gcgtcctcct cggggtcgac cctggagtgc    1380
atcctgtaca agcggagg gcgccgcc cagcagggcc cgttcgcgcc gccgccctgc        1440
aaggcgccgg gcgcgagcgg ctgcctgctc ccgcgggacg gcctgccctc cacctccgcc    1500
tctgccgccg ccgccggggc ggcccccgcg ctctaccctg cactcggcct caacgggctc    1560
ccgcagctcg gctaccaggc cgccgtgctc aaggagggcc tgccgcaggt ctacccgccc    1620
tatctcaact acctgaggcc ggattcagaa gccagccaga gcccacaata cagcttcgag    1680
tcattacctc agaagatttg tttaatctgt ggggatgaag catcaggctg tcattatggt    1740
gtccttacct gtgggagctg taaggtcttc tttaagaggg caatgaagg gcagcacaac    1800 tacttatgtg ctggaagaaa tgactgcatc gttgataaaa tccgcagaaa aaactgccca    1860
gcatgtcgcc ttagaaagtg ctgtcaggct ggcatggtcc ttgaggtttt cgaaactta    1920 catattgatg accagataac tctcattcag tattcttgga tgagcttaat ggtgtttggt    1980

```
ctaggatgga gatcctacaa acacgtcagt gggcagatgc tgtattttgc acctgatcta   2040
atactaaatg agcagagtat tgttacttct aatacaatt cctttggaag ggctacgaag    2100
tcaaacccag tttgaggaga tgaggtcaag ctacattaga gagctcatca aggcaattgg   2160
tttgaggcaa aaaggagttg tgtcgagctc acagcgtttc tatcaactta caaaacttct   2220
tgataacttg catgatcttg tcaaacaact tcatctgtac tgcttgaata catttatcca   2280
gtcccgggca ctgagtgttg aatttccaga aatgatgtct gaagttattg ctgcacaatt   2340
acccaagata ttggcaggga tggtgaaacc ccttctcttt cataaaaagt ga           2392
```

<210> SEQ ID NO 38
<211> LENGTH: 2750
<212> TYPE: DNA
<213> ORGANISM: Homo sapiens

<400> SEQUENCE: 38

```
atgactgagc tgaaggcaaa gggtccccgg gctccccacg tggcgggcgg cccgccctcc    60
cccgaggtcg atccccact gctgtgtcgc ccagccgcag gtccgttccc ggggagccag    120
acctcggaca ccttgcctga gtttcggcc ataccctatct ccctggacgg gctactcttc   180
cctcggccct gccagggaca ggacccctcc gacgaaaaga cgcaggacca gcagtcgctg   240
tcggacgtgg agggcgcata ttccagagct gaagctacaa ggggtgctgg aggcagcagt   300
tctagtcccc cagaaaagga cagcggactg ctggacagtg tcttggacac tctgttggcg   360
ccctcaggtc ccgggcagag ccaacccagc cctcccgcct gcgaggtcac cagctcttgg   420
tgcctgtttg gccccgaact tcccgaagat ccaccggctg ccccgccac ccagcgggtg    480 ttgtccccgc tcatgagccg gtccgggtgc aaggttggag acagtccgg gacggcagct   540 gcccataaag tgctgccccg gggcctgtca ccagcccggc agctgctgct cccggcctct   600
gagagccctc actggtccgg ggcccagtg aagccgtctc gcaggccgc tgcggtggag    660 gttgaggagg aggatggctc tgagtccgag gagtctgcgg gtccgcttct gaagggcaaa   720
cctcgggctc tgggtggcgc ggcggctgga ggaggagccg cggctgtccc gccggggggcg   780 gcagcaggag gcgtcgccct ggtccccaag gaagattccc gcttctcagc gcccagggtc   840
gccctggtgg agcaggacgc gccgatggcg cccgggcgct ccccgctggc caccacggtg   900
atggatttca tccacgtgcc tatcctgcct ctcaatcacg ccttattggc agcccgcact   960
cggcagctgc tggaagacga aagttacgac ggcggggccg gggctgccag cgccttttgcc   1020 ccgccgcgga gttcaccctg tgcctcgtcc accccggtcg ctgtaggcga cttccccgac   1080
tgcgcgtacc cgcccgacgc cgagcccaag gacgacgcgt accctctcta tagcgacttc   1140
cagccgcccg ctctaaagat aaaggaggag gaggaaggcg cggaggcctc cgcgcgctcc   1200
ccgcgttcct accttgtggc cggtgccaac cccgcagcct tcccggattt cccgttgggg   1260
ccaccgcccc cgctgccgcc gcgagcgacc ccatccagac ccggggaagc ggcggtgacg   1320
gccgcacccg ccagtgcctc agtctcgtct gcgtcctcct cggggtcgac cctggagtgc   1380
atcctgtaca aagcggaggg cgcgccgccc cagcaggggc cgttcgcgcc gccgccctgc   1440
aaggcgccgg gcgcgagcgg ctgcctgctc ccgcgggacg gcctgccctc cacctccgcc   1500
tctgccgccg ccgccggggc ggcccccgcg ctctaccctg cactcggcct caacgggctc   1560
ccgcagctcg gctaccaggc cgccgtgctc aaggagggcc tgccgcaggt ctacccgccc   1620
tatctcaact acctgaggcc ggattcagaa gccagccaga gccacacaata cagcttcgag   1680 tcattacctc agaagatttg tttaatctgt ggggatgaag catcaggctg tcattatggt   1740
```

-continued

```
gtccttacct gtgggagctg taaggtcttc tttaagaggg caatggaagg gcagcacaac    1800
tacttatgtg ctggaagaaa tgactgcatc gttgataaaa tccgcagaaa aaactgccca    1860
gcatgtcgcc ttagaaagtg ctgtcaggct ggcatggtcc ttggaggtcg aaaatttaaa    1920
aagttcaata aagtcagagt tgtgagagca ctggatgctg ttgctctccc acagccagtg    1980
ggcgttccaa atgaaagcca agccctaagc cagagattca cttttcacc aggtcaagac     2040 atacagttga ttccaccact gatcaacctg ttaatgagca ttgaaccaga tgtgatctat    2100
gcaggacatg acaacacaaa acctgacacc tccagttctt tgctgacaag tcttaatcaa    2160
ctaggcgaga ggcaacttct ttcagtagtc aagtggtcta aatcattgcc aggttttcga    2220
aacttacata ttgatgacca gataactctc attcagtatt cttggatgag cttaatggtg    2280
tttggtctag gatggagatc ctacaaacac gtcagtgggc agatgctgta ttttgcacct   2340
gatctaatac taaatgaatc ccacaggagt ttgtcaagct tcaagttagc caagaagagt    2400
tcctctgtat gaaagtattg ttacttctta atacaattcc tttggaaggg ctacgaagtc    2460
aaacccagtt tgaggagatg aggtcaagct acattagaga gctcatcaag gcaattggtt    2520
tgaggcaaaa aggagttgtg tcgagctcac agcgtttcta tcaacttaca aaacttcttg    2580
ataacttgca tgatcttgtc aaacaacttc atctgtactg cttgaataca tttatccagt    2640
cccgggcact gagtgttgaa tttccagaaa tgatgtctga agttattgct gcacaattac    2700
ccaagatatt ggcagggatg gtgaaacccc ttctctttca taaaaagtga                2750
```

<210> SEQ ID NO 39
<211> LENGTH: 22
<212> TYPE: DNA
<213> ORGANISM: Homo sapiens

<400> SEQUENCE: 39

```
tcgagtcatt acctcagaag at                                                22
```

<210> SEQ ID NO 40
<211> LENGTH: 21
<212> TYPE: DNA
<213> ORGANISM: Homo sapiens

<400> SEQUENCE: 40

```
cccacaggta aggacaccat a                                                 21
```

<210> SEQ ID NO 41
<211> LENGTH: 19
<212> TYPE: DNA
<213> ORGANISM: Homo sapiens

<400> SEQUENCE: 41

```
tgacagcctg atgcttcat                                                    19
```

<210> SEQ ID NO 42
<211> LENGTH: 17
<212> TYPE: DNA
<213> ORGANISM: Homo sapiens

<400> SEQUENCE: 42

```
cctgccccct gagttca                                                      17
```

<210> SEQ ID NO 43
<211> LENGTH: 17
<212> TYPE: DNA
<213> ORGANISM: Homo sapiens -continued

<400> SEQUENCE: 43
cagcaaggtt ggtgcca                                                          17

<210> SEQ ID NO 44
<211> LENGTH: 27
<212> TYPE: DNA
<213> ORGANISM: Homo sapiens

<400> SEQUENCE: 44
ctggattcac taatctagtt gtagtca                                               27

<210> SEQ ID NO 45
<211> LENGTH: 19
<212> TYPE: DNA
<213> ORGANISM: Homo sapiens

<400> SEQUENCE: 45
gaaaagctgg aacgacaga                                                        19

<210> SEQ ID NO 46
<211> LENGTH: 20
<212> TYPE: DNA
<213> ORGANISM: Homo sapiens

<400> SEQUENCE: 46
gccagatgtg tcacacatga                                                       20

<210> SEQ ID NO 47
<211> LENGTH: 20
<212> TYPE: DNA
<213> ORGANISM: Homo sapiens

<400> SEQUENCE: 47
ttgagaagga ggaaagtgca                                                       20

<210> SEQ ID NO 48
<211> LENGTH: 18
<212> TYPE: DNA
<213> ORGANISM: Homo sapiens

<400> SEQUENCE: 48
cctaaccccg agtctgca                                                         18

<210> SEQ ID NO 49
<211> LENGTH: 21
<212> TYPE: DNA
<213> ORGANISM: Homo sapiens

<400> SEQUENCE: 49
cctcgtagtt ctccaagagc a                                                     21

<210> SEQ ID NO 50
<211> LENGTH: 25
<212> TYPE: DNA
<213> ORGANISM: Homo sapiens

<400> SEQUENCE: 50
gctaccattt tgtttttatc cactt                                                 25

<210> SEQ ID NO 51
<211> LENGTH: 15
<212> TYPE: DNA
<213> ORGANISM: Homo sapiens

```
<400> SEQUENCE: 51
acgcaggcag gcaca                                                    15

<210> SEQ ID NO 52
<211> LENGTH: 19
<212> TYPE: DNA
<213> ORGANISM: Homo sapiens

<400> SEQUENCE: 52
agaactcttt gggcctgaa                                                19

<210> SEQ ID NO 53
<211> LENGTH: 17
<212> TYPE: DNA
<213> ORGANISM: Homo sapiens

<400> SEQUENCE: 53
tggtgccttc aagggat                                                  17

<210> SEQ ID NO 54
<211> LENGTH: 20
<212> TYPE: DNA
<213> ORGANISM: Homo sapiens

<400> SEQUENCE: 54
cctgttttgg gcttttctct                                               20

<210> SEQ ID NO 55
<211> LENGTH: 23
<212> TYPE: DNA
<213> ORGANISM: Homo sapiens

<400> SEQUENCE: 55
ccatgttgta aacatcatat gct                                           23

<210> SEQ ID NO 56
<211> LENGTH: 21
<212> TYPE: DNA
<213> ORGANISM: Homo sapiens

<400> SEQUENCE: 56
gtgagagatt gaaccatgga g                                             21

<210> SEQ ID NO 57
<211> LENGTH: 19
<212> TYPE: DNA
<213> ORGANISM: Homo sapiens

<400> SEQUENCE: 57
tctgcaggga gaggagttt                                                19

<210> SEQ ID NO 58
<211> LENGTH: 28
<212> TYPE: DNA
<213> ORGANISM: Homo sapiens

<400> SEQUENCE: 58
gtgtacactc cagaattaag caaaataa                                      28

<210> SEQ ID NO 59
<211> LENGTH: 19
<212> TYPE: DNA
<213> ORGANISM: Homo sapiens
```

```
<400> SEQUENCE: 59
cgggcactga gtgttgaat                                              19

<210> SEQ ID NO 60
<211> LENGTH: 20
<212> TYPE: DNA
<213> ORGANISM: Homo sapiens

<400> SEQUENCE: 60
tgggtaattg tgcagcaata                                             20

<210> SEQ ID NO 61
<211> LENGTH: 19
<212> TYPE: DNA
<213> ORGANISM: Homo sapiens

<400> SEQUENCE: 61
gctttgtggt catccagaa                                              19

<210> SEQ ID NO 62
<211> LENGTH: 19
<212> TYPE: DNA
<213> ORGANISM: Homo sapiens

<400> SEQUENCE: 62
ccagcagtga gcggtagaa                                              19

<210> SEQ ID NO 63
<211> LENGTH: 22
<212> TYPE: DNA
<213> ORGANISM: Homo sapiens

<400> SEQUENCE: 63
gcaaatttca catactgatg aa                                          22

<210> SEQ ID NO 64
<211> LENGTH: 21
<212> TYPE: DNA
<213> ORGANISM: Homo sapiens

<400> SEQUENCE: 64
catctgtttt ctggttttca a                                           21

<210> SEQ ID NO 65
<211> LENGTH: 25
<212> TYPE: DNA
<213> ORGANISM: Homo sapiens

<400> SEQUENCE: 65
tgtgtaccta acaaagttat ctcca                                       25

<210> SEQ ID NO 66
<211> LENGTH: 14
<212> TYPE: DNA
<213> ORGANISM: Homo sapiens

<400> SEQUENCE: 66
tccggaagtc tctg                                                   14

<210> SEQ ID NO 67
<211> LENGTH: 16
<212> TYPE: DNA
<213> ORGANISM: Homo sapiens
```

```
<400> SEQUENCE: 67
tctgtcttcc gagctg                                                    16

<210> SEQ ID NO 68
<211> LENGTH: 17
<212> TYPE: DNA
<213> ORGANISM: Homo sapiens

<400> SEQUENCE: 68
atcttggtga aagatgc                                                   17

<210> SEQ ID NO 69
<211> LENGTH: 19
<212> TYPE: DNA
<213> ORGANISM: Homo sapiens

<400> SEQUENCE: 69
ttatagtgaa gctttagtc                                                 19

<210> SEQ ID NO 70
<211> LENGTH: 17
<212> TYPE: DNA
<213> ORGANISM: Homo sapiens

<400> SEQUENCE: 70
agctgattcg agagatg                                                   17

<210> SEQ ID NO 71
<211> LENGTH: 20
<212> TYPE: DNA
<213> ORGANISM: Homo sapiens

<400> SEQUENCE: 71
ctatgttgga ctatgacatg                                                20

<210> SEQ ID NO 72
<211> LENGTH: 19
<212> TYPE: DNA
<213> ORGANISM: Homo sapiens

<400> SEQUENCE: 72
ctcaacgagg aggcgggcc                                                 19

<210> SEQ ID NO 73
<211> LENGTH: 20
<212> TYPE: DNA
<213> ORGANISM: Homo sapiens

<400> SEQUENCE: 73
tcagctttag aatcttgcat                                                20

<210> SEQ ID NO 74
<211> LENGTH: 22
<212> TYPE: DNA
<213> ORGANISM: Homo sapiens

<400> SEQUENCE: 74
agtttaccac tcatgtgaca tg                                             22

<210> SEQ ID NO 75
<211> LENGTH: 18
<212> TYPE: DNA
<213> ORGANISM: Homo sapiens
```

```
<400> SEQUENCE: 75
ttccgattaa gagttctt                                              18

<210> SEQ ID NO 76
<211> LENGTH: 25
<212> TYPE: DNA
<213> ORGANISM: Homo sapiens

<400> SEQUENCE: 76
gctttcggat ctcctttagc caacc                                      25

<210> SEQ ID NO 77
<211> LENGTH: 17
<212> TYPE: DNA
<213> ORGANISM: Homo sapiens

<400> SEQUENCE: 77
attcagtcca attcaag                                               17

<210> SEQ ID NO 78
<211> LENGTH: 20
<212> TYPE: DNA
<213> ORGANISM: Homo sapiens

<400> SEQUENCE: 78
atattagagc tgaacttgat                                            20

<210> SEQ ID NO 79
<211> LENGTH: 19
<212> TYPE: DNA
<213> ORGANISM: Homo sapiens

<400> SEQUENCE: 79
atactcagaa tccagggtt                                             19

<210> SEQ ID NO 80
<211> LENGTH: 15
<212> TYPE: DNA
<213> ORGANISM: Homo sapiens

<400> SEQUENCE: 80
tgtgcctcaa atcta                                                 15

<210> SEQ ID NO 81
<211> LENGTH: 20
<212> TYPE: DNA
<213> ORGANISM: Homo sapiens

<400> SEQUENCE: 81
cttcagacat catttctgga                                            20

<210> SEQ ID NO 82
<211> LENGTH: 24
<212> TYPE: DNA
<213> ORGANISM: Homo sapiens

<400> SEQUENCE: 82
ccagccagtc ccttggacag cacc                                       24

<210> SEQ ID NO 83
<211> LENGTH: 18
<212> TYPE: DNA
<213> ORGANISM: Homo sapiens
```

-continued

```
<400> SEQUENCE: 83
aatttcctga agctgagc                                                 18

<210> SEQ ID NO 84
<211> LENGTH: 16
<212> TYPE: DNA
<213> ORGANISM: Homo sapiens

<400> SEQUENCE: 84
tctctcttac aacttc                                                   16

<210> SEQ ID NO 85
<211> LENGTH: 18
<212> TYPE: DNA
<213> ORGANISM: Homo sapiens

<400> SEQUENCE: 85
cagatgaagt gagttatg                                                 18
```

COMPOSITE METASTASIS SCORE WITH WEIGHTED COEFFICIENTS FOR PREDICTING BREAST CANCER METASTASIS, AND USES THEREOF

FIELD OF THE INVENTION

The present invention relates to prognosis of breast cancer metastasis. In particular, the present invention relates to a multi-gene prognostic signature typically comprising 14 genes (which may be referred to herein as a "metastasis score" ("MS")) in combination with progesterone receptor (PR) that is useful for predicting risk of breast cancer metastasis. This combination of MS and PR may be referred to herein as a "composite metastasis score" ("cMS"). Furthermore, in preferred embodiments, the cMS is determined by applying weighted coefficients to MS and PR. For example, in certain exemplary embodiments for determining a cMS, a weighted coefficient of 0.0326 or 0.0338 (or similar value) is applied to MS, and a weighted coefficient of −0.2034 or −0.22026 (or −0.2203) (or similar value) is applied to PR. mRNA from a breast cancer patient's tumor sample can be obtained from formalin-fixed, paraffin-embedded (FFPE) tissue sections, and the expression levels of PR and the 14 genes of the MS can be measured by methods known in the art. Thus, the present invention is amenable for use in routine clinical laboratory testing for assessing the risk of metastasis, particularly distant metastasis of estrogen receptor (ER)-positive breast tumors, especially in tamoxifen-treated patients.

BACKGROUND OF THE INVENTION

Early detection of breast cancer improves the chances of successful treatment and recovery. Routine screening mammography has increased the detection of stage I breast cancers and correspondingly, many more women are being diagnosed with lymph node-negative tumors (B. Cady, 1997, *Surg Oncol Clin N Am* 6:195-202). About 43% of the approximately 240,000 women in the United States diagnosed with breast cancer each year are node-negative (no detectable tumor cells in lymph nodes).

Based on the current guidelines, 85-90% of node-negative patients are candidates for systemic adjuvant therapy after surgery. Such systemic adjuvant therapy may include chemotherapy and hormonal therapy. However, about 60-70% of women with node-negative breast cancer who receive local treatment (mastectomy or lumpectomy and radiation) will not experience distant recurrence. Treatment decisions for breast cancer patients benefit from the assessment of each patient's risk for metastasis and response to treatment using multiple clinical and histopathological parameters.

Several recent studies have used microarrays to demonstrate that a patient's gene expression profile can also provide useful prognostic information. A subset of these studies has received focused attention due to their size, and the extent of their validation. (L J van't Veer, H. Dai et al., 2002, *Nature* 415:530-536; M J van de Vijver, Y D He et al., 2002, *N Engl J Med* 347:1999-2009; Y. Wang, J G Klijn et al., 2005, *Lancet* 365:671-679; H. Dai, L J van't Veer et al., 2005, *Cancer Res* 15:4059-4066; and H Y Chang, D S Nuyten et al., 2005, *Proc Natl Acad Sci USA* 102:3738-3743).

The resulting confidence garnered for a 70-gene prognostic signature identified by van't Veer, Dai et al. (2002, *Nature* 415:530-536) has led to its incorporation into a European trial, the Microarray for Node-Negative Disease May Avoid Chemotherapy (MINDACT). Likewise, a PCR-based, 21-gene predictive signature described by S P Paik, S. Shak et al. (2004, *N Engl J Med* 351:2817-2826) has been included in a phase III trial by The Breast Cancer Intergroup of North America (Program for the Assessment of Clinical Cancer Tests (PACCT) (V G Kaklamani and W J Gradishar, 2006, *Curr Treat Options Oncol* 7:123-8).

The 21-gene predictive signature (including 5 normalization genes) by S P Paik (2004, *N Engl J Med* 351:2817-2826) was derived from Tamoxifen-treated patients. The independence of that signature has drawn concern due to its substantial overlap with genes and/or proteins already used in conventional immunohistochemistry (IHC) tests (D R Carrizosa and L A Carey, 2005, *The American Journal of Oncology Review* 4:7-10). Various hormonal therapy strategies for treating ER-positive breast cancer patients may include Tamoxifen alone, sequential use of Tamoxifen plus aromatase inhibitors, or aromatase inhibitors alone (E P Winer, C. Hudis et al., 2005, *J Clin Oncol* 23: 619-629; S M Swain, 2005, *N Engl J Med* 353:2807-9).

Thus, there is a need for a gene-based prognostic assay that can be used for routine clinical laboratory testing in predicting the risk of distant metastasis in breast cancer patients, particularly an assay that detects expression levels mRNA, which can be readily obtained from tumor tissues preserved by routine collection methods such as FFPE tumor sections. Information about the risk for distant metastasis can be used in guiding treatment strategies for breast cancer patients, particularly early stage lymph node-negative patients, such that patients who are at higher risk of distant metastasis are treated properly, and patients who are at lower risk of distant metastasis may be spared the side effects of certain treatments.

A 14-gene metastasis score, which is particularly useful for determining risk of distant metastasis in a breast cancer patient, is described in U.S. Pat. No. 7,695,915, issued Apr. 13, 2010 to Kit Lau et al., which is incorporated herein by reference in its entirety.

Progesterone Receptor (PR)

Progesterone receptor (PR) status, as well as estrogen receptor (ER) status, in breast cancer patients is a factor that is used for therapeutic decisions such as whether or not a patient may benefit from hormonal therapy (Henry and Hayes, *Oncologist* 2006, 11:541-552) (PGR is the gene name for PR, thus PR and PGR may be used herein interchangeably; ESR1 is the gene name for ER, thus ER and ESR1 may be used herein interchangeably). The American Society of Clinical Oncology (ASCO) recommends routine measurement of PR, as well as ER, to identify patients most likely to benefit from hormonal therapy (Harris et al., *J Clin Oncol* 2007, 25:5287-5312). As an example, studies have shown that patients with ER-positive/PR-negative breast tumors responded less well to hormonal therapy than those with ER-positive/PR-positive breast tumors (Kim et al., *Clin Cancer Res* 2006, 12: 1013s-1018s and Cui et al., *J. Clin Oncol* 2005; 23: 7721-7735). In Caucasians, approximately 60-65% of breast cancer cases are ER-positive and PR-positive (ER+/PR+), 15-20% are ER+/PR−, 15-20% are ER−/PR−, and less than 5% are ER−/PR+ (Anderson et al., *J Clin Oncol* 2001, 19:18-27). The estrogen receptor is the therapeutic target for tamoxifen, a selective estrogen receptor modulator (SERM) that is commonly used in the treatment of breast cancer. ER and PR status in malignant tissue from breast cancer patients provides classification of outcome and clinical benefit for adjuvant endocrine or chemoendocrine therapies such as tamoxifen and aromatase inhibitors. The response rate to tamoxifen treatment has been reported to be markedly decreased in patients with ER+/PR− breast tumors (Cui et al.,

*J Clin Oncol* 2005, 23:7721-7735; Arpino et al., *J Natl Cancer Inst* 2005, 97:1254-1261; and Rakha et al., *J Clin Oncol* 2007, 25:4772-4778).

In accordance with conventional terminology, PR (as well as ER) "status" refers to the relative expression level of this gene in a breast tumor sample as compared with the normal range of expression levels of this gene in healthy (i.e., non-cancerous) breast samples. The term "positive" with respect to PR (as well as ER) status indicates that the gene is over-expressed in a breast tumor. In contrast, "negative" indicates that the gene is not over-expressed in a breast tumor.

The status of PR (as well as ER) can be evaluated using immunohistochemistry (IHC). One example of IHC testing is a semi-quantitative IHC interpretation system, the Allred score, which was developed to grade immunostained slides based upon the percentage and intensity of positively stained tumor cells.

The status of PR (as well as ER) can be evaluated using nucleic acid-based assays. For example, molecular assays such as gel-based, semi-quantitative RT-PCR assays (Chevillard et al., *Breast Cancer Res Treat* 1996, 41:81-89; Tong et al., *Anal Biochem* 1997, 251:173-177; Hackl et al., *Anticancer Res* 1998, 18:839-842; Shepard et al., *Mod Pathol.* 2000, 13:401-406; and Tong et al., *Clin Cancer Res* 1999, 5:1497-1502) and quantitative assays using real-time RT-PCR and nucleic acid sequence-based amplification (NASBA) technologies (Iwao et al., *Cancer* 2000, 89:1732-1738; de Cremoux et al., *Endocr Relat Cancer* 2004, 11:489-495; Labuhn et al., *Int J Biol Markers* 2006, 21:30-39; and Lamy et al., *Clin Chem Lab Med* 2006: 44:3-12) have been developed to measure the mRNA level of PR in frozen breast biopsy tissue samples. TaqMan® RT-PCR assays to quantitate PR mRNA levels in archived formalin-fixed, paraffin-embedded (FFPE) specimens have been reported (Cronin et al., *Am J Pathol* 2004, 164:35-42 and Ma et al., *J Clin Oncol* 2006, 24:4611-4619). Lamy et. al. (*Clin Chem Lab Med* 2006: 44:3-12) developed a duplex real-time NASBA assay using molecular beacon probes to measure mRNA levels of PGR along with the housekeeping gene PPIB. The results were then compared to a duplex quantitation curve to determine the hormonal receptor mRNA level in frozen tissue samples. Labuhn et. al. (*Int J Biol Markers.* 2006, 21:30-39) developed simplex TaqMan® assays to determine mRNA levels of PGR along with housekeeping gene 18S.

Nucleic acid-based assays of PR are also described in U.S. patent application Ser. No. 12/355,873, filed Jan. 19, 2009 by Sheng-Yung Chang et al., which is incorporated herein by reference in its entirety, particularly those portions of Ser. No. 12/355,873 which relate to PR.

SUMMARY OF THE INVENTION

The present invention relates to a prognostic signature typically comprising 14 genes (which may be referred to herein as a "metastasis score" ("MS"), and which is also described in U.S. Pat. No. 7,695,915, issued Apr. 13, 2010 to Kit Lau et al., which is incorporated herein by reference in its entirety) in combination with progesterone receptor (PR). This combination of MS and PR may be referred to herein as a "composite metastasis score" ("cMS") or "composite MSPR score" ("MSPR"). Furthermore, in preferred embodiments, the cMS is determined by applying weighted coefficients to MS and PR.

For example, in certain exemplary embodiments, the cMS is determined by applying a weighted coefficient of 0.0338 (or, equivalently, 0.03380) to MS and a weighted coefficient of –0.22026 (or –0.2203) to PR. In certain exemplary embodiments, these coefficients of 0.0338 for MS and –0.22026 (or –0.2203) for PR are used in conjunction with a SYBR® Green-based assay for detecting gene expression. Furthermore, in certain exemplary embodiments the cMS is determined by applying a weighted coefficient of 0.0326 to MS and a weighted coefficient of –0.2034 to PR. In certain exemplary embodiments, these coefficients of 0.0326 for MS and –0.2034 for PR are used in conjunction with a TaqMan®-based assay for detecting gene expression. Thus, in certain exemplary embodiments of the invention, the "composite metastasis score" ("cMS") is derived as follows:

$$cMS_u = \beta_{MS}*MS + \beta_{PR}*PR$$

where $\beta_{MS} = 0.0338$, and $\beta_{PR} = -0.22026$ or where $\beta_{MS} = 0.0326$, and $\beta_{PR} = -0.2034$ ($cMS_u$ indicates an un-scaled cMS)

The MS and PR values can be, for example, $-\Delta\Delta C_T$ (or $\Delta\Delta C_T$) values.

In other exemplary embodiments, a cMS is determined by applying other weighted coefficients to MS and/or PR. For example, further exemplary $\beta_{MS}$ values which can be applied to MS include, but are not limited to, 0.03, 0.04, 0.032, 0.033, or 0.034 (as well as similar values). Further exemplary $\beta_{PR}$ values which can be applied to PR include, but are not limited to, –0.2 (or, equivalently, –0.20), –0.22 (or, equivalently, –0.220), –0.203, –0.204, –0.2202, or –0.2203 (as well as similar values).

Additionally, based on a weighted MS coefficient ($\beta_{MS}$ value) of 0.0338, the lower and upper 95% confidence intervals are 0.0009 and 0.0667, respectively (see Tables 35A-35B). Thus, any value between 0.0009 and 0.0667 (inclusive) can be used as an MS coefficient ($\beta_{MS}$ value) in determining a cMS. Moreover, based on a weighted MS coefficient ($\beta_{MS}$ value) of 0.0326, the lower and upper 95% confidence intervals are 0.0006 and 0.0649, respectively (see Table 36). Thus, any value between 0.0006 and 0.0649 (inclusive) can be used as an MS coefficient ($\beta_{MS}$ value) in determining a cMS. Furthermore, based on combining the lowermost and uppermost ranges of these two 95% confidence interval, any value between 0.0006 and 0.0667 (inclusive) can be used as an MS coefficient ($\beta_{MS}$ value) in determining a cMS.

Similarly, based on a weighted PR coefficient ($\beta_{PR}$ value) of –0.2203, the lower and upper 95% confidence intervals are –0.3908 and –0.0497, respectively (see Tables 35A-35B). Thus, any value between –0.3908 and –0.0497 (inclusive) can be used as a PR coefficient ($\beta_{PR}$ value) in determining a cMS. Moreover, based on a weighted PR coefficient ($\beta_{PR}$ value) of –0.2034, the lower and upper 95% confidence intervals are –0.3614 and –0.0469, respectively (see Table 36). Thus, any value between –0.3614 and –0.0469 (inclusive) can be used as a PR coefficient ($\beta_{PR}$ value) in determining a cMS. Furthermore, based on combining the lowermost and uppermost ranges of these two 95% confidence interval, any value between –0.3614 and –0.0497 (inclusive) can be used as an PR coefficient ($\beta_{PR}$ value) in determining a cMS.

Optionally, the $cMS_u$ values can be rescaled to suit any desired scale. In one example, if the actual range of the $cMS_u$ values in a dataset ranges from –3.28 to 0.66, for a total range of 3.94, then the $cMS_u$ can be rescaled to a 0-40 scale by shifting the scores by 3.28 and multiplying by 10 (e.g., where $\beta_{MS} = 0.0338$, and $\beta_{PR} = -0.22026$ or –0.2203). In an alternative example, the $cMS_u$ can be rescaled to a 0-40 scale by shifting the scores by 3.1175 and multiplying by 10 (e.g., where $\beta_{MS}=0.0326$, and $\beta_{PR}=-0.2034$). These alternatives are demonstrated by the following equations:

$$cMS=(cMS_u+3.28)*10=0.338*MS_u-2.2026*PR+32.8$$
(for $\beta_{MS}=0.0338$, and $\beta_{PR}=-0.22026$)

or $cMS=(cMS_u+3.1175)*10=0.326*MS_u-2.034*PR+31.175$ (for $\beta_{MS}=0.0326$, and $\beta_{PR}=-0.2034$)

where
cMS=0 if cMS<0
cMS=40 if cMS>40

The cMS can further be compared to at least one predefined composite metastasis score threshold cutoff value (cMS threshold), such as to classify a breast cancer patient as being at increased or decreased risk for tumor metastasis (e.g., depending on whether their cMS value is above or below one or more predefined cMS threshold cutoff values). This can be done in a similar manner as described below for comparing the MS to an MS threshold (e.g., as described in the section below entitled "Clinical Application of the Metastasis Score (MS) in Risk Determination") or comparing PR to a PR threshold to determine PR status (e.g., as described in the section below entitled "Calculation of Progesterone Receptor (PR) mRNA Expression Levels and PR Status"). In certain embodiments, two or more cMS threshold cutoff values are used.

In certain exemplary embodiments, the cMS threshold is 1.738 or 1.74 (based on an un-scaled $cMS_u$), or 17.38 or 17.4 (based on re-scaling cMS to a 0-40 scale, as exemplified above), or a similar value.

The cMS is useful for predicting risk of metastasis of a breast tumor, particularly for estrogen receptor (ER)-positive breast tumors in patients who have been treated with tamoxifen. Furthermore, the cMS is particularly useful for early stage (stage I or II) and node-negative breast cancer. For example, the cMS is useful for identifying which patients are at greatest risk for metastasis (e.g., have the most aggressive breast tumors) such as distant metastasis, including recurrence of metastasis, so that these patients can be targeted for chemotherapy (e.g., chemotherapy can be added to tamoxifen treatment for these patients since tamoxifen alone is likely to be inadequate for preventing metastasis of the aggressive tumors in these patients), while sparing the adverse effects of chemotherapy for those patients whose metastasis risk may be extremely low.

Thus, in exemplary embodiments, the present invention provides a multi-gene signature (e.g., the 14-gene MS in combination with PR) that can be used for predicting breast cancer metastasis, methods and reagents for the detection of the genes disclosed herein, and assays or kits that utilize such reagents. In various exemplary embodiments, methods are provided for determining expression levels of the genes disclosed herein in a test sample, for determining an individual's probability of developing metastasis (e.g., distant metastasis), and for selecting and/or administering a treatment (e.g., determining whether or not to add chemotherapy to tamoxifen treatment, and/or administering chemotherapy). The breast cancer metastasis-associated genes disclosed herein are particularly useful for diagnosing, prognosing, screening for, and evaluating probability of distant metastasis of ER-positive tumors in breast cancer patients, especially in patients who have been treated with tamoxifen.

In certain embodiments, the invention provides a kit comprising reagents for detecting the expression levels of genes CENPA, PKMYT1, MELK, MYBL2, BUB1, RACGAP1, TK1, UBE2S, DC13, RFC4, PRR11, DIAPH3, ORC6L, CCNB1, and PR (PGR), and one or more components selected from the group consisting of an enzyme (e.g., polymerase and/or ligase enzyme, buffer, amplification primer pair, dNTPs, ddNTPs, positive and/or negative control nucleic acid, nucleic acid extraction reagent, instructions for using said test kit, instructions for calculating the MS and/or cMS, and/or instructions for determining risk of breast cancer metastasis based on the cMS.

In further embodiments, the invention provides a microarray comprising polynucleotides selectively hybridizing to genes CENPA, PKMYT1, MELK, MYBL2, BUB1, RACGAP1, TK1, UBE2S, DC13, RFC4, PRR11, DIAPH3, ORC6L, CCNB1, and PR (PGR).

SEQUENCE LISTING

The attached Sequence Listing is herein incorporated by reference in its entirety. The Sequence Listing provides oligonucleotide sequences (SEQ ID NOS:1-34) as shown in Table 3. These oligonucleotides are exemplary primers in the RT-PCR amplification of the genes/transcripts listed in Table 2.

Also provided in the Sequence Listing are four exemplary progesterone receptor (PR) transcript variants (SEQ ID NOS: 35-38) encoded by the PGR gene, as well as exemplary primer (SEQ ID NOS:39-40) and probe (SEQ ID NO:41) sequences for amplifying and/or detecting the PR transcripts (such as for use in determining PR expression in conjunction with the 14-gene metastasis score), as shown in Table 30.

BRIEF DESCRIPTIONS OF THE FIGURES

Figure 3:
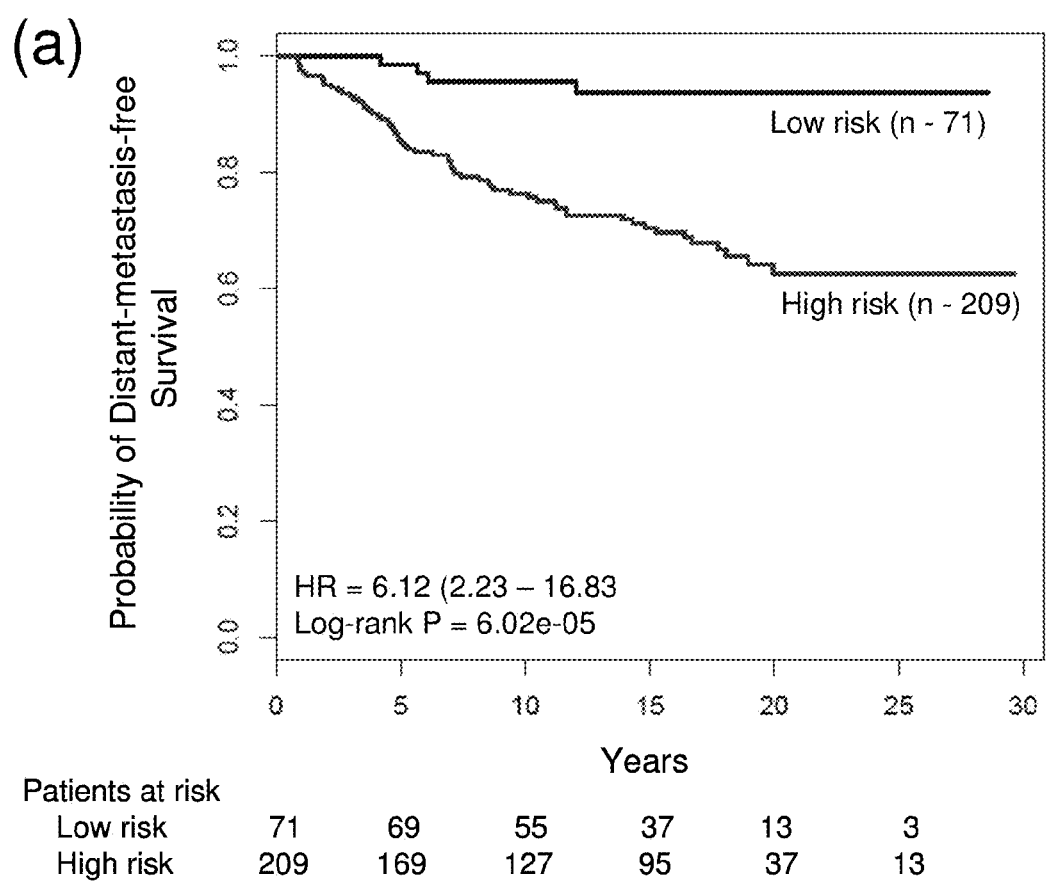
Figure 3:
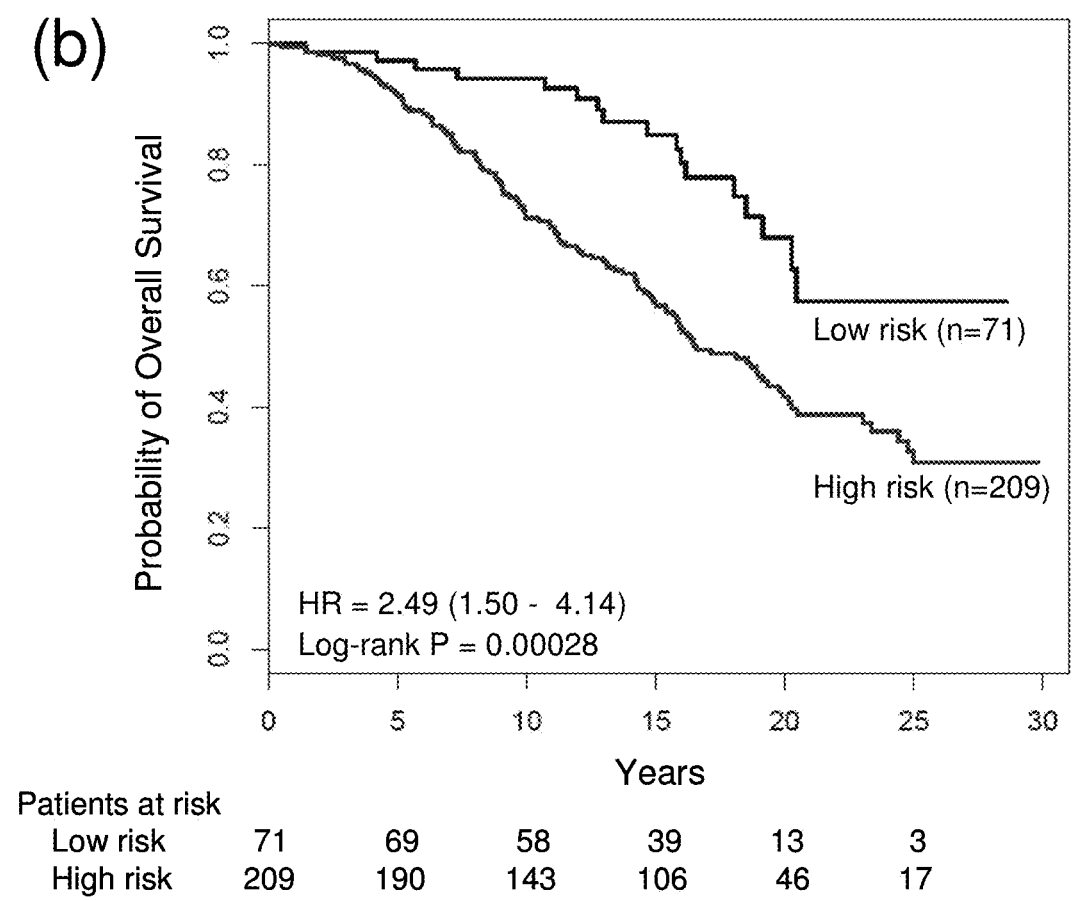
Figure 3:
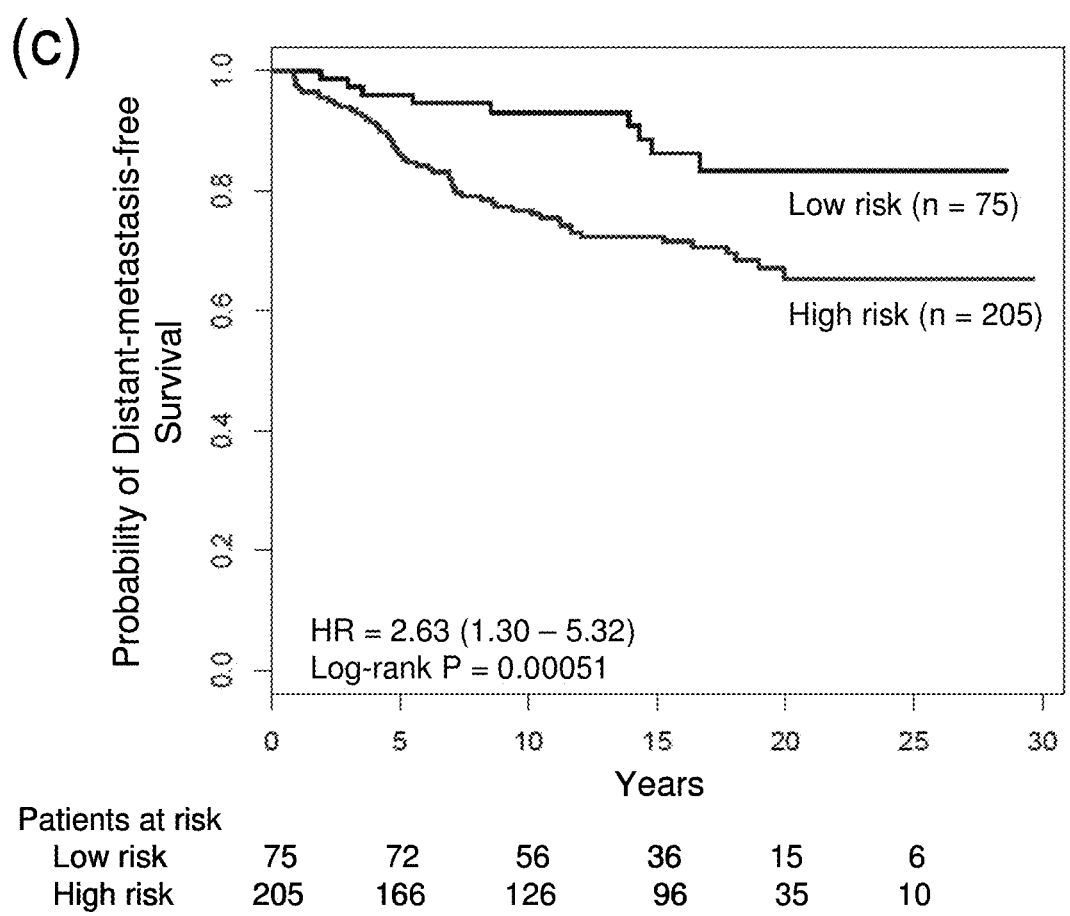
Figure 3:
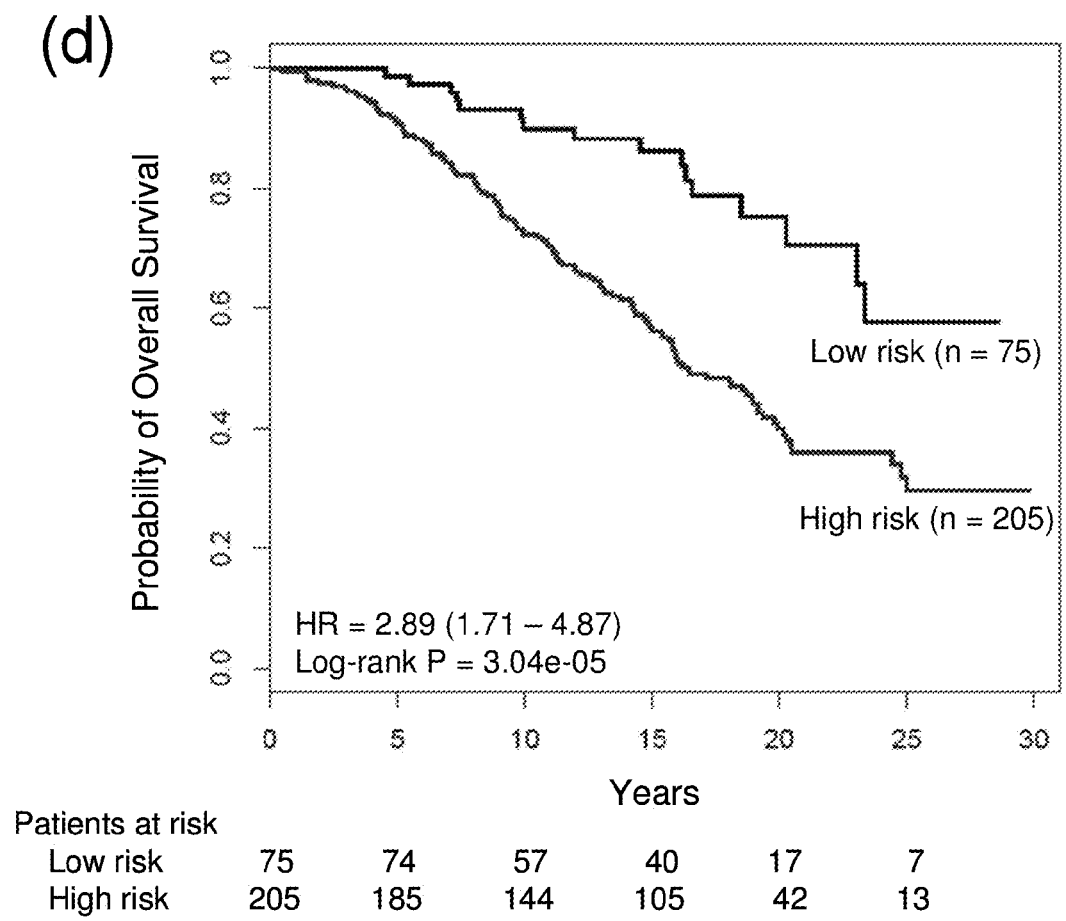

FIG. 3 shows Kaplan-Meier curves by risk groups defined by the gene signature and Adjuvant! in 280 untreated patients from Guy's Hospital. Specifically, FIGS. 3a) and b) describe results using the 14 gene signature, and FIGS. 3c) and d) describe results using the Adjuvant! factors. a) Time to distant me astases (DMFS) by MS risk groups b) Overall survival by MS risk groups c) Time to distant metastases (DMFS) by Adjuvant! risk groups d) Overall survival by Adjuvant! risk groups.

Figure 4:
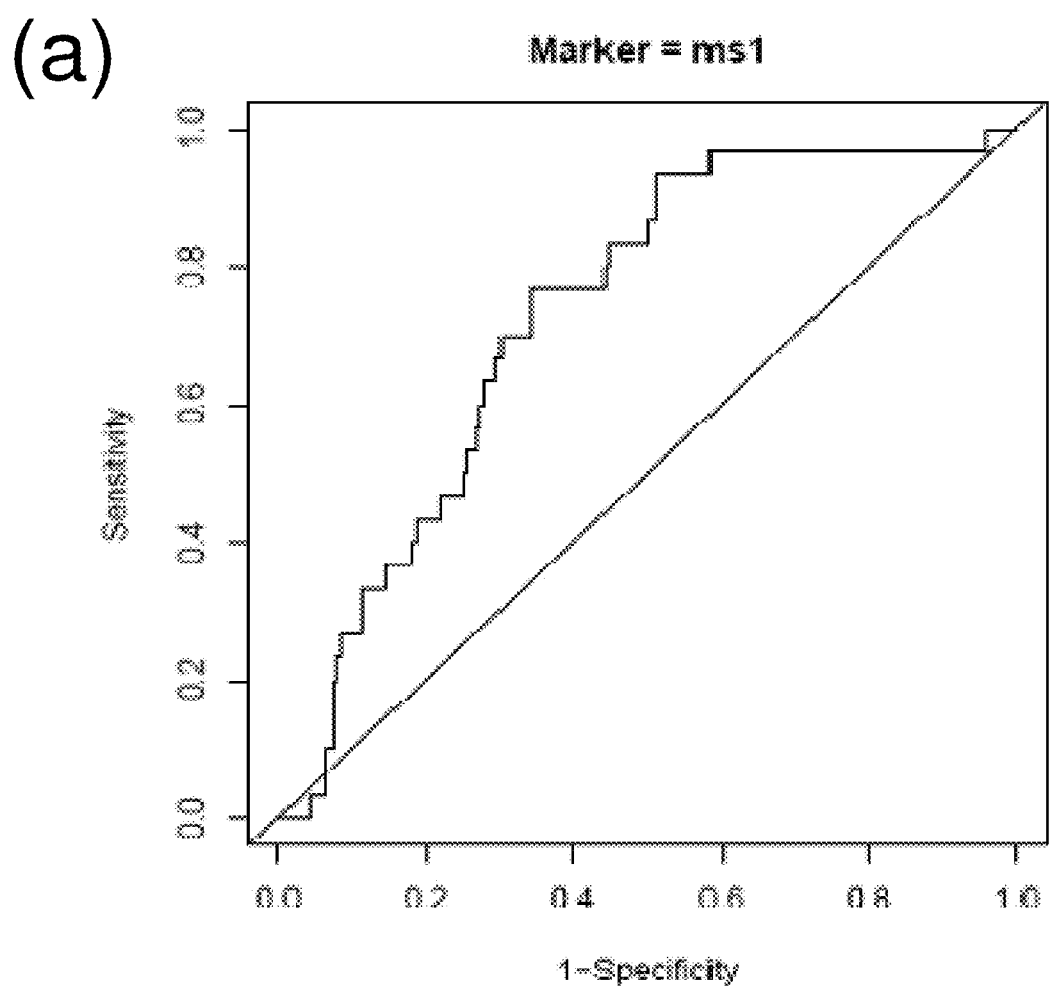
Figure 4:
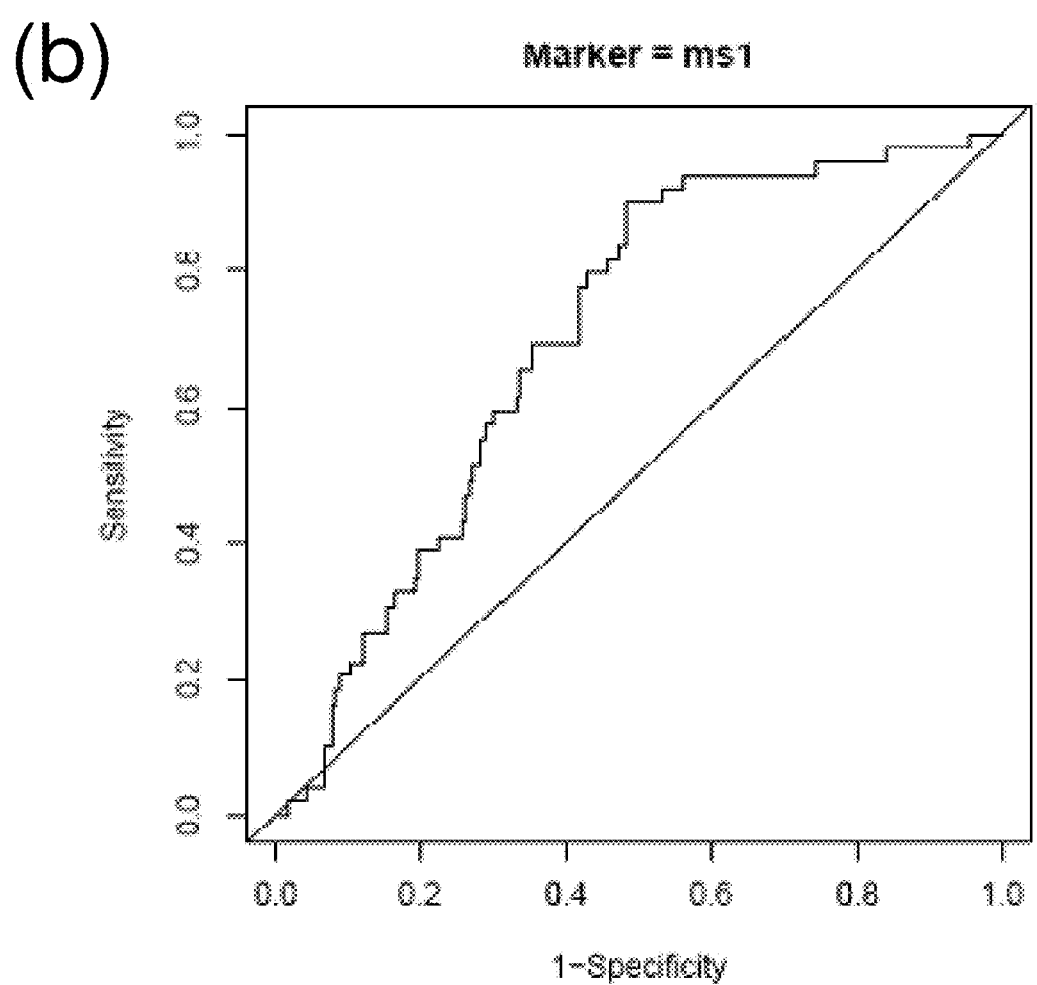
Figure 4:
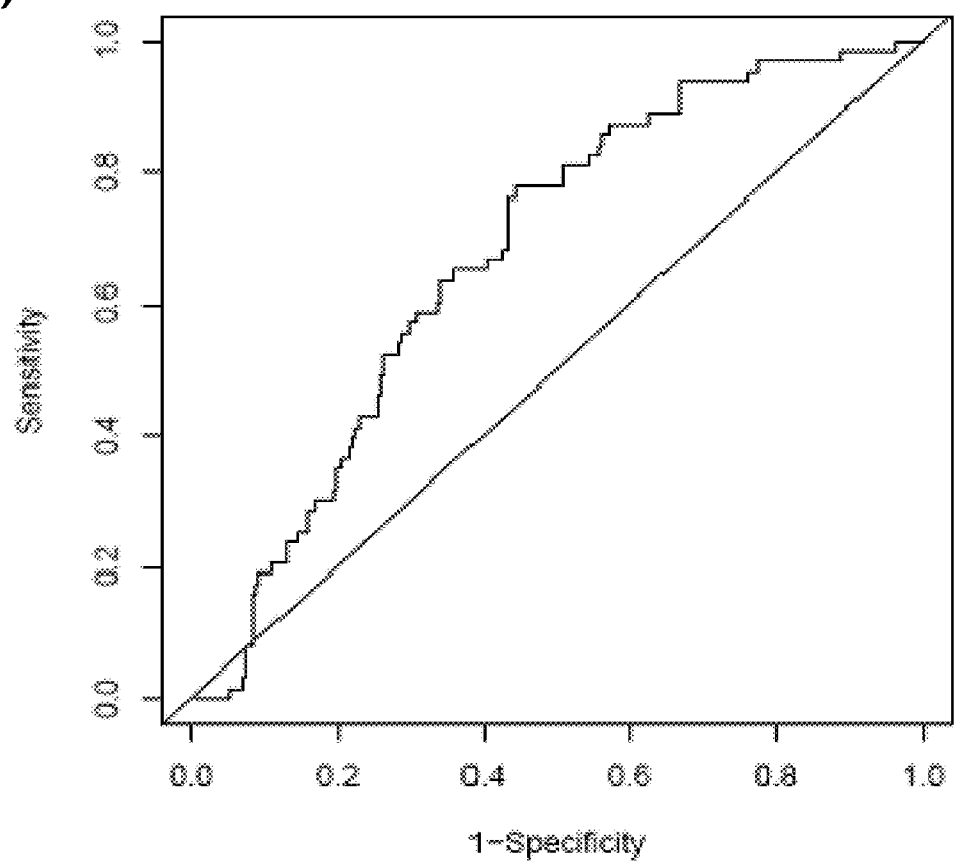
Figure 4:
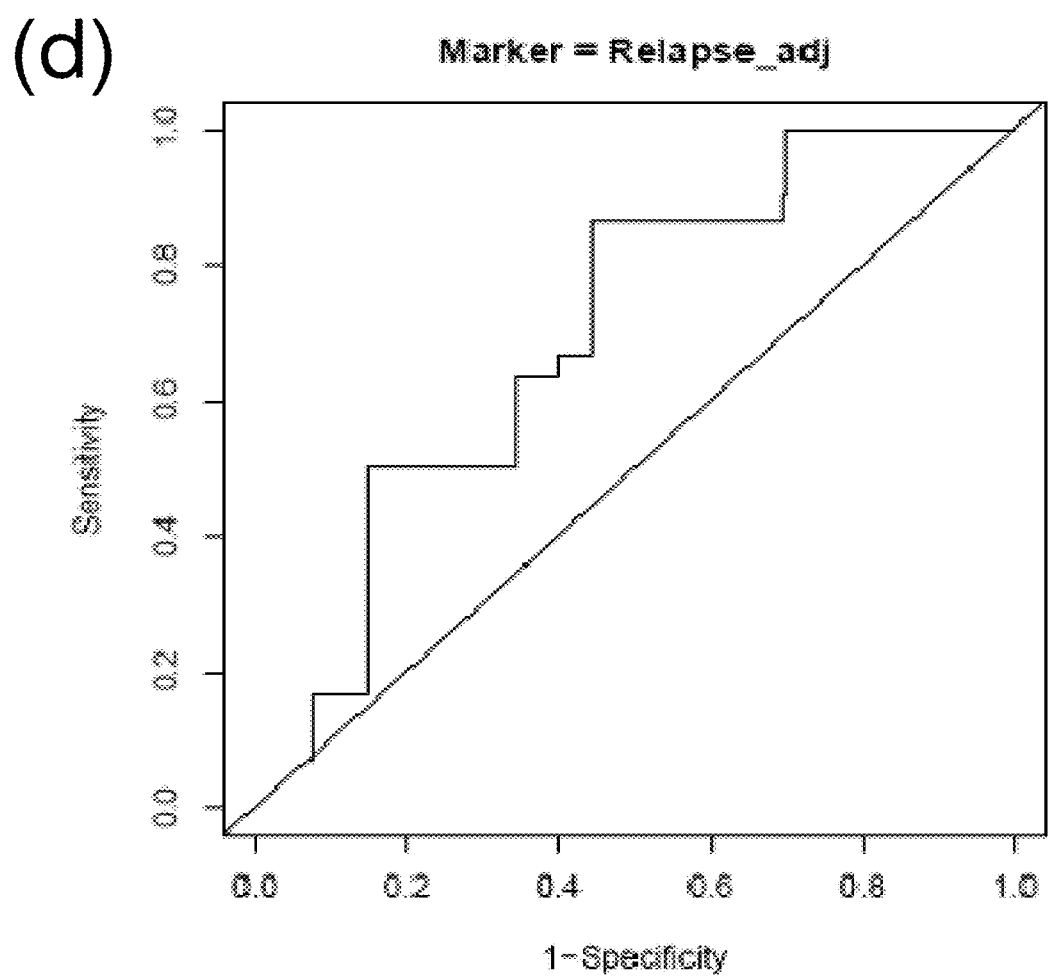
Figure 4:
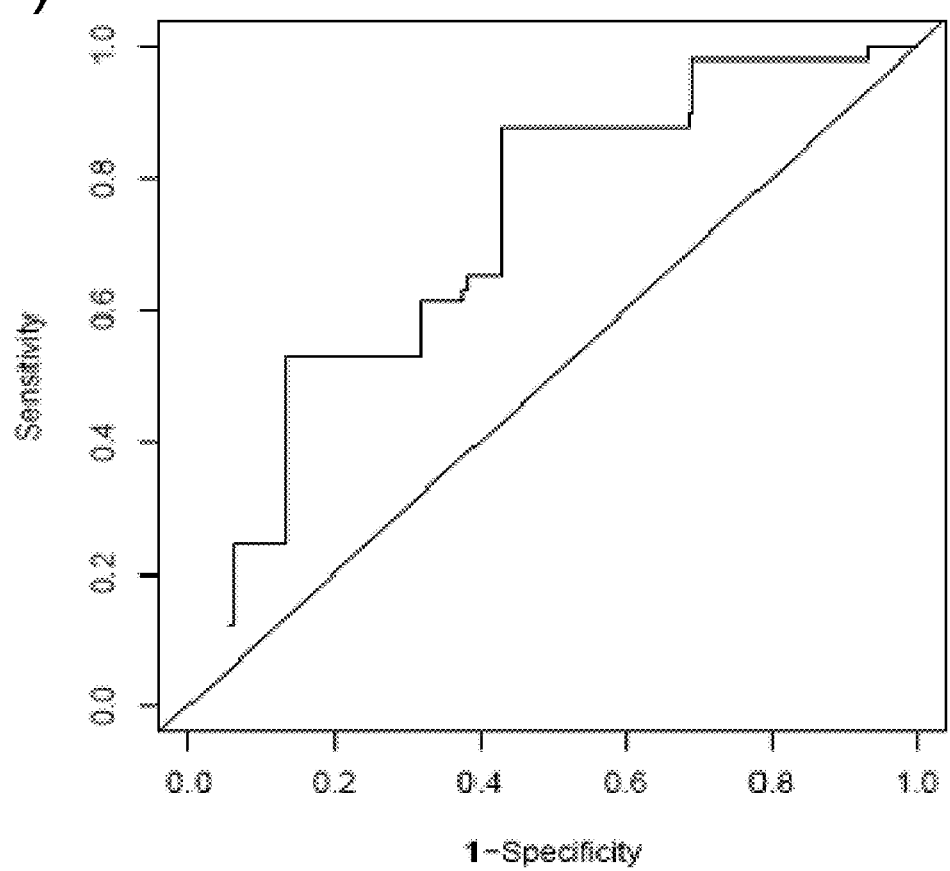
Figure 4:
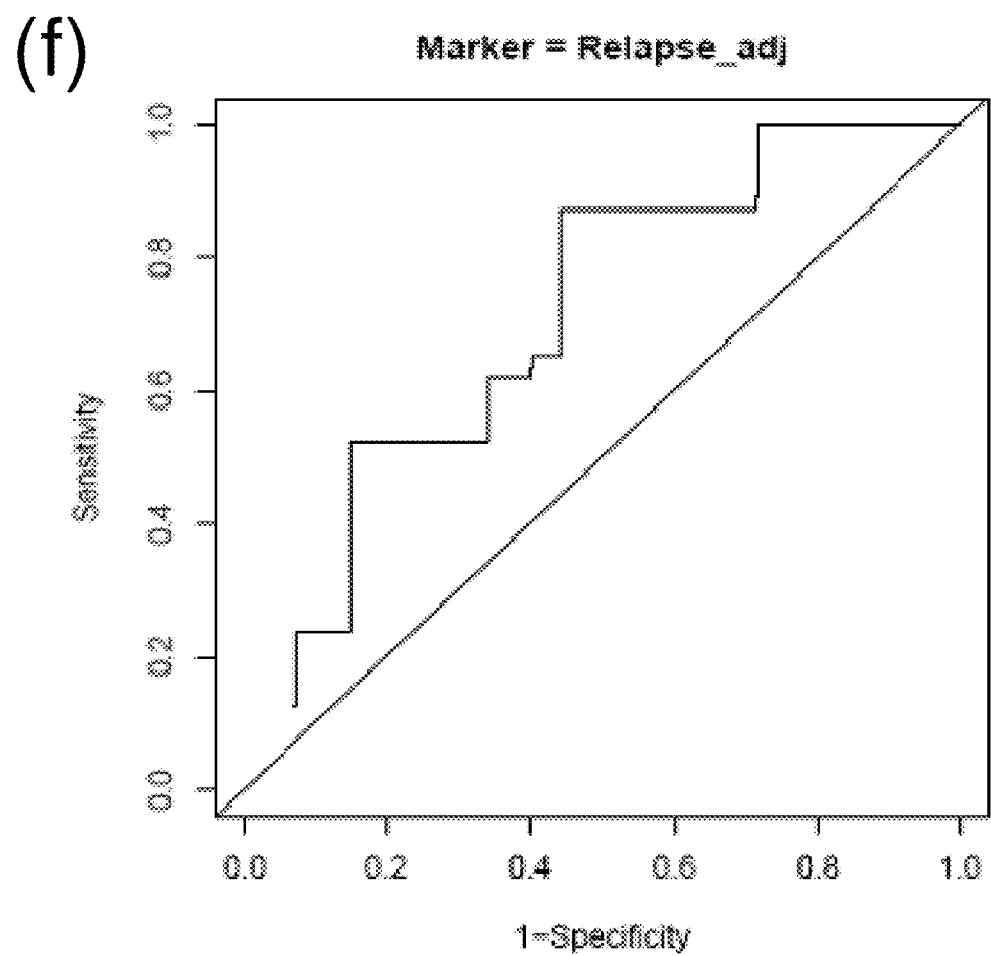

FIG. 4 shows Receiver operating characteristic (ROC) curves of the gene signature and of the online program Adjuvant! a) ROC curve for distant metastases within 5 years for the gene signature b) ROC curve for distant metastases within 10 years for the gene signature c) ROC curve for death within 10 years for the gene signature d) ROC curve for metastases within 5 years for Adjuvant! e) ROC curve for metastases within 10 years for Adjuvant! f) ROC curve for death within 10 years for Adjuvant! for untreated patients from Guy's Hospital FIG. 5 shows probability of distant metastasis within 5 years and 10 years vs. Metastasis Score (MS) from 280 Guy's untreated patients.

FIG. 6 is a comparison of probability of distant metastasis in 10 years from 14-gene signature vs, 10-year relapse probability from Adjuvant! for untreated patients from Guy's Hospital FIG. 7 shows Kaplan-Meier curves for distant-metastasis-free survival in University of Muenster patients.

FIG. 8 shows Kaplan-Meier curves of distant-metastasis-free survival in 3 MS groups (high, intermediate, low) for 205 treated patients from Guy's Hospital.

FIG. 9 shows Kaplan-Meier curves of distant-metastasis-free survival in 2 risk groups (high and low) determined by MS for 205 treated patients from Guy's Hospital.

FIG. 10 shows ROC curve of MS to predict distant metastasis in 5 years for Guy's treated samples, AUC=0.7(0.57–0.87).

FIG. 11 shows time dependence of hazard ratios of high vs. low risk groups by MS in Guy's treated samples.

FIG. 12 shows Kaplan-Meier curves of distant-metastasis-free survival (DMFS) for three MS groups (high, intermediate and low) in 234 Japanese samples.

FIG. 13 shows Kaplan-Meier curves of distant-metastasis-free survival (DMFS) for two risk groups (high MS have high risk whereas intermediate and low MS have low risk) in 234 Japanese samples.

FIG. 14 shows ROC curve of MS to predict distant metastasis in 5 years for Japanese patients. AUC=0.73(0.63–0.84).

FIG. 15 shows annualized hazard rate for MS groups and hazard ratio of high vs. low risk groups as a function of time.

FIG. 16 shows Kaplan-Meier estimates of distant-metastasis-free survival (DMFS) of a validation dataset by the composite metastasis score (cMS).

DETAILED DESCRIPTION OF THE INVENTION

Composite Metastasis Score (cMS)

The present invention relates to a prognostic signature typically comprising 14 genes (which may be referred to herein as a "metastasis score" ("MS") and is described below, and which is also described in U.S. Pat. No. 7,695,915, issued Apr. 13, 2010 to Kit Lau et al., which is incorporated herein by reference in its entirety) in combination with progesterone receptor (PR). This combination of MS and PR may be referred to herein as a "composite metastasis score" ("cMS") or "composite MSPR score" ("MSPR"). Furthermore, in preferred embodiments, the cMS is determined by applying weighted coefficients to MS and PR.

For example, in certain exemplary embodiments, the cMS is determined by applying a weighted coefficient of 0.0338 (or, equivalently, 0.03380) to MS and a weighted coefficient of –0.22026 (or –0.2203) to PR. In certain exemplary embodiments, these coefficients of 0.0338 for MS and –0.22026 (or –0.2203) for PR are used in conjunction with a SYBR® Green-based assay for detecting gene expression.

Furthermore, in certain exemplary embodiments the cMS is determined by applying a weighted coefficient of 0.0326 to MS and a weighted coefficient of –0.2034 to PR. In certain exemplary embodiments, these coefficients of 0.0326 for MS and –0.2034 for PR are used in conjunction with a TaqMan®-based assay for detecting gene expression.

Thus, in certain exemplary embodiments of the invention, the "composite metastasis score" ("cMS") is derived as follows:

$$cMS_u = \beta_{MS}*MS + \beta_{PR}*PR$$

where $\beta_{MS}$=0.0338, and $\beta_{PR}$=–0.22026
or where $\beta_{MS}$=0.0326, and $\beta_{PR}$=–0.2034
($cMS_u$ indicates an un-scaled cMS) The MS and PR values can be, for example, –ΔΔ$C_T$ (or ΔΔ$C_T$) values. In other exemplary embodiments, a cMS is determined by applying other weighted coefficients to MS and/or PR. For example, further exemplary $\beta_{MS}$ values which can be applied to MS include, but are not limited to, 0.03, 0.04, 0.032, 0.033, or 0.034 (as well as similar values). Further exemplary $\beta_{PR}$ values which can be applied to PR include, but are not limited to, –0.2 (or, equivalently, –0.20), –0.22 (or, equivalently, –0.220), –0.203, –0.204, –0.2202, or –0.2203 (as well as similar values).

Additionally, based on a weighted MS coefficient ($\beta_{MS}$ value) of 0.0338, the lower and upper 95% confidence intervals are 0.0009 and 0.0667, respectively (see Tables 35A-35B). Thus, any value between 0.0009 and 0.0667 (inclusive) can be used as an MS coefficient ($\beta_{MS}$ value) in determining a cMS. Moreover, based on a weighted MS coefficient ($\beta_{MS}$ value) of 0.0326, the lower and upper 95% confidence intervals are 0.0006 and 0.0649, respectively (see Table 36). Thus, any value between 0.0006 and 0.0649 (inclusive) can be used as an MS coefficient ($\beta_{MS}$ value) in determining a cMS. Furthermore, based on combining the lowermost and uppermost ranges of these two 95% confidence interval, any value between 0.0006 and 0.0667 (inclusive) can be used as an MS coefficient ($\beta_{MS}$ value) in determining a cMS.

Similarly, based on a weighted PR coefficient ($\beta_{PR}$ value) of –0.2203, the lower and upper 95% confidence intervals are –0.3908 and –0.0497, respectively (see Tables 35A-35B). Thus, any value between –0.3908 and –0.0497 (inclusive) can be used as a PR coefficient ($\beta_{PR}$ value) in determining a cMS. Moreover, based on a weighted PR coefficient ($\beta_{PR}$ value) of –0.2034, the lower and upper 95% confidence intervals are –0.3614 and –0.0469, respectively (see Table 36). Thus, any value between –0.3614 and –0.0469 (inclusive) can be used as a PR coefficient ($\beta_{PR}$ value) in determining a cMS. Furthermore, based on combining the lowermost and uppermost ranges of these two 95% confidence interval, any value between –0.3614 and –0.0497 (inclusive) can be used as an PR coefficient ($\beta_{PR}$ value) in determining a cMS.

Optionally, the $cMS_u$ values can be rescaled to suit any desired scale. In one example, if the actual range of the $cMS_u$ values in a dataset ranges from –3.28 to 0.66, for a total range of 3.94, then the $cMS_u$ can be rescaled to a 0-40 scale by shifting the scores by 3.28 and multiplying by 10 (e.g., where $\beta_{MS}$=0.0338, and $\beta_{PR}$=–0.22026 or –0.2203). In an alternative example, the $cMS_u$ can be rescaled to a 0-40 scale by shifting the scores by 3.1175 and multiplying by 10 (e.g., where $\beta_{MS}$=0.0326, and $\beta_{PR}$=–0.2034). These alternatives are demonstrated by the following equations:

$$cMS = (cMS_u + 3.28)*10 = 0.338*MS_u - 2.2026*PR + 32.8$$
$$(\text{for } \beta_{MS}=0.0338, \text{ and } \beta_{PR}=-0.22026)$$

or $$cMS = (cMS_u + 3.1175)*10 = 0.326*MS_u - 2.034*PR + 31.175 \text{ (for } \beta_{MS}=0.0326, \text{ and } \beta_{PR}=-0.2034)$$

where
cMS=0 if cMS<0
cMS=40 if cMS>40

The cMS can further be compared to at least one predefined composite metastasis score threshold cutoff value (cMS threshold), such as to classify a breast cancer patient as being at increased or decreased risk for tumor metastasis (e.g., depending on whether their cMS value is above or below one or more predefined cMS threshold cutoff values). This can be done in a similar manner as described below for comparing the MS to an MS threshold (e.g., as described in the section below entitled "Clinical Application of the Metastasis Score (MS) in Risk Determination") or comparing PR to a PR threshold to determine PR status (e.g., as described in the section below entitled "Calculation of Progesterone Receptor (PR) mRNA Expression Levels and PR Status"). In certain embodiments, two or more cMS threshold cutoff values are used.

In certain exemplary embodiments, the cMS threshold is 1.738 or 1.74 (based on an un-scaled $cMS_u$), or 17.38 or 17.4 (based on re-scaling cMS to a 0-40 scale, as exemplified above), or a similar value.

The cMS is useful for predicting risk of metastasis of a breast tumor, particularly for estrogen receptor (ER)-positive breast tumors in patients who have been treated with tamoxifen. Furthermore, the cMS is particularly useful for early stage (stage I or II) and node-negative breast cancer. For example, the cMS is useful for identifying which patients are at greatest risk for metastasis (e.g., have the most aggressive breast tumors) such as distant metastasis, including recurrence of metastasis, so that these patients can be targeted for chemotherapy (e.g., chemotherapy can be added to tamoxifen treatment for these patients since tamoxifen alone is likely to be inadequate for preventing metastasis of the aggressive tumors in these patients), while sparing the adverse effects of chemotherapy for those patients whose metastasis risk may be extremely low.

The PGR (progesterone receptor, PR) gene, an exemplary transcript sequence of which is provided by reference sequence NM_000926 (SEQ ID NO:35), and disclosed in Misrahi M, Atger M, et al., "Complete amino acid sequence of the human progesterone receptor deduced from cloned cDNA", *Biochem Biophys Res Commun.* 1987, 143(2):740-748. Three other PGR sequence variants are provided as reference sequences AB085683 (SEQ ID NO:36), AB085844 (SEQ ID NO:37), and AB085845 (SEQ ID NO:38) (see Table 30). Said reference sequences and reference citation are herein incorporated by reference in their entirety.

As indicated above, exemplary embodiments of the composite metastasis score (cMS) of the present invention include the 14-gene metastasis score (MS) as an element (along with PR) of the cMS. Thus, the MS is described herein below in addition to being described in U.S. Pat. No. 7,695,915 (incorporated herein by reference).

Metastasis Score (MS)

The metastasis score (MS) (which may also be referred to as a "proliferation index") is based, in part, on studies of early stage, lymph node-negative, ER-positive breast cancer patients who most need additional information to guide therapeutic decisions following primary breast cancer diagnosis. The 14 genes in the molecular signature of the MS are disclosed in Table 2. One skilled in the art can perform expression profiling of the 14 genes of the MS, using RNA obtained from a number of possible sources, and then insert the expression data into the provided MS algorithm to determine a prognostic metastasis score. The MS described here is also described in U.S. Pat. No. 7,695,915 (incorporated herein by reference).

In one aspect of the MS, it relates to a method of determining risk associated with tumor metastasis in a breast cancer patient, comprising measuring mRNA expression of the genes known as CENPA, PKMYT1, MELK, MYBL2, BUB1, RACGAP1, TK1, UBE2S, DC13, RFC4, PRR11, DIAPH3, ORC6L and CCNB1 in estrogen receptor-positive tumor cells of the breast cancer patient, and predicting risk of tumor metastasis based on mRNA expression levels of said genes.

In another aspect of the MS, it relates to a method of determining risk associated with tumor metastasis in a breast cancer patient, comprising measuring the expression level of genes CENPA, PKMYT1, MELK, MYBL2, BUB1, RACGAP1, TK1, UBE2S, DC13, RFC4, PRR11, DIAPH3, ORC6L and CCNB1 in estrogen receptor-positive tumor cells of said breast cancer patient, thereby obtaining a metastasis score (MS) based upon the expression levels of said genes, and determining risk of tumor metastasis for said breast cancer patient by comparing said metastasis score to a predefined metastasis score cut point (MS Threshold).

In a further aspect of the MS, the breast cancer patient is determined to have an increased risk of tumor metastasis if their MS is higher than the predefined MS Threshold.

In another aspect of the MS, the breast cancer patient is determined to have a decreased risk of tumor metastasis if their MS is lower than the predefined MS Threshold.

In a certain aspects of the MS, it relates to a method of determining risk associated with tumor metastasis in a breast cancer patient, in which mRNA of the 14-gene signature is obtained from ER-positive tumor cells, reverse transcribed to cDNA, and detected by polymerase chain reaction (PCR) amplification.

In another aspect of the MS, it relates to a method of determining risk associated with tumor metastasis in a breast cancer patient, in which mRNA of ER-positive tumor cells is reverse transcribed and amplified by the two primers associated with each gene/transcript as presented in Table 3, SEQ ID NOS. 1-34.

In another aspect of the MS, it relates to a method of determining risk associated with tumor metastasis in a breast cancer patient, in which measurements of mRNA expression from ER-positive tumor cells are normalized against the mRNA expression of any one of the genes known as NUP214, PPIG and SLU7, or a combination thereof, as endogenous control(s).

In another aspect of the MS, it relates to a method of determining risk associated with tumor metastasis in a breast cancer patient, in which mRNA expression from ER-positive tumor cells is detected by a microarray.

In another aspect of the MS, it relates to a method of determining risk of tumor metastasis in a breast cancer patient, in which the mRNA expression is computed into a MS by the following:

$$MS_u = -\left[\sum_{i=1}^{14} Gi\right]$$

where Gi represents the expression level of each gene (i) of the 14-gene prognostic signature ($MS_u$ indicates an un-scaled MS). The value of Gi is the ΔΔCt obtained in expression profiling described in Equation 4 below.

In another aspect of the MS, it relates to a method of determining risk associated with tumor metastasis in a breast cancer patient, in which the mRNA expression is computed into a MS by the following:

$$MS = a0 + \sum_{i=1}^{M} ai * Gi$$

where M=14, Gi=the standardized expression level of each gene (i) of the 14 said genes, a0=0.022, and ai corresponds to the value presented in Table 2 for each of the genes in the 14-gene signature.

In another aspect of the MS, it relates to a method of determining risk associated with tumor metastasis in a breast cancer patient, in which the mRNA expression is computed into a MS by the following:

$$MS = a0 + b * \left[\sum_{i=1}^{M} ai * Gi\right] \quad \text{Equation 1}$$

where M=14, Gi=the standardized expression level of each gene (i) of the 14 said genes, a0=0.022, b=−0.251 and ai corresponds to the value presented in Table 2 for each of the genes in the 14-gene signature. Standardized expression level is obtained by subtracting the mean expression of that gene in the training set from the expression level measured in Δ(ΔCt) and then divided by the standard deviation of the gene expression in that gene. The mean and standard deviation of gene expression for each gene in the training set were presented in Table 4. Equation 1 was used in Examples 1, 2 and 3.

In a further aspect of the MS, the MS formula can assume the following definition $$MS = a0 + b * \left[\sum_{i=1}^{M} ai * Gi\right] \quad \text{Equation 2}$$

where M=14, Gi=expression level measured in Δ(ΔCt) of each gene (i) of the 14 said genes, a0=0.8657, b=−0.04778, ai=1 for all genes. Equation 2 was used in Examples 4 and 5.

In a further aspect of the MS, the MS formula can have a0=0, b=−1, and ai=1.

In another aspect of the MS, it relates to a method of determining risk associated with tumor metastasis in a breast cancer patient using expression profiling of the 14 genes mentioned above, in which the expression level Gi of each gene (i) is computed into a gene expression value Gi by the following:

$$\Delta(\Delta Ct) = (Ct_{GOI} - Ct_{EC})_{testRNA} - (Ct_{GOI} - Ct_{EC})_{refRNA} \quad \text{Equation 4}$$

where Ct is the PCR threshold cycle of exponential target amplification, GOI=gene of interest, EC=endogenous control, test RNA=patient sample RNA, ref RNA=reference RNA.

In another aspect of the MS, it relates to a method of determining risk associated with tumor metastasis in a breast cancer patient using expression profiling of the 14 genes mentioned above, in which the expression level Gi of each gene (i) is combined into a single MS value, wherein a patient with a MS higher than the relevant MS Threshold or cut point would be classified as being at higher risk for tumor metastasis.

Table 2 provides information about each of the 14 genes of the MS, including a reference sequence (RefSeq), obtained from the National Center for Biotechnology Information (NCBI) of the National Institutes of Health/National Library of Medicine, which identifies an exemplary transcript sequence of each described gene. Based on the sequence of each exemplary transcript sequence, reagents may be designed to detect all variants of each gene of the 14-gene signature. Table 3 provides exemplary primer sets that can be used to detect each gene of the 14-gene signature in a manner such that known variants of each gene are amplified. Thus, the present invention provides for expression profiling of any transcript variants of the genes disclosed herein.

Also shown in Table 2 is a citation for a reference that published the nucleotide sequence of each RefSeq. These references are all incorporated herein by reference in their entirety. Also in Table 2 is a description of each gene. The reference citations and gene descriptions are from NCBI.

The CENPA gene is identified by reference sequence NM_001809 and disclosed in Black, B. E., Foltz, D. R., et al., 2004, Nature 430(6999):578-582. Said reference sequence and reference are herein incorporated by reference in their entirety.

The PKMYT1 gene, identified by reference sequence NM_004203, and disclosed in Bryan, B. A., Dyson, O. F. et al., 2006, J. Gen. Virol. 87 (PT 3), 519-529. Said reference sequence and reference are herein incorporated by reference in their entirety.

The MELK gene, identified by reference sequence NM_014791, and disclosed in Beullens, M., Vancauwenbergh, S. et al., 2005, J. Biol. Chem. 280 (48), 40003-40011. Said reference sequence and reference are herein incorporated by reference in their entirety.

The MYBL2 gene, identified by reference sequence NM_002466, and disclosed in Bryan, B. A., Dyson, O. F. et al., 2006, J. Gen. Virol. 87 (PT 3), 519-529. Said reference sequence and reference are herein incorporated by reference in their entirety.

The BUB1 gene, identified by reference sequence NM_004366, and disclosed in Morrow, C. J., Tighei, A. et al., 2005, J. Cell. Sci. 118 (PT 16), 3639-3652. Said reference sequence and reference are herein incorporated by reference in their entirety.

The RACGAP1 gene, identified by reference sequence NM_013277, and disclosed in Niiya, F., Xie, X. et al., 2005, J. Biol. Chem. 280 (43), 36502-36509. Said reference sequence and reference are herein incorporated by reference in their entirety.

The TK1 gene, identified by reference sequence NM_003258, and disclosed in Karbownik, M., Brzezianska, E. et al., 2005, Cancer Lett. 225 (2), 267-273. Said reference sequence and reference are herein incorporated by reference in their entirety.

The UBE2S gene, identified by reference sequence NM_014501, and disclosed in Liu, Z., Diaz, L. A. et al., 1992, J. Biol. Chem. 267 (22), 15829-15835. Said reference sequence and reference are herein incorporated by reference in their entirety.

The DC13 gene, identified by reference sequence AF201935, and disclosed in Gu, Y., Peng, Y. et al., Direct Submission, Submitted Nov. 5, 1999, Chinese National Human Genome Center at Shanghai, 351 Guo Shoujing Road, Zhangjiang Hi-Tech Park, Pudong, Shanghai 201203, P. R. China. Said reference sequence and reference are herein incorporated by reference in their entirety.

The RFC4 gene, identified by reference sequence NM_002916, and disclosed in Gupte, R. S., Weng, Y. et al., 2005, Cell Cycle 4 (2), 323-329. Said reference sequence and reference are herein incorporated by reference in their entirety.

The PRR11 gene, identified by reference sequence NM_018304, and disclosed in Weinmann, A. S., Yan, P. S. et al., 2002, Genes Dev. 16 (2), 235-244. Said reference sequence and reference are herein incorporated by reference in their entirety.

The DIAPH3 gene, identified by reference sequence NM_030932, and disclosed in Katoh, M. and Katoh, M., 2004, Int. J. Mol. Med. 13 (3), 473-478. Said reference sequence and reference are herein incorporated by reference in their entirety.

The ORC6L gene, identified by reference sequence NM_014321, and disclosed in Sibani, S., Price, G. B. et al., 2005, Biochemistry 44 (21), 7885-7896. Said reference sequence and reference are herein incorporated by reference in their entirety.

The CCNB1 gene, identified by reference sequence NM_031966, and disclosed in Zhao, M., Kim, Y. T. et al., 2006, Exp Oncol 28 (1), 44-48. Said reference sequence and reference are herein incorporated by reference in their entirety.

The PPIG gene, identified by reference sequence NM_004792, and disclosed in Lin, C. L., Leu, S. et al., 2004, Biochem. Biophys. Res. Commun. 321 (3), 638-647. Said reference sequence and reference are herein incorporated by reference in their entirety.

The NUP214 gene, identified by reference sequence NM_005085, and disclosed in Graux, C., Cools, J. et al., 2004, Nat. Genet. 36 (10), 1084-1089. Said reference sequence and reference are herein incorporated by reference in their entirety.

The SLU7 gene, identified by reference sequence NM_006425, and disclosed in Shomron, N., Alberstein, M. et al., 2005, J. Cell. Sci. 118 (PT 6), 1151-1159. Said reference sequence and reference are herein incorporated by reference in their entirety.

Also shown in Table 2 is the value for an exemplary constant ai that can be used for determining the metastasis score for each gene i, based on the expression profiling results obtained for that gene. The derivation of the metastasis score and its use, and methods of gene expression profiling and use of the data obtained therefrom, are described below.

Thus, the MS typically comprises 14 genes which can be used with PR in the cMS described in exemplary embodiments of the invention (exemplary information about PR (gene PGR) is provided in Table 30). Further, weighted coefficients can be applied to MS, as well as to PR, in the cMS, such as to determine risk for breast cancer metastasis.

Those skilled in the art will readily recognize that nucleic acid molecules may be double-stranded molecules and that reference to a particular sequence of one strand refers, as well, to the corresponding site on a complementary strand. In defining a nucleotide sequence, reference to an adenine, a thymine (uridine), a cytosine, or a guanine at a particular site on one strand of a nucleic acid molecule also defines the thymine (uridine), adenine, guanine, or cytosine (respectively) at the corresponding site on a complementary strand of the nucleic acid molecule. Thus, reference may be made to either strand in order to refer to a particular nucleotide sequence. Probes and primers may be designed to hybridize to either strand and gene expression profiling methods disclosed herein may generally target either strand.

Tumor Tissue Source and RNA Extraction

In exemplary embodiments of the invention, target polynucleotide molecules are extracted from a sample taken from an individual afflicted with breast cancer. The sample may be collected in any clinically acceptable manner, but must be collected such that gene-specific polynucleotides (i.e., transcript RNA, or message) are preserved. The mRNA or nucleic acids so obtained from the sample may then be analyzed further. For example, pairs of oligonucleotides specific for a gene/transcript (e.g., the genes/transcripts presented in Tables 2 and 30) may be used to amplify the specific mRNA(s) in the sample. The amount of each message can then be determined, or profiled, and the correlation with a disease prognosis can be made. Alternatively, mRNA or nucleic acids derived therefrom (i.e., cDNA, amplified DNA or enriched RNA) may be labeled distinguishably from standard or control polynucleotide molecules, and both may be simultaneously or independently hybridized to a microarray comprising some or all of the markers or marker sets or subsets described above. Alternatively, mRNA or nucleic acids derived there from may be labeled with the same label as the standard or control polynucleotide molecules, wherein the intensity of hybridization of each at a particular probe is compared.

A sample may comprise any clinically relevant tissue sample, such as a formalin fixed paraffin embedded sample, frozen sample, tumor biopsy or fine needle aspirate, or a sample of bodily fluid containing ER-positive tumor cells such as blood, plasma, serum, lymph, ascitic or cystic fluid, urine, or nipple exudate.

Methods for preparing total and poly (A)+ RNA are well known and are described generally in Sambrook et al., MOLECULAR CLONING—A LABORATORY MANUAL (2ND ED.), Vols. 1-3, Cold Spring Harbor Laboratory, Cold Spring Harbor, N.Y. (1989)) and Ausubel et al., Current Protocols in Molecular Biology vol. 2, Current Protocols Publishing, New York (1994)). RNA may be isolated from ER-positive tumor cells by any procedures well-known in the art, generally involving lysis of the cells and denaturation of the proteins contained therein.

As an example of preparing RNA from tissue samples, RNA may also be isolated from formalin-fixed paraffin-embedded (FFPE) tissues using techniques well known in the art. Commercial kits for this purpose may be obtained, e.g., from Zymo Research, Ambion, Qiagen, or Stratagene. An exemplary method of isolating total RNA from FFPE tissue, according to the method of the Pinpoint Slide RNA Isolation System (Zymo Reasearch, Orange, Calif.) is as follows. Briefly, the solution obtained from the Zymo kit is applied over the selected FFPE tissue region of interest and allowed to dry. The embedded tissue is then removed from the slide and placed in a centrifuge tube with proteinase K. The tissue is incubated for several hours, then the cell lysate is centrifuged and the supernatant transferred to another tube. RNA is extracted from the lysate by means of a guanidinium thiocynate/β mercaptoethanol solution, to which ethanol is added and mixed. Sample is applied to a spin column, and spun one minute. The column is washed with buffer containing ethanol and Tris/EDTA. DNase is added to the column, and incubated. RNA is eluted from the column by adding heated RNase-free water to the column and centrifuging. Pure total RNA is present in the eluate.

Additional steps may be employed to remove contaminating DNA, such as the addition of DNase to the spin column, described above. Cell lysis may be accomplished with a non-ionic detergent, followed by micro-centrifugation to remove the nuclei and hence the bulk of the cellular DNA. In one embodiment, RNA is extracted from cells of the various types of interest by cell lysis in the presence of guanidinium thiocyanate, followed by CsCl centrifugation to separate the RNA from DNA (Chirgwin et al., *Biochemistry* 18:5294-5299 (1979)). Poly(A)+ RNA is selected with oligo-dT cellulose (see Sambrook et al., MOLECULAR CLONING—A LABORATORY MANUAL (2ND ED.), Vols. 1-3, Cold Spring Harbor Laboratory, Cold Spring Harbor, N.Y. (1989). Alternatively, separation of RNA from DNA can be accomplished by organic extraction, for example, with hot phenol or phenol/chloroform/isoamyl alcohol.

If desired, RNase inhibitors may be added to the lysis buffer. Likewise, for certain cell types it may be desirable to add a protein denaturation/digestion step to the protocol.

For many applications, it is desirable to preferentially enrich mRNA with respect to other cellular RNAs extracted from cells, such as transfer RNA (tRNA) and ribosomal RNA (rRNA). Most mRNAs contain poly(A) tails at their 3' ends. This allows for enrichment by affinity chromatography; for example, using oligo(dT) or poly(U) coupled to a solid support, such as cellulose or Sephadex™ (see Ausubel et al., CURRENT PROTOCOLS IN MOLECULAR BIOLOGY, vol. 2, Current Protocols Publishing, New York (1994). After being bound in this manner, poly(A)+ mRNA is eluted from the affinity column using 2 mM EDTA/0.1% SDS.

The sample of RNA can comprise a plurality of different mRNA molecules, each mRNA molecule having a different nucleotide sequence. In certain embodiments, the mRNA molecules of the RNA sample comprise mRNA corresponding to each of the 14 genes disclosed herein. In further embodiments, total RNA or mRNA from cells can be used in the methods of the invention. The source of the RNA can be, for example, cells from any ER-positive tumor cell. In specific embodiments, the methods of the invention are used with a sample containing total mRNA or total RNA from $1 \times 10^6$ cells or fewer.

Reagents for Measuring Gene Expression

Exemplary embodiments of the invention provide nucleic acid molecules that can be used in gene expression profiling and in determining prognosis of breast cancer metastasis. Exemplary nucleic acid molecules that can be used as primers in gene expression profiling of the 14 genes of the MS described herein are shown in Table 3, and exemplary nucleic acid molecules that can be used as primers and probes in gene expression profiling of PR (gene PGR) are shown in Table 30. These primers and probes are useful for amplifying and/or detecting mRNA expressed by each of these genes.

As indicated in Table 3:

Gene BUB1 is reverse-transcribed and amplified with SEQ ID NO: 1 as the Upper primer (5'), and SEQ ID NO: 2 as the Lower primer (3').

Gene CCNB1 is reverse-transcribed and amplified with SEQ ID NO: 3 as the Upper primer (5'), and SEQ ID NO: 4 as the Lower primer (3').

Gene CENPA is reverse-transcribed and amplified with SEQ ID NO: 5 as the Upper primer (5'), and SEQ ID NO: 6 as the Lower primer (3').

Gene DC13 is reverse-transcribed and amplified with SEQ ID NO: 7 as the Upper primer (5'), and SEQ ID NO: 8 as the Lower primer (3').

Gene DIAPH3 is reverse-transcribed and amplified with SEQ ID NO: 9 as the Upper primer (5'), and SEQ ID NO: 10 as the Lower primer (3').

Gene MELK is reverse-transcribed and amplified with SEQ ID NO: 11 as the Upper primer (5'), and SEQ ID NO: 12 as the Lower primer (3').

Gene MYBL2 is reverse-transcribed and amplified with SEQ ID NO: 13 as the Upper primer (5'), and SEQ ID NO: 14 as the Lower primer (3').

Gene NUP214 is reverse-transcribed and amplified with SEQ ID NO: 29 as the Upper primer (5'), and SEQ ID NO: 30 as the Lower primer (3').

Gene ORC6L is reverse-transcribed and amplified with SEQ ID NO: 15 as the Upper primer (5'), and SEQ ID NO: 16 as the Lower primer (3').

Gene PKMYT1 is reverse-transcribed and amplified with SEQ ID NO: 17 as the Upper primer (5'), and SEQ ID NO: 18 as the Lower primer (3').

Gene PPIG is reverse-transcribed and amplified with SEQ ID NO: 31 as the Upper primer (5'), and SEQ ID NO: 32 as the Lower primer (3').

Gene PRR11 is reverse-transcribed and amplified with SEQ ID NO: 19 as the Upper primer (5'), and SEQ ID NO: 20 as the Lower primer (3').

Gene RACGAP1 is reverse-transcribed and amplified with SEQ ID NO: 21 as the Upper primer (5'), and SEQ ID NO: 22 as the Lower primer (3').

Gene RFC4 is reverse-transcribed and amplified with SEQ ID NO: 23 as the Upper primer (5'), and SEQ ID NO: 24 as the Lower primer (3').

Gene SLU7 is reverse-transcribed and amplified with SEQ ID NO: 33 as the Upper primer (5'), and SEQ ID NO: 34 as the Lower primer (3').

Gene TK1 is reverse-transcribed and amplified with SEQ ID NO: 25 as the Upper primer (5'), and SEQ ID NO: 26 as the Lower primer (3').

Gene UBE2S is reverse-transcribed and amplified with SEQ ID NO: 27 as the Upper primer (5'), and SEQ ID NO: 28 as the Lower primer (3').

As indicated in Table 30:

Gene PGR can be reverse-transcribed and amplified with SEQ ID NO:39 as the upper primer (5'), and SEQ ID NO:40 as the lower primer (3'), and can also be detected with the probe of SEQ ID NO:41 (e.g., in a TaqMan® or other assay).

Based on the complete nucleotide sequence of each gene/transcript as shown in Tables 2 and 30, one skilled in the art can readily design and synthesize additional primers and/or probes that can be used in the amplification and/or detection of the 14 genes of the MS described herein, as well as PR.

In certain aspects of the invention, the sequences disclosed in Tables 3 and 30 can be used in reagents for gene expression profiling of the 14 genes of the MS, as well as PR. As used herein, a "gene expression profiling reagent" is a reagent that is specifically useful in the process of amplifying and/or detecting the nucleotide sequence of a specific target gene, whether that sequence is mRNA or cDNA, of the genes described herein. For example, the profiling reagent preferably can differentiate between different alternative gene nucleotide sequences, thereby allowing the identity and quantification of the nucleotide sequence to be determined. Typically, such a profiling reagent hybridizes to a target nucleic acid molecule by complementary base-pairing in a sequence-specific manner, and discriminates the target sequence from other nucleic acid sequences such as an art-known form in a test sample. An example of a detection reagent is a probe that hybridizes to a target nucleic acid containing a nucleotide sequence substantially complementary to one of the sequences provided in Tables 3 and 30. In a preferred embodiment, such a probe can differentiate between nucleic acids of different genes. Another example of a detection reagent is a primer which acts as an initiation point of nucleotide extension along a complementary strand of a target polynucleotide, as in reverse transcription or PCR. The sequence information provided herein is also useful, for example, for designing primers to reverse transcribe and/or amplify (e.g., using PCR) any gene disclosed herein.

In certain exemplary embodiments of the invention, a detection reagent is an isolated or synthetic DNA or RNA polynucleotide probe or primer or PNA oligomer, or a combination of DNA, RNA and/or PNA, that hybridizes to a segment of a target nucleic acid molecule corresponding to any of the genes/transcripts disclosed in Tables 2 and 30. A detection reagent in the form of a polynucleotide may optionally contain modified base analogs, intercalators or minor groove binders. Multiple detection reagents such as probes may be, for example, affixed to a solid support (e.g., arrays or beads) or supplied in solution (e.g., probe/primer sets for enzymatic reactions such as PCR, RT-PCR, TaqMan assays, or primer-extension reactions) to form an expression profiling kit.

A probe or primer typically is a substantially purified oligonucleotide or PNA oligomer. Such oligonucleotide typically comprises a region of complementary nucleotide sequence that hybridizes under stringent conditions to at least about 8, 10, 12, 16, 18, 20, 22, 25, 30, 40, 50, 55, 60, 65, 70, 80, 90, 100, 120 (or any other number in-between) or more consecutive nucleotides in a target nucleic acid molecule.

Other preferred primer and probe sequences can readily be determined using the nucleotide sequences of genes/transcripts disclosed in Tables 2 and 30. It will be apparent to one of skill in the art that such primers and probes are directly useful as reagents for expression profiling of the genes/transcripts disclosed herein, and can be incorporated into any kit/system format.

In order to produce a probe or primer specific for a target gene/transcript sequence, the gene/transcript sequence is typically examined using a computer algorithm which starts at the 5' or at the 3' end of the nucleotide sequence. Typical algorithms will then identify oligomers of defined length that are unique to the gene/transcript sequence, have a GC content within a range suitable for hybridization, lack predicted secondary structure that may interfere with hybridization, and/or possess other desired characteristics or that lack other undesired characteristics.

A primer or probe of the present invention is typically at least about 8 nucleotides in length. In one embodiment of the invention, a primer or a probe is at least about 10 nucleotides in length. In a preferred embodiment, a primer or a probe is at least about 12 nucleotides in length. In a more preferred embodiment, a primer or probe is at least about 16, 17, 18, 19, 20, 21, 22, 23, 24 or 25 nucleotides in length. While the maximal length of a probe can be as long as the target sequence to be detected, depending on the type of assay in which it is employed, it is typically less than about 50, 60, 65, or 70 nucleotides in length. In the case of a primer, it is typically less than about 30 nucleotides in length. In a specific preferred embodiment of the invention, a primer or a probe is within the length of about 18 and about 28 nucleotides. However, in other embodiments, such as nucleic acid arrays and other embodiments in which probes are affixed to a substrate, the probes can be longer, such as on the order of 30-70, 75, 80, 90, 100, or more nucleotides in length.

Exemplary embodiments of the present invention encompass nucleic acid analogs that contain modified, synthetic, or non-naturally occurring nucleotides or structural elements or other alternative/modified nucleic acid chemistries known in the art. Such nucleic acid analogs are useful, for example, as detection reagents (e.g., primers/probes) for detecting one or more of the genes/transcripts identified in Tables 2 and 30. Furthermore, kits/systems (such as beads, arrays, etc.) that include these analogs are also encompassed by the present invention. For example, PNA oligomers can be based on polymorphic sequence variants of the genes/transcripts disclosed herein. PNA oligomers are analogs of DNA in which the phosphate backbone is replaced with a peptide-like backbone (Lagriffoul et al., *Bioorganic & Medicinal Chemistry Letters* 4:1081-1082 [1994], Petersen et al., *Bioorganic & Medicinal Chemistry Letters* 6:793-796 [1996], Kumar et al., *Organic Letters* 3[9]:1269-1272 [2001], WO96/04000). PNA hybridizes to complementary RNA or DNA with higher affinity and specificity than conventional oligonucleotides and oligonucleotide analogs. The properties of PNA enable novel molecular biology and biochemistry applications unachievable with traditional oligonucleotides and peptides.

Additional examples of nucleic acid modifications that improve the binding properties and/or stability of a nucleic acid include the use of base analogs such as inosine, intercalators (U.S. Pat. No. 4,835,263) such as ethidium bromide and SYBR® Green, and the minor groove binders (U.S. Pat. No. 5,801,115). Thus, references herein to nucleic acid molecules, expression profiling reagents (e.g., probes and primers), and oligonucleotides/polynucleotides include PNA oligomers and other nucleic acid analogs. Other examples of nucleic acid analogs and alternative/modified nucleic acid chemistries known in the art are described in *Current Protocols in Nucleic Acid Chemistry*, John Wiley & Sons, New York (2002).

While the design of each allele-specific primer or probe depends on variables such as the precise composition of the nucleotide sequences in a target nucleic acid molecule and the length of the primer or probe, another factor in the use of primers and probes is the stringency of the conditions under which the hybridization between the probe or primer and the target sequence is performed. Higher stringency conditions utilize buffers with lower ionic strength and/or a higher reaction temperature, and tend to require a closer match between the probe/primer and target sequence in order to form a stable duplex. If the stringency is too high, however, hybridization may not occur at all. In contrast, lower stringency conditions utilize buffers with higher ionic strength and/or a lower reaction temperature, and permit the formation of stable duplexes with more mismatched bases between a probe/primer and a target sequence. By way of example but not limitation, exemplary conditions for high-stringency hybridization conditions using an allele-specific probe are as follows: prehybridization with a solution containing 5× standard saline phosphate EDTA (SSPE), 0.5% $NaDodSO_4$ (SDS) at 55° C., and incubating probe with target nucleic acid molecules in the same solution at the same temperature, followed by washing with a solution containing 2×SSPE, and 0.1% SDS at 55° C. or room temperature.

Moderate-stringency hybridization conditions may be used for primer extension reactions with a solution containing, e.g., about 50 mM KCl at about 46° C. Alternatively, the reaction may be carried out at an elevated temperature such as 60° C. In another embodiment, a moderately-stringent hybridization condition is suitable for oligonucleotide ligation assay (OLA) reactions, wherein two probes are ligated if they are completely complementary to the target sequence, and may utilize a solution of about 100 mM KCl at a temperature of 46° C.

In a hybridization-based assay, specific probes can be designed that hybridize to a segment of target DNA of one gene/transcript sequence but do not hybridize to sequences from other genes/transcripts. Hybridization conditions should be sufficiently stringent that there is a significant detectable difference in hybridization intensity between genes, and preferably an essentially binary response, whereby a probe hybridizes to only one of the gene sequences or significantly more strongly to one gene sequence. While a probe may be designed to hybridize to a target sequence of a specific gene such that the target site aligns anywhere along the sequence of the probe, the probe is preferably designed to hybridize to a segment of the target sequence such that the gene sequence aligns with a central position of the probe (e.g., a position within the probe that is at least three nucleotides from either end of the probe). This design of probe generally achieves good discrimination in hybridization between different genes.

Oligonucleotide probes and primers may be prepared by methods well known in the art. Chemical synthetic methods include, but are not limited to, the phosphotriester method described by Narang et al., *Methods in Enzymology* 68:90 [1979]; the phosphodiester method described by Brown et al., *Methods in Enzymology* 68:109 [1979], the diethylphosphoamidate method described by Beaucage et al., *Tetrahedron Letters* 22:1859 [1981]; and the solid support method described in U.S. Pat. No. 4,458,066. In the case of an array, multiple probes can be immobilized on the same support for simultaneous analysis of multiple different gene/transcript sequences.

In one type of PCR-based assay, a gene-specific primer hybridizes to a region on a target nucleic acid molecule that overlaps a gene sequence and only primes amplification of the gene sequence to which the primer exhibits perfect complementarity (Gibbs, *Nucleic Acid Res.* 17:2427-2448 [1989]). Typically, the primer's 3'-most nucleotide is aligned with and complementary to the target nucleic acid molecule. This primer is used in conjunction with a second primer that hybridizes at a distal site. Amplification proceeds from the two primers, producing a detectable product that indicates which gene/transcript is present in the test sample. This PCR-based assay can be utilized as part of the TaqMan assay, described below.

The genes in the 14-gene signature described herein, as well as PR, can be detected by any one of a variety of nucleic acid amplification methods, which are used to increase the copy numbers of a polynucleotide of interest in a nucleic acid sample. Such amplification methods are well known in the art, and they include but are not limited to, polymerase chain reaction (PCR) (U.S. Pat. Nos. 4,683,195 and 4,683,202; *PCR Technology: Principles and Applications for DNA Amplification*, ed. H. A. Erlich, Freeman Press, New York, N.Y. [1992]), ligase chain reaction (LCR) (Wu and Wallace, *Genomics* 4:560 [1989]; Landegren et al., *Science* 241:1077 [1988]), strand displacement amplification (SDA) (U.S. Pat. Nos. 5,270,184 and 5,422,252), transcription-mediated amplification (TMA) (U.S. Pat. No. 5,399,491), linked linear amplification (LLA) (U.S. Pat. No. 6,027,923), and the like, and isothermal amplification methods such as nucleic acid sequence based amplification (NASBA), and self-sustained sequence replication (Guatelli et al., *Proc. Natl. Acad. Sci. USA* 87: 1874 [1990]). Based on such methodologies, a person skilled in the art can readily design primers in any suitable regions 5' and 3' of the gene/transcript sequences of interest, so as to amplify the genes/transcripts disclosed herein. Such primers may be used to reverse-transcribe and amplify DNA of any length, such that it contains the gene/transcript of interest in its sequence.

Generally, an amplified polynucleotide is at least about 16 nucleotides in length. More typically, an amplified polynucleotide is at least about 20 nucleotides in length. In a preferred embodiment of the invention, an amplified polynucleotide is at least about 30 nucleotides in length. In a more preferred embodiment of the invention, an amplified polynucleotide is at least about 32, 40, 45, 50, or 60 nucleotides in length. In yet another preferred embodiment of the invention, an amplified polynucleotide is at least about 100, 200, 300, 400, or 500 nucleotides in length. While the total length of an amplified polynucleotide of the invention can be as long as an exon, an intron or the entire gene, an amplified product is typically up to about 1,000 nucleotides in length (although certain amplification methods may generate amplified products greater than 1,000 nucleotides in length). More preferably, an amplified polynucleotide is not greater than about 150-250 nucleotides in length.

In certain exemplary embodiments of the invention, a gene expression profiling reagent of the invention is labeled with a fluorogenic reporter dye that emits a detectable signal. While a preferred reporter dye is a fluorescent dye, any reporter dye that can be attached to a detection reagent such as an oligonucleotide probe or primer is suitable for use in the invention. Such dyes include, but are not limited to, Acridine, AMCA, BODIPY, Cascade Blue, Cy2, Cy3, Cy5, Cy7, Dabcyl, Edans, Eosin, Erythrosin, Fluorescein, 6-Fam, Tet, Joe, Hex, Oregon Green, Rhodamine, Rhodol Green, Tamra, Rox, and Texas Red.

In yet another embodiment of the invention, the detection reagent may be further labeled with a quencher dye such as Tamra, especially when the reagent is used as a self-quenching probe such as a TaqMan (U.S. Pat. Nos. 5,210,015 and 5,538,848) or Molecular Beacon probe (U.S. Pat. Nos. 5,118,801 and 5,312,728), or other stemless or linear beacon probe (Livak et al., *PCR Method Appl.* 4:357-362 [1995]; Tyagi et al., *Nature Biotechnology* 14:303-308 [1996]; Nazarenko et al., *Nucl. Acids Res.* 25:2516-2521 [1997]; U.S. Pat. Nos. 5,866,336 and 6,117,635).

The detection reagents of the invention may also contain other labels, including but not limited to, biotin for streptavidin binding, hapten for antibody binding, and oligonucleotide for binding to another complementary oligonucleotide such as pairs of zipcodes.

Gene Expression Kits and Systems

A person skilled in the art will recognize that, based on the gene and sequence information disclosed herein, expression profiling reagents can be developed and used to assay any genes/transcripts disclosed herein either individually or in combination, and such detection reagents can be readily incorporated into one of the established kit or system formats which are well known in the art. The terms "kits" and "systems," as used herein in the context of gene expression profiling reagents, are intended to refer to such things as combinations of multiple gene expression profiling reagents, or one or more gene expression profiling reagents in combination with one or more other types of elements or components (e.g., other types of biochemical reagents, containers, packages such as packaging intended for commercial sale, substrates to which gene expression profiling reagents are attached, electronic hardware components, etc.). Accordingly, exemplary embodiments of the present invention further provide gene expression profiling kits and systems, including but not limited to, packaged probe and primer sets (e.g., TaqMan probe/primer sets), arrays/microarrays of nucleic acid molecules, and beads that contain one or more probes, primers, or other detection reagents for profiling one or more genes/transcripts disclosed herein. The kits/systems can optionally include various electronic hardware components; for example, arrays ("DNA chips") and microfluidic systems ("lab-on-a-chip" systems) provided by various manufacturers typically comprise hardware components. Other kits/systems (e.g., probe/primer sets) may not include electronic hardware components, but may be comprised of, for example, one or more gene expression profiling reagents (along with, optionally, other biochemical reagents) packaged in one or more containers.

In some embodiments, a gene expression profiling kit typically contains one or more detection reagents and other components (e.g., a buffer, enzymes such as reverse transcriptase, DNA polymerases or ligases, reverse transcription and chain extension nucleotides such as deoxynucleotide triphosphates, and in the case of Sanger-type DNA sequencing reactions, chain terminating nucleotides, positive control sequences, negative control sequences, and the like) necessary to carry out an assay or reaction, such as reverse transcription, amplification and/or detection of a gene-containing nucleic acid molecule. A kit may further contain means for determining the amount of a target nucleic acid, and means for comparing the amount with a standard, and can comprise instructions for using the kit to detect the gene-containing nucleic acid molecule of interest. In certain exemplary embodiments of the present invention, kits are provided which contain the necessary reagents to carry out one or more assays to profile the expression of one or more of the genes/transcripts disclosed herein. In a preferred embodiment of the present invention, gene expression profiling kits/systems are in the form of nucleic acid arrays, or compartmentalized kits, including microfluidic/lab-on-a-chip systems.

Gene expression profiling kits/systems may contain, for example, one or more probes, or pairs of probes, that hybridize to a nucleic acid molecule at or near each target gene sequence position. Multiple pairs of gene-specific probes may be included in the kit/system to simultaneously assay large numbers of genes, at least one of which is a gene/transcript disclosed herein. In some kits/systems, the gene-specific probes are immobilized to a substrate such as an array or bead. For example, the same substrate can comprise gene-specific probes for detecting at least 1 or substantially all of the genes/transcripts shown in Tables 2 and 30, or any other number in between.

The terms "arrays," "microarrays," and "DNA chips" are used herein interchangeably to refer to an array of distinct polynucleotides affixed to a substrate, such as glass, plastic, paper, nylon or other type of membrane, filter, chip, or any other suitable solid support. The polynucleotides can be synthesized directly on the substrate, or synthesized separate from the substrate and then affixed to the substrate. In one embodiment, the microarray is prepared and used according to the methods described in U.S. Pat. No. 5,837,832 (Chee et al.), PCT application WO95/11995 (Chee et al.), Lockhart, D. J. et al. (*Nat. Biotech.* 14:1675-1680 [1996]) and Schena, M. et al. (*Proc. Natl. Acad. Sci.* 93:10614-10619 [1996]), all of which are incorporated herein in their entirety by reference. In other embodiments, such arrays are produced by the methods described by Brown et al., U.S. Pat. No. 5,807,522.

Nucleic acid arrays are reviewed in the following references: Zammatteo et al., "New chips for molecular biology and diagnostics," *Biotechnol. Annu. Rev.* 8:85-101 (2002); Sosnowski et al., "Active microelectronic array system for DNA hybridization, genotyping and pharmacogenomic applications," *Psychiatr. Genet.* 12(4):181-92 (December 2002); Heller, "DNA microarray technology: devices, systems, and applications," *Annu. Rev. Biomed. Eng.* 4:129-53 (2002); Epub Mar. 22 2002; Kolchinsky et al., "Analysis of SNPs and other genomic variations using gel-based chips," *Hum. Mutat.* 19(4):343-60 (April 2002); and McGall et al., "High-density genechip oligonucleotide probe arrays," *Adv. Biochem. Eng. Biotechnol.* 77:21-42 (2002).

Any number of probes, such as gene-specific probes, may be implemented in an array, and each probe or pair of probes can hybridize to a different gene sequence position. In the case of polynucleotide probes, they can be synthesized at designated areas (or synthesized separately and then affixed to designated areas) on a substrate using a light-directed chemical process. Each DNA chip can contain, for example, thousands to millions of individual synthetic polynucleotide probes arranged in a grid-like pattern and miniaturized (e.g., to the size of a dime). Preferably, probes are attached to a solid support in an ordered, addressable array.

A microarray can be composed of a large number of unique, single-stranded polynucleotides, usually either synthetic antisense polynucleotides or fragments of cDNAs, fixed to a solid support. Typical polynucleotides are preferably about 6-60 nucleotides in length, more preferably about 15-30 nucleotides in length, and most preferably about 18-25 nucleotides in length. For certain types of microarrays or other detection kits/systems, it may be preferable to use oligonucleotides that are only about 7-20 nucleotides in length. In other types of arrays, such as arrays used in conjunction with chemiluminescent detection technology, preferred probe lengths can be, for example, about 15-80 nucleotides in length, preferably about 50-70 nucleotides in length, more preferably about 55-65 nucleotides in length, and most preferably about 60 nucleotides in length. The microarray or detection kit can contain polynucleotides that cover the known 5' or 3' sequence of a gene/transcript, sequential polynucleotides that cover the full-length sequence of a gene/transcript; or unique polynucleotides selected from particular areas along the length of a target gene/transcript sequence, particularly areas corresponding to one or more genes/transcripts disclosed in Tables 2 and 30. Polynucleotides used in the microarray or detection kit can be specific to gene(s)/transcript(s) of interest (e.g., specific to a particular signature sequence within a target gene sequence, or specific to a particular gene sequence at multiple different sequence sites), or specific to variant gene(s)/transcript(s) of interest.

Hybridization assays based on polynucleotide arrays rely on the differences in hybridization stability of the probes to perfectly matched and mismatched target sequences.

In other embodiments, the arrays are used in conjunction with chemiluminescent detection technology. The following patents and patent applications, which are all herein incorporated by reference in their entirety, provide additional information pertaining to chemiluminescent detection: U.S. patent application Ser. Nos. 10/620,332 and 10/620,333 describe chemiluminescent approaches for microarray detection; U.S. Pat. Nos. 6,124,478, 6,107,024, 5,994,073, 5,981,768, 5,871, 938, 5,843,681, 5,800,999, and 5,773,628 describe methods and compositions of dioxetane for performing chemiluminescent detection; and U.S. published application US2002/0110828 discloses methods and compositions for microarray controls.

In certain exemplary embodiments of the invention, a nucleic acid array can comprise an array of probes of about 15-25 nucleotides in length. In further embodiments, a nucleic acid array can comprise any number of probes, in which at least one probe is capable of detecting one or more genes/transcripts disclosed in Tables 2 and 30, and/or at least one probe comprises a fragment of one of the gene/transcript sequences selected from the group consisting of those disclosed in Tables 2 and 30, and sequences complementary thereto, said fragment comprising at least about 8 consecutive nucleotides, preferably 10, 12, 15, 16, 18, 20, more preferably 22, 25, 30, 40, 47, 50, 55, 60, 65, 70, 80, 90, 100, or more consecutive nucleotides (or any other number in-between) and containing (or being complementary to) a sequence of a gene/transcript disclosed in Tables 2 and 30.

A polynucleotide probe can be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more polynucleotides, or any other number which lends itself to the efficient use of commercially available instrumentation.

Using such arrays or other kits/systems, exemplary embodiments of the invention provide methods of identifying and profiling expression of the genes disclosed herein in a test sample. Such methods typically involve incubating a test sample of nucleic acids with an array comprising one or more probes corresponding to at least one gene/transcript disclosed herein, and assaying for binding of a nucleic acid from the test sample with one or more of the probes. Conditions for incubating a gene expression profiling reagent (or a kit/system that employs one or more such gene expression profiling reagents) with a test sample vary. Incubation conditions depend on factors such as the format employed in the assay, the profiling methods employed, and the type and nature of the profiling reagents used in the assay. One skilled in the art will recognize that any one of the commonly available hybridization, amplification and array assay formats can readily be adapted to detect the genes/transcripts disclosed herein.

An exemplary gene expression profiling kit/system of the present invention may include components that are used to prepare nucleic acids from a test sample for the subsequent reverse transcription, RNA enrichment, amplification and/or detection of a gene sequence-containing nucleic acid molecule. Such sample preparation components can be used to produce nucleic acid extracts (including DNA, cDNA and/or RNA) from any tumor tissue source, including but not limited to, fresh tumor biopsy, frozen or foramalin-fixed paraffin embedded (FFPE) tissue specimens, or tumors collected and preserved by any method. The test samples used in the above-described methods will vary based on such factors as the assay format, nature of the profiling method, and the specific tissues, cells or extracts used as the test sample to be assayed. Methods of preparing nucleic acids are well known in the art and can be readily adapted to obtain a sample that is compatible with the system utilized. Automated sample preparation systems for extracting nucleic acids from a test sample are commercially available, and examples are Qiagen's BioRobot 9600, Applied Biosystems' PRISM 6700, and Roche Molecular Systems' COBAS AmpliPrep System.

In exemplary embodiments of the invention, the kit can be a compartmentalized kit. A compartmentalized kit includes any kit in which reagents are contained in separate containers. Such containers include, for example, small glass containers, plastic containers, strips of plastic, glass or paper, or arraying material such as silica. Such containers allow one to efficiently transfer reagents from one compartment to another compartment such that the test samples and reagents are not cross-contaminated, or from one container to another vessel not included in the kit, and the agents or solutions of each container can be added in a quantitative fashion from one compartment to another or to another vessel. Such containers may include, for example, one or more containers which will accept the test sample, one or more containers which contain at least one probe or other gene expression profiling reagent for profiling the expression of one or more genes/transcripts disclosed herein, one or more containers which contain wash reagents (such as phosphate buffered saline, Tris-buffers, etc.), and one or more containers which contain the reagents used to reveal the presence of the bound probe or other gene expression profiling reagents. The kit can optionally further comprise compartments and/or reagents for, for example, reverse transcription, RNA enrichment, nucleic acid amplification or other enzymatic reactions such as primer extension reactions, hybridization, ligation, electrophoresis (preferably capillary electrophoresis), mass spectrometry, and/or laser-induced fluorescent detection. The kit may also include instructions for using the kit. Exemplary compartmentalized kits include microfluidic devices known in the art (see, e.g., Weigl et al., "Lab-on-a-chip for drug development," *Adv. Drug Deliv. Rev.* 24, 55[3]:349-77 [February 2003]). In such microfluidic devices, the containers may be referred to as, for example, microfluidic "compartments," "chambers," or "channels."

Uses of Gene Expression Profiling Reagents

The nucleic acid molecules in Tables 3 and 30 have a variety of uses, especially in the prognosis of breast cancer metastasis. For example, the nucleic acid molecules are useful as amplification primers or hybridization probes, such as for expression profiling using messenger RNA, transcript RNA, cDNA, genomic DNA, amplified DNA or other nucleic acid molecules, and for isolating full-length cDNA and genomic clones encoding the genes/transcripts disclosed in Tables 2 and 30 as well as their orthologs.

A probe can hybridize to any nucleotide sequence along the entire length of a nucleic acid molecule. Preferably, a probe hybridizes to a region of a transcript identified in Tables 2 or 30. More preferably, a probe hybridizes to a transcript in a sequence-specific manner such that it distinguishes the target transcript from other nucleic acid molecules which vary from the target transcript. Such a probe is particularly useful for detecting the presence of an expressed transcript in a test sample.

Thus, the nucleic acid molecules of the invention can be used as hybridization probes, as well as reverse transcription and/or amplification primers, to detect and profile the expression levels of the genes/transcripts disclosed herein, thereby determining the probability of whether an individual with breast cancer having a particular expression profile is at risk for distant metastasis. Expression profiling of disclosed genes/transcripts provides a prognostic tool for distant metastasis.

Generation of the Metastasis Score (MS)

Expression levels of the 14 genes disclosed in Table 2 can be used to derive a metastasis score (MS) predictive of metastasis risk. The MS can be combined with expression of progesterone receptor (PR), and weighted coefficients can be applied to each of MS and PR, to determine a composite metastasis score (cMS) as described herein. Expression levels may be calculated by the $\Delta(\Delta C_t)$ method, where Ct=the threshold cycle for target amplification; i.e., the cycle number in PCR at which time exponential amplification of target begins. (Livak et al., *Methods* 2001, 25:402-408). The level of mRNA of each of the 14 profiled genes may be defined as:

$$\Delta(\Delta Ct) = (Ct_{GOI} - Ct_{EC})_{test\,RNA} - (Ct_{GOI} - Ct_{EC})_{ref\,RNA}$$

where GOI=gene of interest (e.g., each of the 14 signature genes of the MS), test RNA=RNA obtained from the patient sample, ref RNA=a calibrator reference RNA, and EC=an endogenous control. The expression level of each signature gene may be first normalized to the three endogenous control genes, listed in Table 2 (EC). A Ct representing the average of the Cts obtained from amplification of the three endogenous controls ($Ct_{EC}$) can be used to minimize the risk of normalization bias that would occur if only one control gene were used (T. Suzuki, P J Higgins et al., 2000, *Biotechniques* 29:332-337). Primers that may preferably be used to amplify the endogenous control genes are listed in Table 3; but primers possible for amplifying these endogenous controls are not limited to these disclosed oligonucleotides. The adjusted expression level of the gene of interest may be further normalized to a calibrator reference RNA pool, ref RNA (universal human reference RNA, Stratagene, La Jolla, Calif.). This can be used to standardize expression results obtained from various machines.

The Δ(ΔCt) value, obtained in gene expression profiling for each of the 14 signature genes, may be used in the following formula to generate a metastasis score (MS):

$$MS_u = -\left[\sum_{i=1}^{14} Gi\right]$$

(MS$_u$ indicates an un-scaled MS)

Alternatively, the Δ(ΔCt) value, obtained in gene expression profiling for each of the 14 signature genes, may be used in the following formula to generate a metastasis score (MS):

$$MS = a0 + \sum_{i=1}^{M} ai * Gi$$

in which Gi represents the expression level of each gene (i) of the 14-gene prognostic signature. The value of Gi is the Δ(ΔCt) obtained in expression profiling described above. An exemplary constant ai for each gene i is provided in Table 2. The constant a0 can be 0.022; this centers the MS so that its median value is zero. M is the number of genes in the component list; in this case 14. Thus, the MS is a measure of the summation of expression levels for the 14 genes disclosed in Table 2, each multiplied by a particular constant ai, also in Table 2, and finally this summation can be added to the centering constant 0.022 to derive the MS.

Alternatively, the Δ(ΔCt) value, obtained in gene expression profiling for each of the 14 signature genes, may be used in the following formula to generate a metastasis score (MS):

$$MS = a0 + b * \sum_{i=1}^{M} ai * Gi$$

in which Gi represents the standardized expression level of each gene (i) of the 14-gene prognostic signature. The value of Gi is obtained by subtracting the mean gene expression from the original expression level measured in Δ(ΔCt) obtained in expression profiling described above and then divided by the standard deviation of the gene expression in the training set. An exemplary constant ai for each gene i is provided in Table 2. The constant b can be −0.251 (derived from a univariate Cox model with the principal component as a predictor, to get the correct sign and scaling). The constant a0 can be 0.022; this centers the MS so that its median value is zero. M is the number of genes in the component list; in this case 14. Thus, the MS is a measure of the summation of expression levels for the 14 genes disclosed in Table 2, each multiplied by a particular constant ai, also in Table 2. This summation is multiplied by a constant b, and the centering constant 0.022 can then be added to derive the MS.

Any new sample may be evaluated by generating this metastasis score from the 14-gene expression profiling data for that patient, and from this score the probability of distant metastasis for the patient can be determined.

Note that the MS can be simply a sum of the values of Δ(ΔCt) as described above, in which case the formula of the MS is simplified by substituting the value of a0 with zero, and the constant ai is one.

Note that the MS can also be simply a sum of the values of Δ(ΔCt) as described above, then multiplied by the constant −0.04778 for correct sign and scaling such that distant metastasis risk increases with increase of MS. Finally, the constant 0.8657 can be added so that the mean of MS is zero. MS derived in this alternative way will have equal weighting of all 14 genes. The risk of distant metastasis would increase as MS increases. The two different metastasis scores described here have very high correlation with Pearson correlation coefficient greater than 0.999.

Generation of Distant Metastasis Probability from MS

The probability of distant metastasis for any individual patient can be calculated from the MS at variable time points, using the Weibull distribution as the baseline survival function.

The MS, as obtained above, can be converted into the probability of distant metastasis by means of the Cox proportional hazard model. Because the Cox model does not specify the baseline hazard function, the hazard and survivor functions can first be constructed through parametric regression models. In the parametric regression models, distant metastasis-free survival (DMFS) time can be the outcome, and the MS can be the independent variable input. The event time can be assumed to have a Weibull distribution; its two parameters can be estimated using the survival data from which the MS was derived. To calculate the probability of distant metastasis within a certain time for a patient, the MS value can be simply substituted into the formula for the survivor function.

Clinical Application of the Metastasis Score (MS) in Risk Determination

One way of using the MS in determining the risk for metastasis is to generate one or more MS Threshold, also known as MS "cut-point" or "cutoff". Such MS Threshold can be used as a benchmark when compared to the MS of a breast cancer patient so as to determine whether such patient has either an increased or decreased risk for metastasis. MS Threshold can be determined by different methods and can be different for different definitions of MS. For MS defined in Equation 1 that was used in Examples 1, 2, and 3, MS Threshold was determined from hazard ratios of high-risk vs. low-risk groups. Kaplan-Meier (KM) curves for distant metastasis-free survival are generated for the high- and low-risk patient groups defined by MS cut points. The choice of median MS as cut point can be based upon the calculation of the hazard ratios of the high vs. low-risk groups using different cut points from ten percentile of MS to ninety percentile of MS. The median cut point can be defined as the point where there are an equal number of individuals in the high and low-risk groups, and is found to produce near the highest hazard ratio in the training samples as described in Example 1. Hazard ratios (HR) and 95% confidence intervals (CI) using the cut point of median MS can be calculated and reported. Log rank tests can be performed, and the hazard ratios can be calculated for different cut points. The accuracy and value of the 14-gene signature in predicting distant metastasis at five years can be assessed by various means (X H Zhou, N. Obuchowski et al., eds., 2002, *Statistical Methods in Diagnostic Medicine*, Wiley-Interscience, New York). For MS defined in Equation 2 that was used in Examples 4 and 5, MS Threshold was determined from sensitivity and specificity of MS to predict distant metastasis in 5 years in samples from Guy's Hospital as described in Example 2. Two MS cut points can be chosen such that the sensitivity of MS to predict distant metastasis in 5 years is over 90% if the first cut point is used. The second cut point can be chosen such that the sensitivity and specificity of MS to predict distant metastasis in 5 years will both be at 70%. For MS defined in Equation 2, the first MS Threshold can be −0.1186 and the second MS Threshold can be 0.3019. With two MS cut points, there are high, intermediate, and low MS groups. In treated samples from Guy's Hospital and treated samples from Aichi Cancer Center in Japan, the high MS group was designated as the high-risk group and the intermediate and low MS groups were designated as the low-risk group.

Progesterone Receptor (PR)

Calculation of Progesterone Receptor (PR) mRNA Expression Levels and PR Status

In certain exemplary embodiments, expression levels of the genes disclosed herein, such as the progesterone receptor gene (PGR), can be calculated by the $\Delta(\Delta C_t)$ method (interchangeably referred to as the $\Delta\Delta C_T$ method; see Livak et al., Methods 2001, 25:402-408), where Ct=the threshold cycle for target amplification; i.e., the cycle number in PCR at which time exponentional amplification of target begins (Livak et al., Methods 2001, 25:402-408). The level of mRNA of each of the profiled genes may be defined as:

$$\Delta(\Delta Ct) = (-1) \times (Ct_{GOI} - Ct_{EC})_{test\,RNA} - (Ct_{GOI} - Ct_{EC})_{ref\,RNA}$$

where GOI=gene of interest (e.g., PGR), test RNA=RNA obtained from the patient sample, ref RNA=a calibrator reference RNA, and EC=an endogenous control (e.g., NUP214, PPIG, and/or SLU7). The expression level of each gene to be detected (e.g., PGR) may be first normalized to one or more endogenous control genes, such as any or all of the housekeeping ("HSK") genes NUP214, PPIG, and SLU7. A Ct representing the average of the Cts obtained from amplification of multiple endogenous controls ($Ct_{EC}$), such as any two or all three of NUP214, PPIG, and SLU7, can be used to minimize the risk of normalization bias that may occur if only one control gene were used (T. Suzuki, P J Higgins et al., 2000, Biotechniques 29:332-337). Exemplary primers that may be used to amplify the endogenous control genes are provided in Table 3 (but primers for amplifying these endogenous control genes are not limited to these disclosed oligonucleotides). The adjusted expression level of the gene(s) of interest may be further normalized to a calibrator reference RNA pool, such as ref RNA (Universal Human Reference RNA, Stratagene, La Jolla, Calif.), or other control sample. This can be used to standardize expression results obtained from various machines.

The $\Delta(\Delta C_t)$ method (which is interchangeably referred to as $\Delta\Delta C_T$) is described in, for example, Livak et al., Methods 2001, 25:402-408. $\Delta\Delta C_T$ values calculated from PGR expression levels can be applied to classify the expression levels of this gene as "positive" or "negative" with respect to PR status. For example, $\Delta\Delta C_T$ cutoff points can be selected and used to classify $\Delta\Delta C_T$ values for PGR expression levels that are above (or equal to) the cutoff as "positive" with respect to PR status, and/or to classify $\Delta\Delta C_T$ values for PGR expression levels that are below (or equal to) the cutoff as "negative" with respect to PR status. Alternatively, various clustering methods based on $\Delta\Delta C_T$ can be employed for the same purposes. Clustering methods are described in, for example, Fraley et al., J Am Stat Assoc 2002, 97:611-631, Fraley et al., J Class 1999, 16:297-306, and Ma et al., J Clin Oncol 2006, 24: 4611-4619.

A wide variety of statistical methods and thresholds can be used for determining or classifying PR status from mRNA expression levels of this gene. See Dudoit et al., "Classification in Microarray Experiments", Statistical Analysis of Gene Expression Microarray Data, 2003, Chapman & Hall/CRC: 93-158, incorporated herein by reference in its entirety, for examples of methods known in the art for classifying gene expression data.

For example, with respect to threshold levels, a wide variety of cut-offs can be employed for classifying the status of a gene, such as classifying PR status as positive or negative. Methods for selecting or formulating these cut-offs are known in the art and/or can be implemented by one of ordinary skill in the art. For classifying the expression status of a given gene, various discrete "cutoffs" or continuous classification systems can be applied. For example, the classification of PR status as positive or negative can be accomplished using a variety of methods. Certain methods may involve using a set of training data to produce a model that can then be used to classify the status of test samples. For example, positive/negative cutoffs can be selected by manual inspection of a training data set, and these cutoffs can be applied to classifying test samples. As an example, a test sample in which expression of a given gene (e.g., PGR), which may be indicated by $\Delta\Delta C_T$ or other statistical methods, is above (or equal to) a pre-determined cutoff can be classified as "positive" whereas a test sample in which expression of the gene is below (or equal to) the pre-determined cutoff can be classified as "negative". Thus, the cutoff can be used as a benchmark when compared to the expression level of a given gene (e.g., PGR) in a breast cancer patient, such as to classify the status of that gene (e.g., as "positive" or "negative" with respect to PR status). This status can then be used, for example, by a medical practitioner to formulate or select a treatment strategy or therapeutic agent best suited for the breast cancer patient.

$\Delta\Delta C_T$ and clustering methods, as well as the thresholds (e.g., cutoffs) employed for classifying gene status, are merely exemplary statistical methods, and one of ordinary skill in the art will appreciate that many alternative statistical methods, classification systems, and thresholds can be employed, particularly to determine PR status from the mRNA expression levels of this gene. The results of mRNA expression analysis of breast cancer specimens can be used as training data to develop various classification methods, such as a cutoff point method (cutoffs can be selected based on IHC Allred scores) and a clustering method (which can classify PR status independent of IHC Allred scores), which can then validated in further sample sets. The $\Delta\Delta C_T$ values for PR in various breast tumor samples can be calculated. Using these $\Delta\Delta C_T$ values in the cutoff point method, PR status can be classified using $\Delta\Delta C_T$ cutoff points and the PR status can be classified as positive if $\Delta\Delta C_T$ is greater than or equal to the cutoff point. Using these $\Delta\Delta C_T$ values in the clustering method to classify PR status, a Gaussian mixture model (e.g., as implemented in MCLUST software) can be employed to define clusters of subjects based on PR $\Delta\Delta C_T$ measurements. The mixture models estimated from the training data can then be used to assign test subjects to the cluster for which they have the highest probability of membership based on their $\Delta\Delta C_T$ measurements.

Clustering Methods

As an alternative to the $\Delta\Delta C_T$ cutoff-point method, clustering methods can also be used for classifying samples with respect to PR status.

As an example, parameters for PR can be derived from discovery sample sets using Gaussian mixture modeling (e.g., implemented in MCLUST software) ("R: A Language and Environment for Statistical Computing", R Development Core Team, R Foundation for Statistical Computing; Banfield et al., Biometrics 1993, 49:803-821; Fraley et al., J Class 1999, 16:297-306; Fraley et al., Technical Report No. 415, Dept. of Statistics, Univ. of Washington, October 2002; Fraley et al.,. J Am Stat Assoc 2002, 97:611-631; and Fraley et al., J Class 2003, 20:263-286). Parameters can be used with π value and $\Delta\Delta C_T$ to calculate probability and confidence for classifying a sample, such as in the following example (estrogen receptor (ER) is indicated in place of PR in the following example equations):

1) Calculate Probability:

$$py_{ER-} = \frac{e^{\frac{-(\Delta\Delta C_T - U_{ER-})^2}{2 \times V_{ER-}}}}{\sqrt{2\pi \times V_{ER-}}}$$

$$py_{ER+} = \frac{e^{\frac{-(\Delta\Delta C_T - U_{ER+})^2}{2 \times V_{ER+}}}}{\sqrt{2\pi \times V_{ER+}}}$$

$\pi$=3.1415926535 and e=2.71828182845905

2) Determine Confidence:

$$Z_{ER-} = \frac{py_{ER-} \times p_{ER-}}{(py_{ER-} \times p_{ER-}) + (py_{ER+} \times p_{ER+})}$$

$$Z_{ER+} = \frac{py_{ER+} \times p_{ER+}}{(py_{ER-} \times p_{ER-}) + (py_{ER+} \times p_{ER+})}$$

3) Classification of Status:

ER+=$z_{ER+} \geq z_{ER-}$

ER−=$z_{ER+} \leq z_{ER-}$

Uncertainty of ER+=$1-z_{ER+}$
Uncertainty of ER−=$1-z_{ER-}$

Exemplary parameter values that could be used for PR in the above equations for clustering analysis (substituting these PR values in place of ER in the above equations) are as follows.

For prior probabilities: $p_{PR-}$=0.3633805; $p_{PR+}$=0.6366195
For means: $U_{PR-}$=−0.7653664; $U_{PR+}$=3.9643629
For variance: $V_{PR-}$=3.679639; $V_{PR+}$=3.679639

Absolute Quantitation Methods

In addition to relative quantitation methods, absolute quantitation methods can also be used for classifying samples with respect to PR status.

Absolute quantitation methods can optionally be done without using a control sample (such as for monitoring experiment-to-experiment variation).

In absolute quantitation methods, the expression level of PR in a sample can optionally be normalized with the expression level of one or more control genes (such as any or all of the housekeeping genes NUP214, PPIG, and $SLU_7$), such as follows:

$\Delta C_{T\ sample} = C_T$ of gene of interest−$C_T$ of HSK genes

EXAMPLES

The following examples are offered to illustrate, but not to limit the claimed invention.

Example One

The mRNA Expression Levels of a 14-Gene Prognostic Signature Predict Risk for Distant Metastasis in 142 Lymph Node-Negative, ER-Positive Breast Cancer Patients The following example illustrates how a 14-gene prognostic signature was identified and how it can be used in determining prognosis for distant metastasis in breast cancer patients, even in routine clinical laboratory testing. A clinician can perform mRNA expression profiling on the 14 genes described herein, using RNA obtained from a number of means such as biopsy, FFPE, frozen tissues, etc., and then insert the expression data into an algorithm provided herein to determine a prognostic metastasis score.

FFPE tissue sections obtained from node-negative, ER-positive breast cancer patients were used in the example described below. An initial set of 200 genes were analyzed to derive the final 14-gene signature. Included as candidate genes for this signature were genes previously reported in the literature. Also in this example, the extent of overlap of this signature with routinely used prognostic factors and tools was determined.

Tumors from node-negative, ER-positive patients were selected for this study because prognostic information for node-negative patients would be of great value in guiding treatment strategies. Also, microarray studies indicate that this tumor subset is clinically distinct from other types of breast cancer tumors. (T. Sorlie, C M Perou et al., 2001, *Proc Natl Acad Sci USA* 98:10869-10874; C. Sotiriou, S Y Neo et al., 2003, *Proc Natl Acad Sci USA* 100:10393-10398). Genes were chosen for expression profiling from the gene signatures reported by H. Dai (H. Dai, L J van't Veer et al., 2005, *Cancer Res* 15:4059-4066), L J van't Veer (L J van't Veer, H. Dai et al., 2002, *Nature* 415:530-536), and S P Paik (S P Paik, S. Shak et al., 2004, *N Engl J Med* 351:2817-2826), in FFPE sections to determine the robustness of these genes and the extent to which routinely collected and stored clinical samples could be used for prognosis of metastasis. From the gene expression data a metastasis score was developed to estimate distant metastasis probability in individual patients for any timeframe.

Patients and Samples

A total of 142 node-negative, ER-positive patients with early stage breast cancer were selected, all from patients untreated with systemic adjuvant therapy (Training samples in Table 1). By limiting the study to a subset of breast cancer cases, a molecular signature was identified with a more compelling association with metastasis, more robust across different sample sets, and comprising a smaller number of genes so as to better facilitate translation to routine clinical practice. The mean age of the patients was approximately 62 years (ranging from 31-89 years).

A highly-characterized breast tumor sample set served as the source of samples for this study; the set accrued from 1975 to 1986 at the California Pacific Medical Center (CPMC). The inclusion criteria for the primary study included samples from tumors from patients who were lymph-node negative, had received no systemic therapy, and received follow-up care for eight years.

Samples were approved for use in this study by the respective institutional medical ethics committees. Patients providing samples were classified as ER-positive based on a measurement of the expression level of the ESR1 gene. Expression level of the ESR1 gene correlates well with an individual's ER status (M. Cronin, M. Pho et al. 2004, *Am J Pathol* 164(1):35-42; J M Knowlden, J M Gee et al., 1997, *Clin Cancer Res* 3:2165-2172).

Distant metastasis-free survival was chosen as the primary endpoint because it is most directly linked to cancer-related death. A secondary endpoint was overall survival.

Sample Processing

Four 10 µm sections from each paraffin block were used for RNA extraction. The tumor regions were removed based on a guide slide where the cancer cell areas have been marked by a pathologist, and the RNA extracted using Pinpoint Slide RNA Isolation System II (Zymo Research, Orange Calif.).

The yields of total RNA varied between samples. In order to increase the amount of RNA available for analysis, a T7 RNA polymerase linear amplification method was performed on the extracted RNA. RNA isolated from FFPE samples was subjected to T7-based RNA amplification using the MessageAmpII aRNA amplification kit (Ambion, Austin, Tex.).

To assess the consistency of gene expression before and after RNA amplification, a number of experiments were conducted on various genes in different samples. Amplification was first performed on RNA from 67 FFPE samples that were not a part of this study, using 0.1-100 ng of total RNA. Profiling of 20 genes was performed using the resultant enriched RNA and the original, unenriched RNA. These comparisons revealed that the fold enrichment varied from gene to gene; however, the relative expression level was consistent before and after RNA amplification in all 20 genes for 67 samples.

RNA for this study was enriched by amplification with the MessageAmpII aRNA amplification kit, as described above. Total RNA was quantified using spectrophotometric measurements ($OD_{260}$).

Gene Expression Profiling

Based on a survey of the published literature and results of microarray-based gene expression profiling experiments, 200 candidate genes were initially selected for analysis in order to determine the optimal prognostic signature. This set included genes from the 70-gene prognosis panel described by van't Veer et al. (L J van't Veer, H. Dai et al., 2002, *Nature* 415: 530-536), 104 genes analyzed by Dai et al. (H. Dai, L J van't Veer et al., 2005, *Cancer Res* 15:4059-4066), the 16-gene panel comprising the signature for response to Tamoxifen treatment reported by Paik et al. (S P Paik, S. Shak et al., 2004, *N Engl J Med* 351:2817-2826), and 24 ER-related genes as reported by West et al. (M. West, C. Blanchette et al., 2001, *Proc Natl Acad Sci USA* 98:11462-11467). Additional genes were selected as endogenous controls (EC) for normalizing expression data, according to the method described in J. Vandesompele, K. De Preter et al., *Genome Biol* 3(7): Research 0034.1-0034.11 (Epub 2002). Endogenous controls are also called "housekeeping genes" herein. Six endogenous control genes were tested for the stability of their expression levels in 150 samples of frozen breast cancer tumors. Expression data were analyzed using the geNorm program of Vandesompele et al., in which an M value was determined as a measurement of the stability of a gene's expression level. (J. Vandesompele, K. De Preter et al., *Genome Biol* 3(7): Research 0034.1-0034.11, Epub 2002). The lower the M value, the more stable the gene. Results are shown in Table 7. The M values indicated that PPIG, SLU7 and NUP214 were the most stable endogenous control genes in this sample set, with the least variation in gene expression across samples tested. The stability of these three genes was validated on 138 breast cancer tumor FFPE samples. The results are shown in Table 8.

The expression levels of the selected 200 genes, together with the three EC genes, were profiled in 142 RNA samples. For gene expression profiling, relative quantification by means of one-step reverse-transcription polymerase chain reaction (RT-PCR) was performed. Quantification was "relative" in that the expression of the target gene was evaluated relative to the expression of a set of reference, stably expressed control genes. SYBR® Green intercalating dye (Stratagene, La Jolla, Calif.) was used to visualize amplification product during real-time PCR. Briefly, the reaction mix allowed for reverse transcription of extracted sample RNA into cDNA. This cDNA was then PCR amplified in the same reaction tube, according to the cycling parameters described below. PCR conditions were designed so as to allow the primers disclosed in Table 3, upper and lower, to hybridize 5' and 3', respectively, of target sequences of the genes of interest, followed by extension from these primers to create amplification product in repetitive cycles of hybridization and extension. PCR was conducted in the presence of SYBR® Green, a dye which intercalates into double-stranded DNA, to allow for visualization of amplification product. RT-PCR was conducted on the Applied Biosystems Prism® 7900HT Sequence Detection System (Applied Biosystems, Foster City, Calif.), which detected the amount of amplification product present at periodic cycles throughout PCR, using amount of intercalated SYBR® Green as an indirect measure of product. (The fluorescent intensity of SYBR® Green is enhanced over 100-fold in binding to DNA.) PCR primers were designed so as to amplify all known splice-variants of each gene, and so that the size of all PCR products would be shorter than 150 base pairs in length, to accommodate the degraded, relatively shorter-length RNA expected to be found in FFPE samples. Primers used in the amplification of the 14 genes in the molecular signature described herein and three endogenous control genes are listed in Table 3. RT-PCR amplifications were performed in duplicate, in 384-well amplification plates. Each well contained a 15 ul reaction mix. The cycle profile consisted of: two minutes at 50° C., one minute at 95° C., 30 minutes at 60° C., followed by 45 cycles of 15 seconds at 95° C. and 30 seconds at 60° C., and ending with an amplification product dissociation analysis. The PCR components were essentially as described in L. Rogge, E. Bianchi et al., 2000, *Nat Genet* 25:96-101.

The relative changes in gene expression were determined by quantitative PCR. Expression levels were calculated by the $\Delta(\Delta C_t)$ method, where Ct=the threshold cycle for target amplification; i.e., the cycle number in PCR at which time exponentional amplification of target begins (Livak et al., *Methods* 2001, 25:402-408). The relative level of mRNA of a gene of interest was defined as:

$$\Delta(\Delta Ct)=(Ct_{GOI}-Ct_{EC})_{test\,RNA}-(Ct_{GOI}-Ct_{EC})_{ref\,RNA}$$

where GOI=gene of interest, test RNA=sample RNA, ref RNA=calibrator reference RNA, and EC=endogenous control. The expression level of every gene of interest was first normalized to the three endogenous control genes. A Ct representing the average of the three endogenous controls ($Ct_{EC}$) was used to minimize the risk of normalization bias that would occur if only one control gene was used. (T. Suzuki, P J Higgins et al., 2000, *Biotechniques* 29:332-337). Primers used to amplify the endogenous controls are listed in Table 3. The adjusted expression level of the gene of interest was further normalized to a calibrator reference RNA pool, ref RNA (universal human reference RNA, Stratagene, La Jolla, Calif.). This was used in order to standardize expression results obtained from various machines. The $\Delta(\Delta Ct)$ values obtained in expression profiling experiments of 200 genes were used in the statistical analysis described below to determine the 14-gene prognostic signature of this invention.

Determination of the 14-Gene Signature

Using data from expression profiling of the original 200 genes (i.e., the $\Delta(\Delta Ct)$ values obtained above), a semi-supervised principal component (SPC) method of determining survival time to distant metastasis was used to develop a list of genes that would comprise a prognostic signature. (E. Bair and R. Tibshirani, 2004, *PloS Biology* 2:0511-0522). SPC computation was performed using the PAM application, available online via the lab of R. Tibshirani at Standford University, Stanford, Calif. according to the method of R. Tibshirani, T J Hastie et al. 2002, *PNAS* 99:6567-6742.

Genes were first ranked according to their association with distant metastasis, using the univariate Cox proportional hazards model. Those genes with a P value<0.05 were considered significant. For any cutoff in the Cox score, SPC computed the component of genes (i.e., the principal component) that reached the optimal threshold: SPC used internal cross-validation in conjunction with a Cox model (with the principal component as the single variable) to select the optimal threshold. The first principal component gene list obtained by SPC was significant, and was used as a predictor in a univariate Cox model, in order to determine the correct sign and scaling.

The principal component gene list as produced by SPC was further reduced by the Lasso regression method. (R. Tibshirani, 1996, *J Royal Statistical Soc B*, 58:267-288). The Lasso regression was performed using the LARS algorithm. (B. Efron, T. Hastie et al., 2004, *Annals of Statistics* 32:407-499; T. Hastie, R. Tibshirani et al., eds., 2002, *The Elements of Statistical Learning*, Springer, New York). The outcome variable used in the LARS algorithm was the principal component as selected by SPC. The Lasso method selected a subset of genes that could reproduce this score with a pre-specified accuracy.

Metastasis Score

The metastasis score (MS) has the form:

$$MS = a0 + b * \sum_{i=1}^{M} ai * Gi$$

Gi represents the standardized expression level of each Lasso-derived gene (i) of the 14-gene prognostic signature. The value of Gi is calculated from subtracting the mean gene expression of that gene in the whole population from the $\Delta(\Delta Ct)$ obtained in expression profiling described above and then divided by the standard deviation of that gene. The constant ai are the loadings on the first principal component of the 14 genes listed in Table 2. The ai score for each gene i is provided in Table 2. The constant b is $-0.251$ and it was from a univariate Cox model with the principal component as a predictor, to get the correct sign and scaling. The constant a0=0.022; this centers the MS so that its median value is zero. M is the number of genes in the component list; in this case 14. Thus, the MS is a measure of the summation of expression levels for the 14 genes disclosed in Table 2, each multiplied by a particular constant ai; the summation was then multiplied by the constant b and finally, this summation added to the centering constant 0.022.

The score is herein referred to as MS (all), as it was based on an analysis of all 142 ER-positive individuals studied. Any new sample may be evaluated by generating this metastasis score from the 14-gene expression profiling data for that patient, and optionally from this score, the probability of distant metastasis for the patient can be determined.

Generation of Distant Metastasis Probability from MS

The probability of distant metastasis for any individual patient can be calculated from the MS at variable time points, using the Weibull distribution as the baseline survival function.

The metastasis score (MS) obtained above, from expression profiling of the 14-gene signature, was converted into the probability of distant metastasis by means of the Cox proportional hazard model. Because the Cox model does not specify the baseline hazard function, the hazard and survivor functions were first constructed through parametric regression models. In the parametric regression models, distant metastasis-free survival time was the outcome, and the metastasis score (MS) was the independent variable input. The event time was assumed to have a Weibull distribution; its two parameters were estimated using the survival data from which the MS was derived. To calculate the probability of distant metastasis within a certain time for a patient, the MS value is simply substituted into the formula for the survivor function.

Pre-Validation

In this study, the 142 study patients were randomly divided into ten subsets. One subset was set aside and the entire SPC procedure was performed on the union of the remaining nine subsets. Genes were selected and the prognosticator built upon the nine subsets was applied to obtain the cross-validated metastasis score, MS (CV), for the remaining subset. This cross-validation procedure was carried out 10 times until MS (CV) was filled in for all patients. By building up MS (CV) in this way, each $\frac{1}{10}^{th}$ piece did not directly use its corresponding survival times, and hence can be considered unsupervised.

This resulted in a derived variable for all the individuals in the sample, and could then be tested for its performance and compared with other clinical variables. MS (all), however, was built upon all 142 individuals tested, and would produce considerable bias if tested in the same way.

MS (CV) was used to evaluate the accuracy of the 14-gene prognostic signature when time-dependent area under ROC curve (AUC) was calculated (described below). MS (CV) was also used in the Cox regression models when the 14-gene signature was combined with clinical predictors. MS (CV) should have one degree of freedom, in contrast to the usual (non-pre-validated) predictor. The non-pre-validated predictor has many more degrees of freedom.

Statistical Analyses of the MS

Kaplan-Meier (KM) curves for distant metastasis-free and overall survival were generated for the high- and low-risk patient groups using the median of MS (CV) as the cut point (i.e., 50 percentile of MS (CV)). The choice of median MS as cut point was based upon the calculation of the hazard ratios of the high vs. low-risk groups using different cut points from ten percentile of MS to ninety percentile of MS. A balanced number of high-risk and low-risk individuals as well as near the highest hazard ratio were the determining factors for choosing the median as the cut point.

Hazard ratios (HR) and 95% confidence intervals (CI) using the cut point of median MS were calculated and reported. Log rank tests were performed, and the hazard ratios were calculated for different cut points. The accuracy and value of the 14-gene signature in predicting distant metastasis at five years were assessed by various means. (X H Zhou, N. Obuchowski et al., eds., 2002, *Statistical Methods in Diagnostic Medicine*, Wiley-Interscience, New York).

Univariate and multivariate Cox proportional hazards regressions were performed using age, tumor size, tumor grade and the 14-gene signature. Clinical subgroup analyses on the signature were also performed. Statistical analyses were performed using SAS® 9.1 statistical software (SAS Institute, Inc., Cary, N.C.), except for the statistical packages noted herein.

Multi-Gene Signature

Of the 200 candidate genes studied, 44 had unadjusted P values<0.05 in a univariate Cox proportional hazards regression. Patients with poor metastasis prognosis showed an up-regulation of 37 genes, while seven genes were down-regulated. The semi-supervised principal component procedure (SPC) in PAM yielded a prognosticator of 38 genes. The gene list was further reduced to 14 (Table 2) by using the Lasso regression, via the LARS algorithm. Table 2 provides a description of each gene. Hazard ratios (HR) at various cut points (i.e., percentile MS (CV)) were calculated. The median of MS (CV) was chosen to classify patients into low- and high-risk groups.

Results

Figure 1:
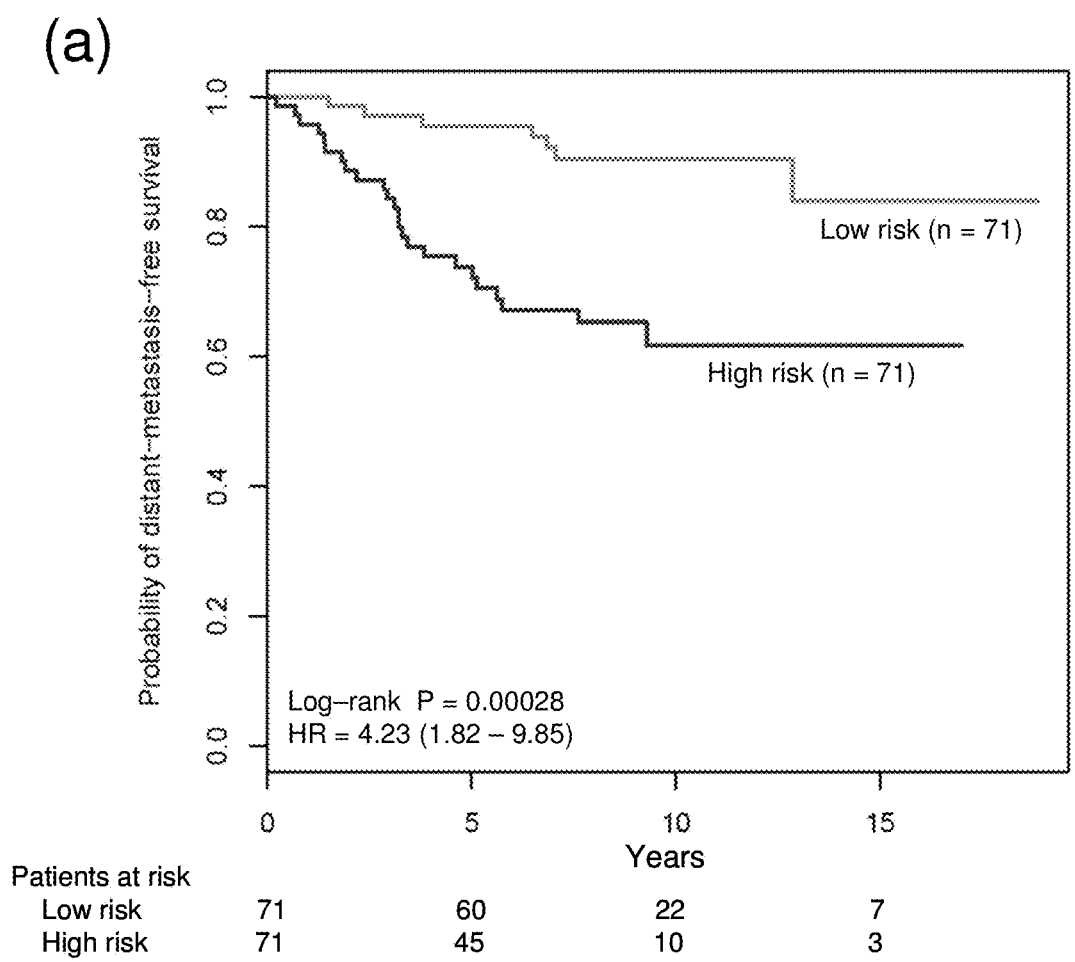
FIG. 1 shows Kaplan-Meier curves for a) time to distant metastases b) overall survival for training set from CPMC where high-risk and low-risk groups were defined by MS(CV) using zero as cut point.
Figure 1:
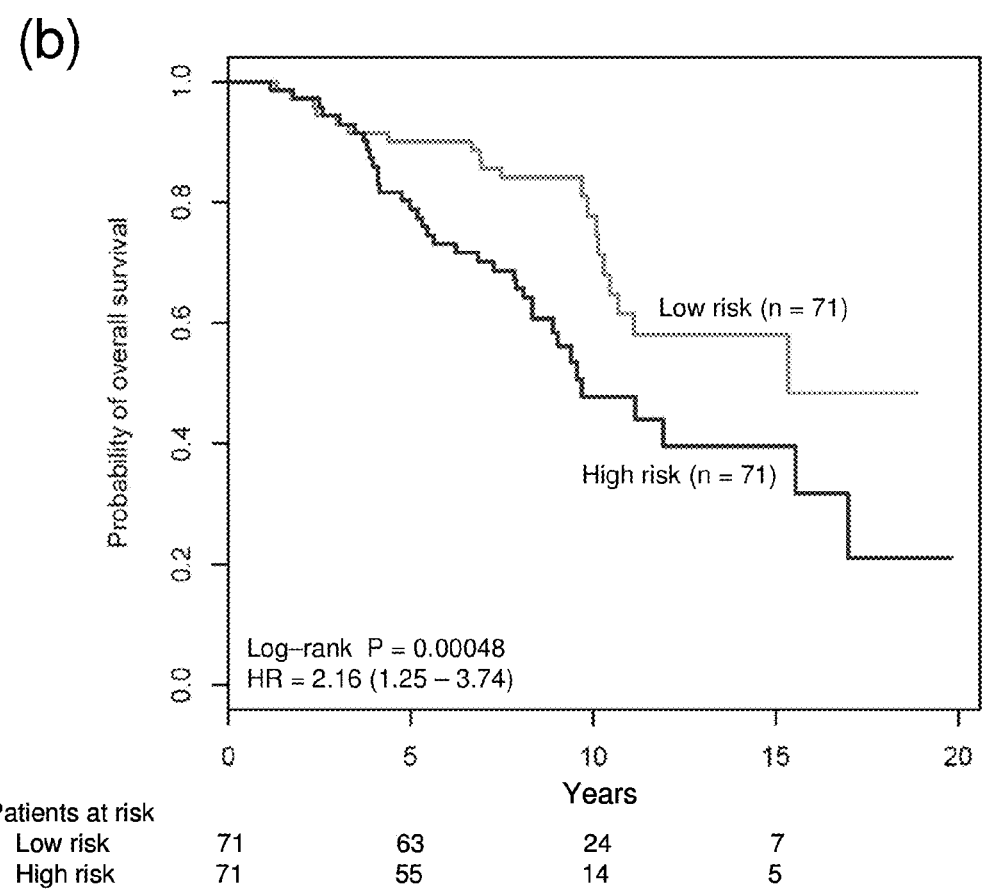

Distant-Metastasis-Free and Overall Survival Rates in Low-Risk and High-Risk Groups There were 7 and 24 distant metastases in 71 low-risk and 71 high-risk patients as defined by the median of the cross-validated Metastasis Score, MS (CV), in the training set. Kaplan Meier estimate (FIG. 1a) indicated significant differences in distant metastasis free survival (DMFS) between the two groups with a log-rank p-value of 0.00028. The 5-year and 10-year DMFS rates (standard error) in the low-risk groups were 0.96 (0.025) and 0.90 (0.037) respectively. For the high-risk group, the corresponding rates were 0.74 (0.053) and 0.62 (0.066). For overall survival (FIG. 1b), there was also significant difference between the two groups (log-rank p-value=0.0048). The 5-year and 10-year OS rates (standard error) in the low-risk groups were 0.90 (0.036) and 0.78 (0.059) while the corresponding rates were 0.79 (0.049) and 0.48 (0.070) in the high-risk group (Table 5).

Hazard Ratios from Univariate and Multivariate Cox Regression Models

The unadjusted hazard ratio of the high-risk vs. low-risk groups by MS to predict DMFS was 4.23 (95% CI=1.82 to 9.85) (Table 6) as indicated by the univariate Cox regression analysis. In comparison, the high-risk vs. low-risk groups by tumor grade (medium+high grade vs. low grade) had an unadjusted hazard ratio of 2.18 (1.04-4.59). While tumor size was significant in predicting DMFS (p=0.05) with 7% increase in hazard per cm increase in diameter, age was not a significant factor in this patient set. In the multivariate Cox regression analyses, the 14-gene molecular signature risk group had a hazard ratio of 3.26 (1.26-8.38), adjusted by age at surgery, tumor size and grade. It was the only significant risk factor (p=0.014) in the multivariate analyses.

Diagnostic Accuracy and Predictive Values

Diagnostic accuracy and predictive values of the 14-gene signature risk groups to predict distant metastases within 5 years were summarized in Table 9. Sensitivity was 0.86 for those who had distant metastases within 5 years while specificity was 0.57 for those who did not. Negative predictive value (NPV) was 96% and indicated that only 4% of individuals would have distant metastasis within 5 years when the gene signature indicated that she was in the low-risk group. Nevertheless, positive predictive value (PPV) was only 26%, indicating only 26% of individuals would develop distant metastasis while the molecular signature indicated she was high-risk. The high NPV and low PPV were partly attributed to the low prevalence of distant metastasis in 5 years, which was estimated to be 0.15 in the current patient set.

Figure 2:
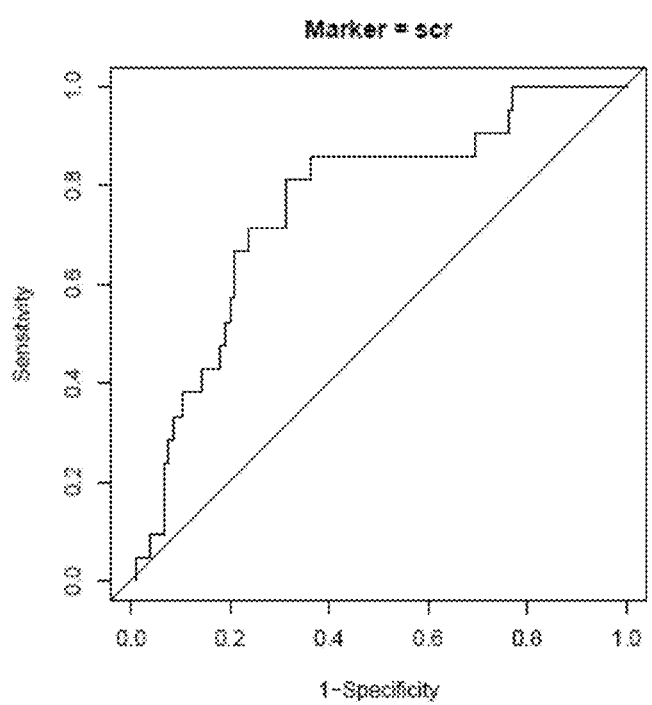
FIG. 2 is a ROC curve for predicting distant metastases by MS(CV) in 5 years in the training set from CPMC. AUC=0.76 (0.65-0.87).

Moreover, Receiver operating characteristics (ROC) curves of the continuous MS(CV) to predict distant metastases in 5 years was shown in FIG. 2. AUC was 0.76 (0.65-0.87) for predicting distant metastases in 5 years. AUC for predicting death in 10 years was 0.61 (0.49-0.73). One sided tests for AUC to be greater than 0.5 were significant with corresponding p-values of <0.0001 and 0.04 for the metastasis and death endpoints.

Discussion

Pathway analyses revealed that the 14 genes in the prognostic signature disclosed herein are involved in a variety of biological functions, but a majority of the genes are involved with cell proliferation. Eleven of the 14 genes are associated with the TP53 and TNF signaling pathways that have been found to be coordinately over-expressed in tumors leading to poor outcome. BUB1, CCNB1, MYBL2, PKMYT1, PRR11 and ORC6L are cell cycle-associated genes. DIAPH is a gene involved in actin cytoskeleton organization and biogenesis. DC13 is expected to be involved with the assembly of cytochrome oxidase.

Whereas previously reported studies were limited to the use of frozen tissues as the source of RNA and were profiled on microarrays, the invention described in this example demonstrates that real-time RT-PCR may be used for gene profiling in FFPE tumor samples. Thus, it provides for the use of archived breast cancer tissue sections from patients who have extended-outcomes data that predate the routine use of adjuvant therapy.

Distant metastasis-free survival is the prognostic endpoint for the study described in this example. A supervised principal components (SPC) method was used to build the 14-gene signature panel of the invention. The approach used in assembling the signature allowed the derivation of a metastasis score (MS) that can translate an individual's expression profile into a measure of risk of distant metastasis, for any given time period. The ability to quantify risk of metastasis for any timeframe provides highly flexible prognosis information for patients and clinicians in making treatment decisions, because the risk tolerance and time horizon varies among patients.

With the 14-gene molecular signature, high and low-risk groups had significant differences in distant metastasis-free and overall survival rates. This signature includes proliferation genes not routinely tested in breast cancer prognostics. The 14-gene signature has a ten gene overlap with the 50-gene signature described by H. Dai, L J van't Veer et al. (2005, in *Cancer Res* 15:4059-4066). In contrast, only six genes overlap with the 70-gene signature described by Dai, van't Veer et al. (2002, *Nature* 415:530-536). This may be explained by the fact that that study analyzed a more heterogeneous group of patients, which included both ER-positive and negative patients. The signature described herein had two proliferation gene overlaps with the 16-gene signature described by S P Paik, S. Shak et al., (2004, *N Engl J Med* 351:2817-2826).

The molecular signature described herein has independent prognostic value over traditional risk factors such as age, tumor size and grade, as indicated from multivariate analyses. This signature provides an even more compelling measure of prognosis when the tumor grade is low. As reported by Dai et al., a subset of this patient group with low grade tumors may be at even higher risk of metastasis than previously estimated. (Dai et al., 2005, *Cancer Res* 15:4059-4066). The signature described herein also extends the confidence in the prognostic genes initially reported by van't Veer et al. (2002, *Nature* 415:530-536) and Dai et al. (2005, *Cancer Res* 15:4059-4066), who primarily used samples from women less than 55 years of age, because this signature was validated on patients with a broad age distribution (median 64 years old), which is similar to the general range of breast cancer patients.

The use of FFPE tissues to sample even smaller amounts of sectioned tumor than microarray studies using frozen tissue, corroborated a subset of the genes on a different detection platform (quantitative PCR versus microarrays). This reiteration of results is consistent with the concept described by Bernards and Weinberg, that metastatic potential is an inherent characteristic of most of, rather than a small fraction of, the cells in a tumor. (R. Bernards and R A Weinberg, 2002, *Nature* 418:823).

The invention described herein also provides an objective estimate of prognosticator performance by using the pre-validation technique proposed by Tibshirani and Efron. (R. Tibshirani, B. Efron, 2002, *Statistical Applications in Genetics and Molecular Biology* 1:article 1). Several investigators have noted the importance of independent validation in increasingly large and characterized datasets. (R. Simon, *J Clin Oncol*, 2005, 23:7332-7341; D F Ransohoff, 2004, *Nat Rev Cancer* 4:309-14; D F Hayes, B. Trock et al., 1998, *Breast Cancer Res* 52: 305-319; D G Altman and P. Royston, 2000, *Stat Med* 19:453-73).

In the present invention, a unique 14-gene prognostic signature is described that provides distinct information to conventional markers and tools and is not confounded with systemic treatment. While the signature was developed using FFPE sections and RT-PCR for early stage, node-negative, ER-positive patients, it may be used in conjunction with any method known in the art to measure mRNA expression of the genes in the signature and mRNA obtained from any tumor tissue source, including but not limited to, FFPE sections, frozen tumor tissues and fresh tumor biopsies. Based on the mRNA expression levels of the 14-gene signature of the invention, a metastasis score can be calculated for quantifying distant metastasis risk for any individual breast cancer patient. Thus, the invention disclosed herein is amenable for use in routine clinical laboratory testing of ER-positive breast cancer patients for any timeframe.

Example Two

The 14-Gene Signature Predicts Distant Metastasis in Untreated Node-Negative, ER-Positive Breast Cancer Patients Using 280 FFPE Samples Efforts were undertaken to validate the 14-gene expression signature that can predict distant metastasis in node-negative (N−), estrogen receptor positive (ER+) breast cancer patients in an independent sample set who had not received systemic treatment. Reference is made to the experimental protocols and statistical analyses in Example 1, which were used to assay the effectiveness of the 14-gene signature.
Patients & Methods A retrospective search of the Breast Tissue and Data Bank at Guy's Hospital was made to identify a cohort of patients diagnosed with primary breast cancer and who had definitive local therapy (breast conservation therapy or mastectomy) but no additional adjuvant systemic treatment. The study group was restricted to women diagnosed between 1975 and 2001, with a clinical tumor size of 3 cm or less, pathologically uninvolved axillary lymph nodes, ER-positive tumor and with more than 5 years follow-up. A total of 412 patients were identified who also had sufficient formalin fixed, paraffin embedded (FFPE) tissues available for RNA extraction. The use of patient material and data for this study has been approved by Guy's Research Ethics Committee.

From this group there was sufficient quantity and quality of mRNA to profile tumors from 300 patients. Subsequently a further 20 cases were excluded from the study. Six patients had bilateral breast cancer prior to distant metastasis, 6 had a missing value in gene expression levels and 8 tumors proved to be ER negative upon re-assessment using current techniques. Thus, in total 280 patients were included in the analyses (validation set from Guy's Hospital in Table 1). To assess selection bias, the 280 patients who were analyzed were compared with the 412 patients who were identified to satisfy the inclusion criteria and had sufficient FFPE tissues for RNA extraction. No selection bias was detected as there were no significant differences in age, tumor size and histologic grade between the two sets.

ER status on this group of patients had been re-evaluated using contemporary IHC assay. Allred score 3 or more were considered receptor positive. Tumors were classified according to WHO guidelines (World Health Organization, Geneva, Switzerland. Histological typing of breast tumours. Tumori 1982; 68:181), and histological grade established using the modified Bloom and Richardson method (Elston C W & Ellis I O. Pathological prognostic factors in breast cancer. I. The value of histological grade in breast cancer: experience from a large study with long term follow-up. Histopathology 1991; 19:403-10).

Compared with the training set, the validation set was younger, with larger tumors and with a larger proportion of high grade tumors (Table 1). Tests for differences in those characteristics are highly significant ($p<0.001$).
Metastasis Score MS in Equation 1 derived in the training samples in Example 1 was applied to the untreated patients from Guy's Hospital. In example 1, RNA had been enriched, whereas in the case of untreated patients from Guy's Hospital, the RNA samples were not enriched.

To apply MS to the un-enriched samples, conversion factors between enriched and un-enriched samples were obtained from 93 training samples in Example 1 for each of the genes in the molecular signature.
Results
Distant Metastasis Free and Overall Survival Rates in Low-Risk and High-Risk Groups There were 4 (5.6%) distant metastases in the 71 MS low-risk and 62 (29.7%) distant metastases in the 209 MS high-risk patients, respectively. Kaplan Meier estimate (FIG. 3a) indicated significant differences in DMFS between the two groups with a log-rank p-value of 6.02e-5. The 5-year and 10-year DMFS rates (standard error) in the low-risk group were 0.99 (0.014) and 0.96 (0.025) respectively. For the high-risk group, the corresponding survival rates were 0.86 (0.025) and 0.76 (0.031) (Table 12).

For the Adjuvant! risk groups, Kaplan Meier curves of DMFS were shown in FIG. 3c. The 5-year and 10-year DMFS rates (standard error) were 0.96 (0.023) and 0.93 (0.03) for the low-risk group and 0.87 (0.03) and 0.77 (0.031) for the high-risk group, respectively. There were larger differences in survival rates between the high-risk and low-risk groups defined by MS than those defined by Adjuvant!.

For overall survival (OS), Kaplan Meier curves (FIG. 3b) indicated significant difference in OS rates between MS low-risk and high-risk groups (log-rank p-value=0.00028). The 5-year and 10-year OS rates were 0.97 (0.020) and 0.94 (0.028) for the low-risk group and 0.92 (0.019) and 0.71 (0.032) for the high-risk group, respectively. FIG. 3d showed the Kaplan Meier curves for Adjuvant! to predict 5-year and 10-year overall survival. MS and Adjuvant! provide similar prognostic information for overall survival.
Hazard Ratios from Univariate and Multivariate Cox Regression Models The unadjusted hazard ratio of the high-risk vs. low-risk groups by MS to predict time to distant metastases was 6.12 (95% CI=2.23 to 16.83) (Table 10). The unadjusted hazard ratio for MS risk groups is higher than those for groups defined by Adjuvant!, age, tumor size and histologic grade. Adjuvant! had the second highest hazard ratio of 2.63 (95% CI 1.30-5.32). Risk groups by histologic grade and tumor size were significant in predicting DMFS, but not the age group.

Age group is the most significant prognostic factor in predicting OS with an unadjusted hazard ratio of 2.9 (95% CI 2.03-4.18) (Table 10). Nevertheless, MS risk group can predict overall survival with HR of 2.49.

In the multivariate Cox regression (Table 11a) of time to distant metastases with the MS risk group and clinicopathological risk factors of age, tumor size and histological grade, the hazard ratio of the MS risk group, adjusted by age, tumor size and histologic grade, is 4.81 (1.71-13.53, p=0.003). MS risk group was the only significant risk factor in the multivariate analysis. Therefore, the gene signature has independent prognostic value for DMFS over the traditional clinicopathological risk factors and captures part of information within these factors.

In the multivariate Cox regression of time to distant metastases with the risk groups by the 14-gene signature and by Adjuvant! (Table 11b), the corresponding adjusted hazard ratios were 5.32 (1.92-14.73) and 2.06 (1.02-4.19). Both MS and Adjuvant! risk groups remained significant to predict DMFS. This indicates that MS and Adjuvant! carried largely independent and complementary prognostic information to each other.

Performance of the Molecular Signature in Different Clinical Subgroups

Table 13 shows that the gene signature predicts distant metastasis in young and old, pre-menopausal and post-menopausal women. While highly prognostic in patients with small size tumors (HR=14.16, p=0.009), it is not significant in patients with tumors larger than 2 cm. While hazard ratio in the low-grade subgroup (HR=7.6) is higher than that in the high-grade (HR=4.6), it only shows a trend to significance (p=0.06) in the low-grade subgroup because of small sample size (7 events in 60 samples).

Hazard ratios in various subgroups indicated that the gene signature is more prognostic in low grade, small size tumors, young and pre-menopausal patients in the validation sample set. Formal tests for interaction between the MS risk group and the clinical variables were not significant. However, the signature was also more prognostic in the low-grade tumors in the CPMC training set. Nevertheless, interaction analyses should be regarded as exploratory as multiple tests were performed.

Diagnostic Accuracy and Predictive Values

The diagnostic accuracy and predictive values of the risk groups by MS and Adjuvant! to predict distant metastases in 10 years were shown in Table 14. The MS risk group has higher sensitivity of 0.94 (0.84-0.98) than the Adjuvant! risk group's 0.90 (0.78-0.96) while the specificity is similar (0.3 (0.24-0.37) for MS vs. 0.31 (0.26-0.38) for Adjuvant!). Using 0.18 as the estimated prevalence of distant metastases in 10 years, PPV and NPV for MS risk group were 0.23 (0.21-0.25) and 0.97 (0.88-0.99) respectively. The corresponding values were 0.23 (0.20-0.25) and 0.93 (0.85-0.97) for the Adjuvant! risk group. Therefore, MS can slightly better predict those who would not have distant metastases within 10 years than Adjuvant! while the predictive values for those who would have distant metastases within 10 years were similar for the molecular and clinical prognosticators.

ROC curves (FIG. 4) of continuous MS to predict distant metastasis within 5 years and 10 years had AUC (95% CI) of 0.73 (0.65-0.81), 0.70 (0.63-0.78). A ROC curve to predict death in 10 years had an AUC of 0.68 (0.61-0.75). Hence, MS are predictive of both distant metastases and deaths.

In comparison, AUCs of ROC curves to predict distant metastases within 5 years, 10 years and death in 10 years by Adjuvant! were 0.63 (0.53-0.72), 0.65 (0.57-0.73) and 0.63 (0.56-0.71) and they were lower than the corresponding values by MS.

MS as a Continuous Predictor of Probability of Distant Metastasis

FIG. 5 shows the probabilities of distant metastasis at 5 and 10 years for an individual patient with a metastasis score, MS. Five-year and ten-year distant metastasis probabilities have median (min–max) of 8.2% (1.4%-31.2%) and 15.2% (2.7%-50.9%) respectively. At zero MS, the cut point to define the risk groups, the 5-year and 10-year distant metastasis probabilities were 5% and 10%, respectively.

The probability of distant metastasis in 10 years by MS was compared with the probability of relapse in 10 years by Adjuvant! (FIG. 6). The coefficient of determination ($R^2$) was 0.15 indicating that only a small portion of variability in probability of distant metastasis by MS can be explained by Adjuvant! The probability of distant metastasis by MS was lower than the relapse probability by Adjuvant! as all recurrence events were included in the Adjuvant! relapse probability while only distant metastases were counted as an event in the MS estimate of probability of distant metastasis.

Discussion

Initially a 14-gene prognostic signature was developed based upon mRNA expression from FFPE sections using quantitative RT-PCR for distant metastasis in a node-negative, ER-positive, early-stage, untreated breast cancer training set. The resulting signature was used to generate a metastasis score (MS) that quantifies risk for individuals at different timeframes and was used to dichotomize the sample set into high and low risk. Following initial internal validation of training set using a recent "pre-validation" statistical technique, the expression signature was validated using the precise dichotomized cutoff of the training set in a similar and independent validation cohort. Performance characteristics of the signature in training and validation sets were similar. Univariate and multivariate hazard ratios were 6.12 and 4.81 for the validation set and 4.23 and 3.26 in the training set to predict DMFS, respectively. In multivariate analysis, only the metastasis score remained significant with a trend to significance for only tumor size of the other clinicopathological factors. The 14-gene prognostic signature can also predict overall survival with univariate hazard ratios of 2.49 in the validation set. ROC curves of continuous MS to predict distant metastasis within 5 and 10 years and to predict death in 10 years had AUC of 0.73, 0.70 and 0.68, respectively. The signature provided more compelling prognosis when the tumor grade was low (hazard ratio were 7.58 in the low grade and 4.59 in the high grade tumors). Dai et al, for example, interpreted the change in prognostic power of the classifier as not being reflective of a continuum of patients but instead differential performance in discrete groups of patients. When compared to risk calculated from Adjuvant!, a web-based decision aid, there was only a modest correlation with MS. In multivariate Cox regression, MS and Adjuvant! risk groups both remain significant prognostic factors when they are adjusted for each other. There were larger differences in survival rates between the high-risk and low-risk groups defined by MS relative to Adjuvant!. MS can better predict those who would not have distant metastases within 10 years than Adjuvant!. These data demonstrate that the molecular signature provides independent information to the prognostic tools either routinely or more recently being adopted for predicting breast cancer distant metastasis.

Example Three

The 14-Gene Signature Predicts Distant Metastasis in Both Treated and Untreated Node-Negative and ER-Positive Breast Cancer Patients Using 96 FFPE Samples Efforts were undertaken to validate a 14-gene expression signature that can predict distant metastasis in node negative (N−), estrogen receptor positive (ER+) breast cancer patients in an independent sample set having both treated and untreated patients. Reference is made to the experimental protocols and statistical analyses in Example 1, which were used to assay and evaluate the effectiveness of the 14-gene signature.

Patients & Methods

A cohort of 96 N−, ER+ breast cancer patients, with a mean age of 56.7 years, was selected for the validation study (Table 15). The patients in the validation study were selected from University of Muenster. Of those, 15 were untreated, 54 were treated with Tamoxifen alone, 6 were treated with chemotherapy alone, and 2 were treated with both Tamoxifen and chemotherapy. Nineteen patients had unknown treatment status. The 14 genes in the signature were profiled in FFPE samples using quantitative RT-PCR. A previously derived metastasis score (MS) was calculated for the validation set from the gene expression levels. Patients were stratified into two groups using a pre-determined MS cut point, which was zero.

Validation of Metastasis Score

MS in Equation 1 that was derived with samples in Example 1 was applied to the patients from University of Muenster. In this example, RNA from the tumor tissues was also enriched but to a lesser extent than those in Example 1. To apply MS to this example, conversion factors between enriched and un-enriched samples were obtained from 93 samples from University of Muenster for each of the 14 genes in the signature. The conversion factors between enriched and unenriched samples were also obtained from 93 training samples from CPMC in Example 1. The conversion factors between the gene expression levels from CPMC and University of Muenster were then calculated using those two sets of conversion factors.

Results

Distant-Metastasis-Free Survival Rates

Using MS zero as cut point, patients were classified as high-risk and low-risk. Of all 96 patients, 48 patients were identified as high-risk with a 5-year DMF survival rate (standard error) of 0.61 (0.072) while 48 low-risk patients had a corresponding survival rate of 0.88 (0.052). Of the 62 treated patients, 32 high-risk and 30 low-risk patients had 5-yr DMF survival rates of 0.66 (0.084) and 0.89 (0.060), respectively. Of the 54 patients who received Tamoxifen treatment alone, 26 high-risk and 28 low-risk patients had 5-yr DMF survival rates of 0.65 (0.094) and 0.88 (0.065) respectively (Table 16).

Unadjusted Hazard Ratios

For the entire cohort, the MS correlated with distant metastasis-free (DMF) survival. Cox proportional hazard regression indicated 2.67 (1.28-5.57) times increased hazard per unit increase of MS (p=0.0087). Using zero as cut point, The hazard ratio of high-risk vs. low-risk patients in the entire cohort was 2.65 (1.16-6.06, p=0.021). For 61 treated patients, the hazard ratio was 3.08 (0.99-9.56, p=0.052). For the 54 patients who were treated with Tamoxifen only, the hazard ratio was 2.93 (0.92-9.35, p=0.07). Survival rates and hazard ratios for different groups of patients are summarized in Table 16 and FIG. 7, respectively.

An RT-PCR based 14-gene signature, originally derived from untreated patients, can predict distant metastasis in N−, ER+, Tamoxifen-treated patients in an independent sample set using FFPE tissues. There was a large differential DMFS rates between high and low risk Tamoxifen-treated alone patients (0.65 vs. 0.88) where two groups were defined by MS using zero as cut point. Differential risk between top and bottom quintiles of multi-modal MS were 3.99 and 3.75 fold for all and Tamoxifen-treated alone patients, respectively. The prognostic signature may provide baseline risk that is not confounded with systemic treatment. Moreover, it can predict metastatic risk for patients who receive treatment. Therefore, the gene signature would be applicable in identifying women with a poor clinical outcome to guide treatment decisions, independent of the subsequent therapies.

Example Four

The 14-Gene Signature Predicts Distant Metastasis in Tamoxifen-Treated Node-Negative and ER-Positive Breast Cancer Patients Using 205 FFPE Samples Patients A cohort of 205 women with N−, ER+ cancer who had surgery between 1975 and 2001 in Guy's Hospital was selected. The median follow-up was 9.3 years. Among them, there were 17 (8.9%) distant metastases, 44 deaths (21.5%) and 17 (8.9%) local and distant recurrences.

138 (67.3%) patients were at stage I while 67 (32.7%) were at stage II. All patients received adjuvant hormonal treatment but no chemotherapy. The cohort had a mean (SD) age of 59.3 (10.4) years. 64% were over the age of 55 years and 80.5% were post-menopausal. All tumors were ≤3 cm in diameter and the mean (SD) tumor diameter was 1.67 cm (1.0). 60 (29.3%), 98 (47.8%) and 47 (22.9%) patients had tumors of histological grade 1, 2 and 3, respectively. (Table 17)

Endpoints

Time from surgery to distant metastasis, also referred to as distant-metastasis-free survival (DMFS), was chosen as the primary endpoint. Events were distant metastases. Contralateral recurrences and deaths without recurrence were censoring events while local recurrences were not considered events or censoring events. The definition of DMFS endpoint, its events and censoring rules were aligned with those adopted by the National Surgical Adjuvant Breast and Bowel Project (NSABP) for the prognostic molecular marker studies (Paik et al 2004). The DMFS endpoint is most directly linked to cancer related death.

Gene Expression Signature and Metastasis Score (MS)

A 14-gene signature was previously developed using profiling study by RT-PCR with FFPE samples from California Pacific Medical Center (CPMC) as described in Example 1. Pathway analyses by the program Ingenuity revealed that the majority of the 14 genes in the signature are involved with cell proliferation. Ten of 14 genes are associated with TP53 signaling pathways that have been found to be coordinately over-expressed in tumors of poor-outcome.

A Metastasis Score (MS) was calculated for each individual. MS in this example was based upon the gene expression of the 14 genes in the signature as previously described. However, the algorithm for calculating MS in this example was different from the algorithm described for the previous examples. Nevertheless, MS derived with the new algorithm was highly correlated with MS derived with the previous method with Pearson correlation coefficient>0.99. Moreover, in this example, two cut points were employed to group patients into high, intermediate and low MS groups as opposed to using only one cut point to categorize patients into low and high risk groups in the previous three examples.

While the 14 genes in the signature were chosen in the study as described in Example 1, the new MS and cut points were determined based upon the study using untreated samples from Guy's Hospital as described in Example 2. The new MS algorithm was applied and validated in Examples 4 and 5. The new Metastasis Score (MS(new)) is now calculated as the negative of the mean of the gene expression level of 14 genes. With this new score, the 14 genes were given equal weighting. The −1 multiplier was used so that higher MS corresponds to higher risk of distant metastasis. The new MS can be expressed in the following formula:

$$MS(\text{new}) = -(1/14) * \left[\sum_{i=1}^{14} Gi\right] \quad \text{Equation 3}$$

where Gi are the centered expression levels of the 14 genes in the signature.

Two cut points of MS(new) were chosen to categorize patients into high, intermediate and low MS groups. The lower cut point was −1.47 while the upper cut point was −0.843. Individuals with MS smaller than −1.47 were in the low MS group. Individuals with MS between −1.47 and −0.843 were in the intermediate MS group while those with MS greater than −0.843 were in the high MS group. If those with low MS were considered low-risk while those in intermediate MS and high MS groups were considered as high risk in Guy's untreated samples (in other word those with MS above −1.47 were considered high risk), then sensitivity of the MS risk groups would be above 90%. On the other hand, if those with low MS and intermediate MS were considered low-risk while those with high MS were considered high-risk (in other words, those with MS lower than −0.843 were considered low-risk while those with MS higher than −0.843 were considered high-risk), then the sensitivity and specificity of the MS risk groups in Guy's untreated samples would be the same at 70%.

For the untreated samples, the intermediate MS group has risk similar to that of high MS group and the high and intermediate MS groups had higher risk than those with low MS. However, for patients treated with hormonal treatment, the intermediate MS group has risk similar to that of the low MS group. The risk of high MS group is higher than the risk of intermediate MS and low MS groups.

Another method of applying the 14 gene signature is by using Equation 2, as follows. A 14-gene signature was previously developed using profiling study by RT-PCR with FFPE samples from California Pacific Medical Center (CPMC) as described in Example 1. Pathway analyses by the program Ingenuity revealed that the majority of the 14 genes in the signature are involved with cell proliferation. Ten of 14 genes are associated with TP53 signaling pathways that have been found to be coordinately over-expressed in tumors of poor-outcome.

A Metastasis Score (MS) was calculated for each individual. MS in this example was based upon the gene expression of the 14 genes in the signature as previously described. However, the algorithm for calculating MS in this example was based upon Equation 2 in which the 14 genes were weighted equally. Moreover, in this example, two cut points were employed to group patients into high, intermediate and low MS groups as opposed to using only one cut point to categorize patients into low and high risk groups in the previous three examples. While the 14 genes in the signature were chosen in the study as described in Example 1, the new MS and cut points were determined based upon the study using untreated samples from Guy's Hospital as described in Example 2. The new MS algorithm was applied and validated in Examples 4 and 5.

Two cut points of MS(new) were chosen to categorize patients into high, intermediate and low MS groups. Cut points were determined such that when individuals with MS above the first cut point of −0.119 were classified as high-risk individuals to have distant metastasis in 5 years, the sensitivity of the MS risk groups would be above 90%. The second cut point of MS=0.302 was chosen such that sensitivity and specificity would be the same at 0.7.

It should be noted that the MS determined in Equation 2 and MS as the negative of the mean of gene expression of all 14 genes are simply linear transformation of each other. As such they have perfect correlation (Pearson correlation coefficient=1) and the classification of patients into high, intermediate, and low MS are the same using the corresponding cut points as described.

Statistical Analyses

Kaplan-Meier (KM) curves for distant metastasis free survival were generated for the high, intermediate and low MS groups. Upon examining the DMFS rates of the three groups, intermediate and low MS groups were combined as a low-risk group which was compared with the high risk group with high MS. Log rank tests were performed.

Univariate and multivariate Cox proportional hazard regression analyses of MS groups for DMFS endpoint were performed. Hazard ratio of high-risk (high MS) vs. low-risk (intermediate and low MS groups combined) group was adjusted for age (in years), tumor size (in cm) and histological grade in multivariate analysis.

Association of MS groups with age, tumor size was investigated using ANOVA tests while association of MS groups with histological grade was evaluated by Crammer's V for strength of association and by chi-sq tests for statistical significance.

Hazard ratios of the MS risk groups were also calculated for different clinical subgroups. Those groups include pre-menopausal vs. post-menopausal, age≤55 years vs.>55 years, tumor size>2 cm vs.≤2 cm, and histological grade 1 & 2 vs. grade 3.

To assess diagnostic accuracy, Receiver Operator Characteristic (ROC) curve of MS to predict distant metastases within 5 years was plotted. Area under the ROC curves (AUC) was calculated. Sensitivity, specificity, positive predictive value (PPV) and negative predictive value (NPV) were calculated with 95% confidence interval (95% CI) for high vs. low-risk groups by MS.

The time-dependence of hazard ratio of MS groups was investigated by estimating the annualized hazards using a spline-curve fitting technique that can handle censored data. The HEFT procedure in R2.4.1 was employed. Annualized hazards were estimated for both MS high and low-risk groups and from which, the hazard ratios at different time were calculated.

Kaplan Meier estimates and Cox proportional hazard regression were performed using R2.41.1 and SAS 9.1. ROC curves and AUC were estimated using the Mayo Clinic's ROC program. The Delong method of estimating confidence interval of AUC was employed.

Results
Distant-Metastasis-Free Survival Rates in MS Low-Risk and High-Risk Groups There were 8 distant metastases in the low MS group of 136 individuals, 2 distant metastases in the intermediate MS group of 29 individuals and 7 distant metastases in the high MS group of 40 individuals. The 10-year DMFS rates (SE) were 0.921 (0.028), 0.966 (0.034) and 0.804 (0.068) for low, intermediate, and high MS groups, respectively. There were significant differences in DMFS rates with a log-rank p-value of 0.04. As DMFS rates were similar in low and intermediate MS groups, they were combined to form the low-risk group. The low-risk group had a 10-year DMFS rate of 0.928 (0.025) and was significantly different from the corresponding rate of 0.804 (0.068) for the high-risk group (Table 18). The log-rank p-value was 0.011. Kaplan-Meier plots of distant-metastasis-free survival for the three MS groups and the two MS risk groups were in FIG. 8 and FIG. 9, respectively.

Hazard Ratios from Univariate and Multivariate Cox Regression Models

The unadjusted hazard ratio of the MS high-risk vs. low-risk groups to predict time to distant metastases was 3.25 (95% CI=1.24 to 8.54, p-value=0.017). When adjusted by age, tumor size and histological grade, the hazard ratio was 5.82 (1.71-19.75, p=0.0047) in Table 19. MS risk group was the only risk factor that was significant in the multivariate analyses. Therefore, the gene signature has independent prognostic value for DMFS over the traditional clinicopathological risk factors and captures part of the information of these factors.

Association of MS Risk Groups with Other Clinical and Pathological Characteristics MS risk group had very significant association with histological grade (Crammer's V=0.65, p<0.0001 for chi-sq test for association). For 60 grade 1 tumors, none (0%) was MS high-risk. In contrary, 9 (9.2%) of 98 grade 2 and 31 (66%) of 47 grade 3 tumors were MS high-risk.

While tumor size was larger in the MS high-risk group, the difference was not statistically different (1.87 cm and 1.61 cm in MS high and low-risk groups respectively, ANOVA p-value=0.14). There was no significant association of MS risk groups with age (Mean age is 59.3 in both high and low-risk groups, ANOVA p=0.34). Results were summarized in Table 20.

Performance of the Molecular Signature in Different Clinical Subgroups

Hazard ratio of MS risk groups was 3.7 (1.1-12.6) in tumors≤2 cm and 3.0 (0.6-14.8) in tumors>2 cm. In women younger than 55 years, HR was 7.4 (1.0-54.7) while it was 2.8 (0.88-8.8) in women older than 55 years. For tumors of histological grade 1 and 2, HR was 12.8 (3.8-43.1) while HR was 1.53 (0.16-14.7) in grade 3 tumors (Table 21).

Diagnostic Accuracy and Predictive Values

Sensitivity, specificity, PPV and NPV of MS risk groups to predict distant metastasis in 5 years were shown in Table 22. Sensitivity of MS risk group was 0.50 (0.50-0.76) while specificity was 0.82 (0.76-0.87). Using the estimated 5-year distant metastasis rate of 0.05, PPV and NPV were estimated to be 0.13 (0.068-0.23) and 0.97 (0.94-0.98) respectively (Table 22). High NPV of the MS risk group was important for it to be used for ruling out more aggressive treatment such as chemotherapy for patients with low-risk.

ROC curve of continuous MS to predict distant metastasis within 5 years was shown in FIG. 10 and AUC was estimated to b 0.72 (0.57-0.87).

Time Dependence of the Prognostic Signature

Annualized hazard rates for MS high and low-risk groups were shown in FIG. 11a while the time-dependence of the hazard ratio between two groups was shown in FIG. 11b. For the high-risk group, annual hazard rate peaked at 2.5% around year 3 from surgery and then slowly decreased over the next few years. However, the annualized hazard rate in the low-risk group showed slight but steady increase in the 10-year period that had follow-up. Subsequently, hazard ratio of MS risk groups was time dependent. It was 4.6, 3.6 and 2.1 at year 2, 5 and 10, respectively.

Example Five

The 14-Gene Signature Predicts Distant Metastasis in Adjuvant Hormonally-Treated Node-Negative and ER-Positive Breast Cancer Patients Using 234 FFPE Samples Patients A cohort of 234 Japanese women with N−, ER+ breast cancer who had surgery between 1995 and 2003 in Aichi Cancer Center was selected. The median follow-up was 8.7 years. Among them, there were 31 (13%) distant metastases, 19 deaths (8.1%) and 46 (19.7%) local and distant recurrences.

146 (62%) patients were at stage I while 88 (38%) were at stage II. All patients received adjuvant hormonal treatment but no chemotherapy. 112 post-menopausal women were treated with Tamoxifen. Of 122 pre-menopausal women, 102 received Tamoxifen while 20 received Zoladex treatment. The cohort had a mean (SD) age of 53 (11) years and mean (SD) tumor diameter of 2.05 cm (1.1). 74 (32%), 113 (48%) and 47 (20%) patients had tumors of histological grade 1, 2 and 3, respectively. (Table 23)

Gene Expression Signature and Metastasis Score (MS)

A 14-gene expression signature was previously developed and validated in profiling studies in US and Europe using RT-PCR with FFE samples. Pathway analyses by the program Ingenuity revealed that the majority of the 14 genes in the signature are involved with cell proliferation. Ten of 14 genes are associated with TP53 signaling pathways that have been found to be coordinately over-expressed in tumors of poor-outcome.

A Metastasis Score (MS) was calculated for each individual. MS was based upon the negative of the mean of the gene expression levels (in ΔΔCt) of the 14 genes in the signature. Moreover, two cut points had previously been determined from a study with tumor samples from untreated patients from Guy's Hospital (Example 2) to group patients into high, intermediate and low MS groups.

Statistical Analyses

Kaplan-Meier (KM) curves for distant metastasis free and overall survival were generated for the high, intermediate and low MS groups. Upon examining the DMFS rates of the three groups, intermediate and low MS groups were combined as a low-risk group which was compared with the high risk group with high MS. Log rank tests were performed.

Univariate and multivariate Cox proportional hazard regression analyses of MS groups for DMFS and OS endpoints were performed. Hazard ratio of high-risk (high MS) vs. low-risk (intermediate and low MS groups combined) group was adjusted for age (in years), tumor size (in cm) and histological grade in one multivariate analysis. In another multivariate analysis, it was adjusted for menopausal status, treatment, tumor size, histological grade and PgR status.

Association of MS groups with age, tumor size was investigated using ANOVA tests while association of MS groups with histological grade and tumor subtypes was evaluated by Crammer's V for strength of associated and by chi-sq tests for statistical significant.

Hazard ratios of the MS risk groups were also calculated for different clinical subgroups. Those groups include pre-menopausal vs. post-menopausal, age≤55 years vs.>55 years, tumor size>2 cm vs.≤2 cm, and histological grade 1 & 2 vs. grade 3, PgR +ve vs. −ve.

To assess diagnostic accuracy, Receiver Operator Characteristic (ROC) curve of MS to predict distant metastases within 5 years was plotted. Area under the ROC curves (AUC) was calculated. Sensitivity, specificity, positive predictive value (PPV) and negative predictive value (NPV) were calculated with 95% confidence interval (95% CI) for high vs. low-risk groups by MS.

The time-dependence of hazard ratio of MS groups was investigated by estimating the annualized hazards using a spline-curve fitting technique that can handle censored data. The HEFT procedure in R2.4.1 was employed. Annualized hazards were estimated for both MS high and low-risk groups and from which, the hazard ratios at different time were calculated.

Kaplan Meier estimates and Cox proportional hazard regression were performed using R2.41.1 and SAS 9.1. ROC curves and AUC were estimated using the Mayo Clinic's ROC program. The Delong method of estimating confidence interval of AUC was employed.

Results

Distant-Metastasis-Free Survival Rates in MS Low-Risk and High-Risk Groups

There were 6 distant metastases in the low MS group of 77 individuals, and 4 distant metastases in the intermediate MS group of 66 individuals and 21 distant metastases in the high MS group of 95 individuals. The 10-year DMFS rates (SE) were 0.89 (0.05), 0.91 (0.04) and 0.75 (0.05) for low, intermediate, and high MS groups, respectively. There was significant difference in DMFS rates with a log-rank p-value of 0.004. As DMFS rates were similar in low and intermediate MS groups, they were combined to form the low-risk group. The low-risk group had a 10-year DMFS rate of 0.895 (0.034) and is significantly different from the corresponding rate of 0.75 (0.05) for the high-risk group (Table 24). The log-rank p-value is 0.00092. Kaplan-Meier plots of distant-metastasis-free survival for three MS groups were in FIG. 12 while Kaplan-Meier plots for the two risk groups (high MS and a combination of intermediate and low MS) were in FIG. 13.

Hazard Ratios from Univariate and Multivariate Cox Regression Models

The unadjusted hazard ratio of the MS high-risk vs. low-risk groups to predict time to distant metastases was 3.32 (95% CI=1.56 to 7.06, p-value=0.0018). When adjusted by age, tumor size and histological grade, the hazard ratio was 3.79 (1.42-10.1, p=0.0078). Beside MS, tumor size is the only other significant factor in the multivariate analyses with HR of 1.4 per cm increase (p=0.007) (Table 25). In another multivariate analysis, MS risk groups were adjusted by menopausal status, treatment, tumor size, histological grade and PgR status. The adjusted hazard ratio of MS risk group was 3.44 (1.27-9.34) (Table 27). Again, tumor size was the only other significant factor in this multivariate analysis (HR=1.45 per cm increase, p=0.0049). Therefore, the gene signature has independent prognostic value for DMFS over the traditional clinicopathological risk factors and captures part of the information of these factors.

Association Of MS Risk Groups with Other Clinical and Pathological Factors

MS risk group had very significant association with histological grade (Crammer's V=0.54, p<0.0001 for chi-sq test for association). For 74 grade 1 tumors, only 4 (5.4%) were MS high-risk. In contrary, 54 (47.8%) of 113 grade 2 and 37 (78.7%) of 47 grade 3 tumors were MS high-risk.

MS risk groups were also associated with tumor subtypes (Cramer's V=0.25, p=0.02). While 23 (29.8%) of 77 Scirrhous tumors were MS high-risk, 45 (41.7%) of 108 Papillo-tubular tumors and 24 (63.2%) of 38 solid-tubular were MS high-risk.

While tumor size is larger in the MS high-risk group (2.23 cm and 1.93 in MS high and low-risk groups respectively, ANOVA p-value=0.037), there was no significant association of MS with age (p=0.29). Results were summarized in Table 26.

Performance of the Molecular Signature in Different Clinical Subgroups

MS risk group can best predict distant metastases in young (age≤55 years), pre-menopausal women with tumors that were ≤2 cm, low grade (grade 1 and 2) and PgR +ve. Hazard ratio of MS risk groups was 4.5 (1.2-17.3) in tumors≤2 cm and 2.3 (0.92-5.6) in tumors>2 cm. In pre-menopausal women, HR was 6.0 (1.6-23.3) while it was 2.1 (0.83-5.1) in post-menopausal women. For those with tumors of histological grade 1 and 2, HR was 3.6 (1.5-8.4) while HR was 2.4 (0.29-18.8) in grade 3 tumors. HR of MS risk group was 3.5 (1.4-9.0) in PgR +ve tumors while it was 2.1 (0.57-7.49) in PgR −ve tumors (Table 28).

Diagnostic Accuracy and Predictive Values

Sensitivity, specificity, PPV and NPV of MS risk groups to predict distant metastasis in 5 years were shown in Table 29. Sensitivity of MS risk group was 0.81 (0.60-0.92) while the specificity was 0.65 (0.58-0.71). Using the estimated 5-year distant metastasis rate of 0.095, PPV and NPV were estimated to be 0.19 (0.15-0.24) and 0.97 (0.93-0.99) respectively (Table 29). High NPV of the MS risk group was important for it to be used for ruling out more aggressive treatment such as chemotherapy for patients with low-risk. ROC curve of continuous MS to predict distant metastasis within 5 years was shown in FIG. 14 and AUC was estimated to b 0.73 (0.63-0.84).

Time Dependence of the Prognostic Signature

Annualized hazard rates for MS high and low-risk groups were shown in FIG. 15a while the time-dependence of the hazard ratio between two groups was shown in FIG. 15b. For the high-risk group, annual hazard rate peaked at 3.5% around year 3 from surgery and then slowly decreased over the next few years. However, the annualized hazard rate in the low-risk group showed slight but steady increase in the 10-year period that had follow-up. Subsequently, hazard ratio of MS risk groups was time dependent. It was 4.8, 3.4 and 1.8 at year 2, 5 and 10, respectively.

As seen from this example and the previous examples, the 14 gene signature is shown to be an effective risk predictor in breast cancer patients of both Caucasian and Asian ethnic background, indicating the robustness of the 14 gene prognostic signature.

Example Six

The 14-Gene Prognosis Signature ("Metastasis Score" ("MS")) Predicts Metastasis Risk in Tamoxifen-Treated Breast Cancer in Different Ethnogeographic Populations, and in Combination with Progesterone Receptor (PR) as a "Composite Metastasis Score" ("cMS")

Overview

A 14-gene expression signature (which may be referred to herein as a "metastasis score" ("MS")) that is prognostic of metastasis for untreated node-negative (N−), estrogen receptor-positive (ER+) breast cancer patients is described above in Examples One through Five. Herein in Example Six, it was determined whether the signature (1) was prognostic in tamoxifen-treated patients, (2) was comparably prognostic in a different ethnogeographic population, and (3) can improve outcome prediction when evaluated with progesterone receptor (PR) expression. The MS in combination with PR may be referred to herein as a "composite metastasis score" ("cMS").

Two N−, ER+, Tamoxifen-treated breast cancer cohorts at the Aichi Cancer Center ("ACC", n=205) in Japan and Guy's Hospital ("GH", n=203) in United Kingdom were selected. Gene expression levels for PR and individual genes of the 14-gene metastasis score were determined by RT-PCR. Estimates of hazard ratios (HR) for risk of distant metastasis were calculated by Cox proportional hazard models and the Kaplan-Meier method was used to estimate 10-year distant-metastasis-free survival (DMFS).

Multivariate models fit with a continuous risk score suggested an increase of 1.52 fold (p=0.05), 1.85 fold (p=0.03), and 1.55 fold (p=0.009) in metastasis risk per 10-unit increase in MS for the ACC, GH, and combined cohorts, respectively. With univariate analysis, the high MS (HR=2.61, p=0.008) and PR− (HR=3.64; p=0.0001) were associated with increased risk of distant metastasis and were independently associated after mutual adjustment (high MS HR=2.25, p=0.027 and PR−HR=3.15, p=0.0005). Stratification of the PR+ subgroup of the combined set resulted in DMFS at 10 years of 87.7% (82.2 to 93.2) and 92.9% (87.8 to 97.9) for MS high and low patients, respectively.

The 14-gene metastasis score is prognostic of metastasis risk in tamoxifen-treated breast cancer patients in variant ethnogeographic regions and can refine risk estimates of distant metastasis in PR+ tamoxifen-treated patients.

Introduction

A 14-gene expression signature (which may be referred to herein as a "metastasis score" ("MS")) that is prognostic of metastasis was developed from non-systemically N−, ER+ breast cancer patients and is described above in Examples One through Five. The equally-weighted 14-gene metastasis score was not confounded with the presence of treatment response-related genes and is independent of routinely used clinical information. Herein in Example Six, performance of the metastatic potential of breast tumors as determined by this metastasis score was assessed in tamoxifen-treated patients. Additionally, to ensure broad applicability of the metastasis score, samples from two different ethnogeographic regions were evaluated. Furthermore, the metastasis score was validated on samples from a population-based cohort that is representative of a typical community in which the assay could be used. Thus, herein in Example Six, it was determined whether the metastasis score successfully classifies outcomes in women receiving adjuvant hormonal therapy, is comparably prognostic in different ethnogeographic populations, and performs successfully in a community setting. The study was conducted on women who were diagnosed with ER+, N−breast cancer and treated with tamoxifen at the Aichi Cancer Center in Japan and Guy's Hospital in the United Kingdom.

Methods

Patients

Aichi Cancer Center Sample Set

A cohort of 215 Japanese women with N−, T1/T2, ER+ breast cancer who had received Tamoxifen therapy and underwent surgery between 1995 and 2003 at Aichi Cancer Center was selected. Tumors were classified according to WHO guidelines and histological grade established using the modified Bloom and Richardson method. The ER and PR status of patient samples were determined by standard IHC assay but the ER and PR results were reanalyzed and standardized using mRNA measurements to be consistent with previous studies.

209 patients were profiled from whom sufficient amounts of mRNA were extracted from formalin-fixed, paraffin-embedded tissues. Of the 209 patients, four subjects were further excluded from the study (the tumor in one patient had an unknown recurrence site; the tumor in one patient was DCIS; and the tumors in two patients proved to be ER-negative (ER−) upon re-assessment using the mRNA expression assay), leaving 205 patients for analysis. The median follow-up time of the 205 patients was nine years. The use of patient material and data for this study was approved by the institutional medical ethics committee.

Guy's Hospital Sample Set

A retrospective search of the Breast Tissue and Data Bank at Guy's Hospital was made to identify an analogous cohort of patients diagnosed with primary breast cancer and with Tamoxifen treatment. The study group was restricted to women diagnosed between 1989 and 2001, with a clinical tumor size of 3 cm or less, pathologically uninvolved auxiliary lymph nodes, ER+tumor, and with more than five years follow-up or recurrence, or death prior to five years. Tumors were classified according to WHO guidelines and histological grade established using the modified Bloom and Richardson method. ER and PR status on this group of patients had been determined using the standard IHC assay but the ER and PR results were reanalyzed and standardized using mRNA measurements to be consistent with previous studies.

A total of 234 patients were identified who also had sufficient FFPE tissue available for RNA extraction. From this group there was sufficient quantity and quality of mRNA to profile tumors from 218 patients. A further 15 cases were excluded from the study (five patients had bilateral breast cancer prior to distant metastasis, four patients had tumors that proved to be ER− upon re-assessment using the mRNA expression assay, three patients were treated with tamoxifen for a contralateral tumor rather than the first diagnosed tumor, one patient was treated with adjuvant CMF and tamoxifen, one patient had unknown nodal status, and one patient was a male patient). Thus, a total of 203 patients were included in the analyses. The median follow-up time of these 203 patients was 9.3 years. The use of patient material and data for this study was approved by Guy's Research Ethics Committee.

RNA Extraction & Gene Expression Profiling

Total RNA is extracted from the FFPE tissue sections using a modified commercially available isolation kit (Zymo Research, Orange, Calif.). A single-step RT-PCR with SYBR® Green was used to quantify the mRNA levels of the 14-gene metastasis score and 3 housekeeping (HSK) genes as well as ER and PR. The assays were performed on the Prism 7900 Real-Time PCR system.

Statistical Analyses

Differences between the patient characteristics of the two cohorts were determined by the Wilcoxon rank sum test for continuous variables and Fisher's exact test for categorical variables. Cox proportional hazards models (Cox, 1972) were used to estimate risk (hazard) ratios and their 95% confidence intervals. Wald tests of the coefficients from these models were performed to generate p-values for the explanatory variables. The metastasis score (MS) was fit both as a continuous variable as well as a dichotomous variable stratified by a previously established MS value of −23.5 (low risk≤−23.5<high risk). Other covariates included in the multivariable Cox models included age at surgery (years), tumor size (cm), and histologic grade of tumor (1, 2, 3). Multivariate Cox models that were fit on the combined ACC and Guy's cohorts included an additional indicator covariate for the Guy's cohort. Estimates of distant-metastasis-free survival (DMFS) and overall survival (OS) for the high and low MS groups were calculated by the method of Kaplan and Meier. The 95% confidence intervals for point estimates of survival were calculated using Greenwood's estimate of variance and the percentage points of a standard normal distribution (intervals that eclipsed 0 or unity were truncated at 0.0 or 1.0, respectively). The probabilities of distant metastasis at 5 and 9 years, for given metastasis scores, were calculated from survivor functions as estimated by Cox models including the continuous MS as the explanatory variable. Statistical analyses were performed with SAS software version 9.1 and R software version 2.7.2.

Formulation of the Composite Metastasis Score ("cMS")

The ACC and Guys combined ER+, tamoxifen-treated dataset (n=408) was split randomly into a training dataset (n=208) and a validation dataset (n=200). A Cox proportional hazard regression model for the distant metastasis endpoint was fit with the MS and PR $-\Delta\Delta Ct$ values from the training dataset. The parameter estimates from this model were used as weights to generate the composite metastasis score. Individual composite metastasis scores were calculated for the validation data set as the sum of the weighted MS and PR $-\Delta\Delta Ct$ values.

$$cmS_u = \beta_{MS}*MS + \beta_{PR}*PR$$

where $\beta_{MS}=0.0338$ $\beta_{PR}=-0.22026$
($cMS_u$ indicates an un-scaled cMS)

Since the actual range of the cMS values in the training dataset ranged from −3.28 to 0.66, for a total range of 3.94, the cMS was then rescaled to a 0-40 scale by shifting the scores by 3.28 and multiplying by 10, as follows:

$$cMS = (cMS_u + 3.28)*10$$

where
cMS=0 if $cMS_u$<0
cMS=40 if $cMS_u$>40

The rescaled cMS values were fit in a Cox proportional hazard model for the distant metastasis endpoint. Results of univariate and multivariate Cox proportional analyses of distant-metastasis-free survival (DMFS) using continuous cMS for the validation dataset is provided in Table 31. In univariate analysis, the hazard ratio (HR) per 10 unit increase was 2.77 (95% CI: 1.69-4.53, p<0.0001) for DMFS. After adjustment for age, tumor size, and tumor grade in Cox multivariate analysis, the HR per 10 unit increase was 3.18 (95% CI: 1.67-6.06, p=0.0005).

FIG. 16 provides Kaplan-Meier estimates of DMFS of the validation set by cMS. The Kaplan-Meier 9-year DMFS estimates were 78.9% for the high risk group and 95.2% for the low risk group.

Table 32 provides Kaplan-Meier estimates of DMFS using the cMS in the ACC and Guy's validation dataset for the high-risk group (cMS cutpoint at 1.738=high-risk group). For example, as shown in Table 32, the 9-year survival estimate for the high-risk group is 0.8192 (95% CI=0.7353-0.9031).

Table 33 provides Kaplan-Meier estimates of DMFS using the cMS in the ACC and Guy's validation dataset for the low-risk group (cMS cutpoint at 1.738=low-risk group). For example, as shown in Table 33, the 9-year survival estimate for the low-risk group is 0.9785 (95% CI=0.9487-1.0000).

Table 34 provides a Cox PH estimate of DMFS using the cMS in the ACC and Guy's validation dataset with a cMS cutpoint at 1.738.

In the examples shown in Tables 32-34, the cMS cutpoint at 1.738 would be equal to a cutpoint at 17.38 using a cMS rescaled to a 0-40 scale as described above.

Results

Patient Characteristics

No significant differences were found between the ACC and Guy's patients in regard to tumor diameter (median=1.8 cm and 2.0 cm, respectively; p=0.12), tumor grade (grade 1=34.2% and 29.6%, grade 2=46.8% and 48.3%, grade 3=19.0% and 22.2%; p=0.56), tumor stage (stage I=64.4% and 68.0%, stage II=35.6% and 32.0%; p=0.46), and distant metastasis (percent recurrence=12.7% and 7.9%; p=0.14). There were differences found between the two cohorts in regard to age and overall death. The ACC patients tended to be younger than the Guy's patients (median=52 and 59, ACC and Guy's respectively; p<0.0001) and exhibited a lower death rate than the Guy's patients (percent death=8.3% and 21.2%; p=0.0002).

Distribution of the Metastasis Score

The MS distributions for the ACC, Guy's (treated and untreated) and CPMC (untreated) cohorts were determined. The ACC cohort had a median MS of −14.5 with a range of −48.2 to 10.9. The Guy's treated and untreated samples had median MS of −24.7 (−50.3 to 8.7) and −17.3 (−57.1 to 15.1), respectively. The previously reported CPMC median MS was −23.5 (−72.8 to 16.8) and was used to stratify the ACC and Guy's subjects into high and low risk groups in subsequent analyses.

Association of the MS with DMFS in the ACC Cohort

A Cox proportional hazard model for DMFS fit with the MS indicated a 1.43 fold increase (95% CI 1.02 to 2.0; p=0.04) in metastasis risk per 10-unit increase in MS. When adjusted for the traditional risk factors of age, tumor size, and tumor grade, the increased risk was 1.52 fold (1.00 to 2.30; p=0.05). Similarly, the univariate hazard ratio for DMFS in a Cox model fit with a dichotomous MS variable stratified by the CPMC MS median of −23.5 (low risk≤−23.5<high risk) was 2.80 (0.84 to 9.33; p=0.09). The hazard ratio was 2.98 (0.82 to 10.77; p=0.10) after adjustment for the above risk factors.

Association of the MS with DMFS in the Guy's Cohort

In the Guy's treated data set, a 1.49 fold increase (1.01 to 2.21; p=0.04) in metastasis risk was observed per 10-unit increase in MS. This risk increased to 1.85 fold (1.05 to 3.25; p=0.03) after adjustment.

The Guy's treated univariate hazard ratio for DMFS in a Cox model fit with the dichotomous MS risk variable was 2.00 (0.75 to 5.38; p=0.17). After adjustment for the above risk factors, the hazard ratio remained at 2.00 (0.65 to 6.13; p=0.23).

The performance of the MS with DMFS in the Guy's untreated patients was previously determined. Herein in Example Six, the probability of distant metastasis for tamoxifen-treated vs. untreated patients was determined. The 9-year Cox model estimates of the probabilities of developing distant metastasis as a function of the continuous MS alone was determined. As the metastasis score increases, the difference between the probabilities of distant metastasis at 9-years for untreated versus tamoxifen-treated patients also increases.

Association of the MS with DMFS in the Combined ACC and Guy's Cohorts

Similar analyses were performed on the combined ACC and Guy's data sets. The increased risk per 10-unit increase in MS for the combined data was 1.51 fold (1.19 to 1.92;

p=0.0007). When adjusted for age, tumor size, tumor grade and cohort, the increased risk was 1.55 fold (1.11 to 2.15; p=0.009).

The univariate hazard ratio for DMFS in the combined data set using the dichotomous MS variable was 2.61 (1.28 to 5.32; p=0.008). After adjustment, the hazard ratio was 2.15 (0.96 to 4.82; p=0.06).

Kaplan-Meier Analyses of MS Stratified DMSF and OS Risks

In addition to Cox proportional hazard modeling, Kaplan-Meier analyses were performed for DMFS and OS where the subjects were stratified by the MS risk cut-point described above. Separation of the high and low risk strata occurred prior to 5 years for both the individual and combined cohorts when evaluated for DMFS. For the OS endpoint, the ACC strata separated prior to 5 years, but for the Guy's and combined cohorts no separation of strata was evident. Hazard ratios and p-values from the Cox models fit with the stratified MS were determined. The 5-year DMFS of the low-risk group were 96.0% (95% CI: 90.6-100%), 97.5% (95% CI: 94.7-100%), and 97.1% (95% CI: 94.5-99.6%) for ACC, Guy's, and combined cohorts, respectively, as compared to rates of 89.6% (95% CI: 84.7-94.6%), 92.6% (95% CI: 86.8-98.3%), and 90.7% (95% CI: 86.9-94.5%) for the high-risk group in the ACC, Guy's, and combined cohorts, respectively.

The proportion of subjects who experienced a distant metastasis event by 9 years follow-up for the treated, untreated, and combined treated cohorts was determined. K-M estimates and 95% CIs were determined for the risk-stratified subjects along with the marginal distributions of all subjects not stratified by MS risk. Among the patients classified as low-risk, the percentage of patients who would have distant metastasis at 9 years remain similar in the untreated and Tamoxifen-treated cohorts. However, in the high-risk group, the percentage of patients with distant metastasis is decreased after treatment with Tamoxifen.

Effect of Integrating PR Status with MS on Prognostic Value

With univariate analysis, the high MS (HR=2.61, 95% CI 1.28 to 5.32; p=0.008) and PR-negative status (HR=3.64; 95% CI 1.91 to 6.90; p=0.0001) were associated with increased risk of distant metastasis in the treated cohort and were independently associated after mutual adjustment (high MS HR=2.25, 95% CI 1.09 to 4.62, p=0.027 and PR-negative status HR=3.15, 95% CI 1.64 to 6.06, p=0.0005). DMFS at 10 years (95% CI) was 73.2% (61.1 to 85.3) and 90.1% (86.3 to 93.8) for PR-negative and PR-positive patients, respectively. Stratification of the PR-positive subset resulted in DMFS at 10 years of 87.7% (95% CI: 82.2 to 93.2) and 92.9% (95% CI: 87.8 to 97.9) for MS high and low patients, respectively.

Diagnostic Accuracy and Predictive Values

ROC curves of the continuous MS to predict distant metastasis within 9 years had an AUC (95% CI) of 0.69 (0.58-0.80), 0.65 (0.48-0.82), and 0.69 (0.60-0.79) for ACC, Guy's, and the combined cohort, respectively. ROC curves of the Adjuvant! Online to predict distant metastasis within 9 years had an AUC (95% CI) of 0.71 (0.59-0.83), 0.55 (0.41-0.69), and 0.66 (0.56-0.76) for ACC, Guy's, and the combined cohort, respectively. Visual comparison of the MS and Adjuvant! Online ROC curves for distant metastasis indicate the MS provides additional diagnostic value.

The correlation between the risk of distant metastasis at 9 years as determined from MS and the risk of mortality at 10 years as estimated from Adjuvant! Online was 0.228, 0.166, and 0.201 for ACC, Guy's, and combined set, respectively (because the risk of distant metastasis is tied closely with risk of death, Adjuvant! Online suggested the most appropriate comparisons are between the risk of mortality as estimated by Adjuvant! and the risk of distant metastasis as estimated by expression signature).

Example Seven

Multiplex TaqMan® Assays for the Metastasis Score (MS) (14-Gene Prognosis Signature) and Composite Metastasis Score (cMS) (MS in Combination with Progesterone Receptor (PR))

Overview

Any assay formats for detecting gene expression, particularly those utilizing PCR (including, for example, real-time PCR and/or reverse transcription PCR), can be implemented and used in determining a MS and/or cMS, including, but not limited to, SYBR® Green-based assays and TaqMan® assays. Assays can also utilize microarrays or any other technologies utilized in the art for detecting gene expression. Herein in Example Seven, exemplary MS and cMS based on using TaqMan® assays for detecting gene expression are described.

Metastasis Score (MS)

For gene expression profiling, sample RNAs were first converted to cDNA using a combination of RT primers for each of the assays (primer sequences are provided in Table 37). Five multiplex RT-PCR TaqMan® assays (as indicated by the five pools in Table 37) were used to quantify the mRNA levels of the 14-gene signature (MS) and three housekeeping (HSK) genes (NUP214, PPIG, and SLU7), as well as ER (ESR1), PR (PGR), and HER-2 (ERBB2) (for further information regarding exemplary multiplex TaqMan® assays, including exemplary primers and probes, for detecting ER, PR, and/or HER-2 gene expression, see U.S. patent application publication number US2009/0203015, Ser. No. 12/355, 873, filed Jan. 19, 2009 by Sheng-Yung Chang et al., which is incorporated herein by reference). Each gene in the multiplex was detected with a TaqMan probe that was labeled with a spectrally unique fluorophore (probe sequences are provided in Table 37, and exemplary fluorophores are indicated in Table 37 for each probe). The assays were performed on the Prism 7500 Real-Time PCR system using the following thermocycling parameters for 42 cycles: 50° C. for 2 minutes, 95° C. for 1 minute, 58° C. for 35 minutes, 95° C. for 15 seconds, and 58° C. for 30 seconds. A Universal Human Reference RNA control was amplified with the appropriate multiplex for each run, and all assays were performed in duplicate.

The relative changes in gene expression were calculated by $\Delta\Delta Ct$ method (Livak et al., Methods 2001, 25:402-408). The level of mRNA of each of the 14 profiled genes of the MS is defined as:

$$\Delta\Delta Ct = (Ct_{GOI} - Ct_{EC})_{test\,RNA} - (Ct_{GOI} - Ct_{EC})_{ref\,RNA}$$

where GOI=gene of interest (each of the 14 signature genes that make-up the MS), test RNA=RNA obtained from the patient sample, ref RNA=a calibrator reference RNA, and EC=an endogenous control. The expression level of each signature gene was first normalized to the expression level of the three endogenous control genes (in this example, the three housekeeping genes NUP214, PPIG, and SLU7 were utilized as the control genes). A Ct representing the average of the Cts obtained from amplification of the three endogenous controls ($Ct_{EC}$) can be used to minimize the risk of normalization bias that may occur if only one control gene were used.

The $\Delta\Delta Ct$ value, obtained in gene expression profiling for each of the 14 signature genes, can be used in the following formula to generate a metastasis score ($MS_u$):

$$MS_u = -\left[\sum_{i=1}^{14} Gi\right]$$

($MS_u$ indicates an un-scaled MS)

in which Gi represents the expression level of each gene (i) of the 14-gene prognostic signature (MS). The value of Gi is the ΔΔCt obtained in expression profiling as described above.

Optionally, the $MS_u$ can then be re-scaled. In this example, the $MS_u$ was re-scaled to a 0-40 scale by shifting the scores by 60 and dividing by 2:

$$MS=(MS_u+60)/2$$

where
MS=0 if MS<0
MS=40 if MS>40

A predetermined cutoff point (in this example, MS cutoff=17.5, which is based on MS being re-scaled to a 0-40 scale) was used to determine two categories of prognostic risk for breast cancer metastasis, a low-risk group (MS<17.5) and high-risk group (MS≥17.5).

Composite Metastasis Score (cMS)

A composite score of MS and PR ("cMS") further improves prognosis relative to MS alone, particularly in tamoxifen-treated ER-positive patients. In this exemplary embodiment described herein in Example Seven:

$$cMS_u=\beta_{MS}*MS_u+\beta_{PR}*PR$$

where $\beta_{MS}$=0.0326, $\beta_{PR}$=−0.2034
($cMS_u$ indicates an un-scaled cMS)

95% confidence intervals for these exemplary MS and PR weighted coefficients are provided in Table 36.

Optionally, the $cMS_u$ can then be re-scaled. In this example, the $cMS_u$ was re-scaled to a 0-40 scale by shifting the scores by 3.1175 and multiplying by 10:

$$cMS=(cMS_u+3.1175)*10=0.326*MS_u-2.034*PR+31.175$$

where
cMS=0 if cMS<0
cMS=40 if cMS>40

In this example, the cutoff point between low- and high-risk groups was predefined as cMS cutoff=17.4 (based on cMS being re-scaled to a 0-40 scale) such that a low risk for breast cancer metastasis was determined if cMS<17.4, and a high risk for breast cancer metastasis was determined if cMS≥17.4.

All publications and patents cited in this specification are herein incorporated by reference in their entirety. Various modifications and variations of the described compositions, methods and systems of the invention will be apparent to those skilled in the art without departing from the scope and spirit of the invention. Although the invention has been described in connection with specific preferred embodiments and certain working examples, it should be understood that the invention as claimed should not be unduly limited to such specific embodiments. Indeed, various modifications of the above-described modes for carrying out the invention that are obvious to those skilled in the field of molecular biology, genetics and related fields are intended to be within the scope of the following claims.

TABLE 1

Clinical and pathological characteristics of patients from CPMC and Guy's Hospital
Clinical and pathological characteristics of node-negative, ER-positive, untreated patients

| Characteristics | Training (UCSF) n = 142 | Validation (Guy's) n = 280 |
|---|---|---|
| Age | | |
| ≤55 yrs | 40 (28.2%) | 144 (51.4%) |
| >55 yrs | 102 (71.8%) | 136 (48.6%) |
| Mean (Std. dev.) | 62 yrs (12.6) | 55.5 yrs (11.6) |
| Min.-Max. | 31 yrs-89 yrs | 29 yrs-87 yrs |
| Tumor diameter | | |
| ≤2 cm | 126 (88.7%) | 167 (59.6%) |
| >2 cm | 8 (5.6%) | 113 (40.4%) |
| Missing | 8 (5.6%) | 0 (0%) |
| Mean (Std. Dev.) | 1.28 cm (0.50) | 1.93 cm (0.85) |
| Tumor grade | | |
| Grade 1 | 74 (52.1%) | 60 (21.4%) |
| Grade 2 | 61 (43%) | 166 (59.3%) |
| Grade 3 | 4 (2.8%) | 54 (19.3%) |
| Missing | 3 (2.1%) | 0 (0%) |
| Stage | | |
| I | 117 (82.4%) | 167 (59.6%) |
| IIA | 25 (17.6%) | 113 (40.4%) |
| Distant Recurrence | | |
| Yes | 31 (21.8%) | 66 (23.4%) |
| No | 111 (78.2%) | 214 (76.6%) |
| Death of all cause | | |
| Yes | 56 (39.4%) | 135 (48.2%) |
| No | 86 (60.6%) | 145 (51.8%) |
| Median follow up | 8.7 yrs | 15.6 yrs |

TABLE 2

Genes/transcripts comprising the 14-gene metastasis score (MS), and endogenous controls.

| Gene | MS constant ai | Ref Seq | Description | Reference |
|---|---|---|---|---|
| CENPA | 0.29 | NM_001809 | centromere protein A, 17 kDa | Black, B. E., Foltz, D. R., et al., Nature 430(6999): 578-582 (2004) |
| PKMYT1 | 0.29 | NM_004203 | membrane associated tyrosine- and thereonine-specific cdc2-inhibitory kinase | Bryan, B. A., Dyson, O. F. et al., J. Gen. Virol. 87 (PT 3), 519-529 (2006) |
| MELK | 0.29 | NM_014791 | maternal embryonic leucine zipper kinase | Beullens, M., Vancauwenbergh, S. et al., J. Biol. Chem. 280 (48), 40003-40011 (2005) |
| MYBL2 | 0.29 | NM_002466 | v-myb myeloblastosis viyal oncogene homolog (avian)-like 2 | Bryan, B. A., Dyson, O. F. et al., J. Gen. Virol. 87 (PT 3), 519-529 (2006) |

TABLE 2-continued

Genes/transcripts comprising the 14-gene metastasis score (MS), and endogenous controls.

| Gene | MS constant ai | Ref Seq | Description | Reference |
|---|---|---|---|---|
| BUB1 | 0.27 | NM_004366 | BUB1 budding uninhibited by benzimidazoles 1 homolog | Morrow, C. J., Tighe, A. et al., *J. Cell. Sci.* 118 (PT 16), 3639-3652 (2005) |
| RACGAP1 | 0.29 | NM_013277 | Rac GTPase activating protein 1 | Niiya, F., Xie, X. et al., *J. Biol. Chem.* 280 (43), 36502-36509 (2005) |
| TK1 | 0.27 | NM_003258 | thymidine kinase 1, soluble | Karbownik, M., Brzezianska, E. et al., *Cancer Lett.* 225 (2), 267-273 (2005) |
| UBE2S | 0.27 | NM_014501 | ubiquitin-conjugating enzyme E2S | Liu, Z., Diaz, L. A. et al., *J. Biol. Chem.* 267 (22), 15829-15835 (1992) |
| DC13 | 0.22 | AF201935 | DC13 protein | Gu, Y., Peng, Y. et al., Direct Submission, Submitted (05-NOV-1999) Chinese National Human Genome Center at Shanghai, 351 Guo Shoujing Road, Zhangjiang Hi-Tech Park, Pudong, Shanghai 201203, P. R. China |
| RFC4 | 0.25 | NM_002916 | replication factor C (activator 1) 4, 37 kDa | Gupte, R. S., Weng, Y. et al., *Cell Cycle* 4 (2), 323-329 (2005) |
| PRR11 (FLJ11029) | 0.26 | NM_018304 | proline rich 11 | Weinmann, A. S., Yan, P. S. et al., *Genes Dev.* 16 (2), 235-244 (2002) |
| DIAPH3 | 0.23 | NM_030932 | diaphanous homolog 3 (*Drosophila*) | Katoh, M. and Katoh, M., *Int. J. Mol. Med.* 13 (3), 473-478 (2004) |
| ORC6L | 0.28 | NM_014321 | origin recognition complex, subunit 6 homolog-like (yeast) | Sibani, S., Price, G. B. et al., *Biochemistry* 44 (21), 7885-7896 (2005) |
| CCNB1 | 0.23 | NM_031966 | cyclin B1 | Zhao, M., Kim, Y. T. et al., *Exp Oncol* 28 (1), 44-48 (2006) |
| PPIG | EC | NM_004792 | peptidylprolyl isomerase G | Lin, C. L., Leu, S. et al., *Biochem. Biophys. Res. Commun.* 321 (3), 638-647 (2004) |
| NUP214 | EC | NM_005085 | nucleoporin 214 kDa | Graux, C., Cools, J. et al., *Nat. Genet.* 36 (10), 1084-1089 (2004) |
| SLU7 | EC | NM_006425 | step II splicing factor | Shomron, N., Alberstein, M. et al., *J. Cell. Sci.* 118 (PT 6), 1151-1159 (2005) |

NOTE:
PCR primers for expression profiling of all genes disclosed herein were designed to amplify all transcript variants known at time of filing.
EC = Endogenous Control.
Ref Seq = NCBI reference sequence for one variant transcript of this gene.

TABLE 3

Exemplary primers for gene expression profiling.

| Gene | Sequence | SEQ ID | Orientation |
|---|---|---|---|
| BUB1 | CATGGTGGTGCCTTCAA | SEQ ID NO: 1 | Upper |
| CCNB1 | GCCAAATACCTGATGGAACTAA | SEQ ID NO: 3 | Upper |
| CENPA | CAGTCGGCGGAGACAA | SEQ ID NO: 5 | Upper |
| DC13 | AAAGTGACCTGTGAGAGATTGAA | SEQ ID NO: 7 | Upper |
| DIAPH3 | TTATCCCATCGCCTTGAA | SEQ ID NO: 9 | Upper |
| MELK | AGAGACGGGCCCAGAA | SEQ ID NO: 11 | Upper |
| MYBL2 | GCGGAGCCCCATCAA | SEQ ID NO: 13 | Upper |
| ORC6L | CACTTCTGCTGCACTGCTTT | SEQ ID NO: 15 | Upper |
| PKMYT1 | CTACCTGCCCCCTGAGTT | SEQ ID NO: 17 | Upper |
| PRR11 | TGTCCAAGCTGTGGTCAAA | SEQ ID NO: 19 | Upper |
| RACGAP1 | GACTGCGAAAAGCTGGAA | SEQ ID NO: 21 | Upper |
| RFC4 | TTTGGCAGCAGCTAGAGAA | SEQ ID NO: 23 | Upper |
| TK1 | GATGGTTTCCACAGGAACAA | SEQ ID NO: 25 | Upper |
| UBE2S | CCTGCTGATCCACCCTAA | SEQ ID NO: 27 | Upper |
| NUP214 | CACTGGATCCCAAGAGTGAA | SEQ ID NO: 29 | Upper |
| PPIG | TGGACAAGTAATCTCTGGTCAA | SEQ ID NO: 31 | Upper |
| SLU7 | TGCCAATGCAGGAAAGAA | SEQ ID NO: 33 | Upper |
| BUB1 | GCTGAATACATGTGAGACGACAA | SEQ ID NO: 2 | Lower |
| CCNB1 | CTCCTGCTGCAATTTGAGAA | SEQ ID NO: 4 | Lower |
| CENPA | AAGAGGTGTGTGCTCTTCTGAA | SEQ ID NO: 6 | Lower |
| DC13 | CGCCCTGCCCAACAA | SEQ ID NO: 8 | Lower |
| DIAPH3 | TGCTCCACACCATGTTGTAA | SEQ ID NO: 10 | Lower |
| MELK | CAACAGTTGATCTGGATTCACTAA | SEQ ID NO: 12 | Lower |
| MYBL2 | CATCCTCATCCACAATGTCAA | SEQ ID NO: 14 | Lower |
| ORC6L | GGATGTGGCTACCATTTTGTTT | SEQ ID NO: 16 | Lower |
| PKMYT1 | AGCATCATGACAAGGACAGAA | SEQ ID NO: 18 | Lower |
| PRR11 | TCTCCAGGGGTGATCAGAA | SEQ ID NO: 20 | Lower |
| RACGAP1 | TTGCTCCTCGCTTAGTTGAA | SEQ ID NO: 22 | Lower |

TABLE 3-continued

Exemplary primers for gene expression profiling.

| Gene | Sequence | SEQ ID | Orientation |
|---|---|---|---|
| RFC4 | CACGTTCATCAGATGCATTTAA | SEQ ID NO: 24 | Lower |
| TK1 | GGATCCAAGTCCCAGCAA | SEQ ID NO: 26 | Lower |
| UBE2S | GCATACTCCTCGTAGTTCTCCAA | SEQ ID NO: 28 | Lower |
| NUP214 | TGATCCCACTCCAAGTCTAGAA | SEQ ID NO: 30 | Lower |
| PPIG | GTATCCGTACCTCCGCAAA | SEQ ID NO: 32 | Lower |
| SLU7 | TGGTATCTCCTGTGTACCTAACAAA | SEQ ID NO: 34 | Lower |

TABLE 4

Mean (μ) and standard deviation (σ) of gene expression levels of the 14 genes in the signature in 142 samples from CPMC (ai are the loadings on the first principal components)

| Gene | ai | μ | σ |
|---|---|---|---|
| CENPA | 0.29 | −0.18 | 1.40 |
| TK1 | 0.27 | −1.07 | 1.68 |
| BUB1 | 0.27 | 2.69 | 1.78 |
| PRR11 | 0.26 | 5.25 | 1.90 |
| UBE2S | 0.27 | 2.64 | 1.41 |
| DC13 | 0.22 | 0.47 | 1.15 |
| DIAPH3 | 0.23 | 1.90 | 1.34 |
| MELK | 0.29 | −1.77 | 1.41 |
| MYBL2 | 0.29 | 2.54 | 1.88 |
| PKMYT1 | 0.29 | −0.35 | 1.73 |
| RFC4 | 0.25 | 1.25 | 0.99 |
| ORC6L | 0.28 | 1.98 | 1.43 |
| RACGAP1 | 0.29 | 4.00 | 1.09 |
| CCNB1 | 0.23 | 3.20 | 1.66 |

TABLE 5

Distant metastasis-free and overall survival rates for low-risk and high-risk prognosis group at 5 and 10 years for patients from CPMC

| Group | No. of patients | Metastsis-free survival rate 5-yr (std. error) | Metastsis-free survival rate 10-yr (std. error) | Overall survival rate 5-yr (std. error) | Overall survival rate 10-yr (std. error) |
|---|---|---|---|---|---|
| Low risk | 71 | 0.96 (0.025) | 0.90 (0.037) | 0.90 (0.036) | 0.78 (0.059) |
| High risk | 71 | 0.74 (0.053) | 0.62 (0.066) | 0.79 (0.049) | 0.48 (0.070) |
| All | 142 | 0.85 (0.031) | 0.76 (0.040) | 0.84 (0.031) | 0.63 (0.048) |

TABLE 6

Univariate and multivariate Cox proportional hazard regression analyses of 14-gene prognostic signature, tumor size, tumor grade and age for patients from CPMC

| Variable | Univariate analysis Hazard ratio (95% CI) | P Value | Multivariate analysis Hazard ratio (95% CI) | P Value |
|---|---|---|---|---|
| 14-gene signature | 4.23 (1.82-9.85) | 0.0008 | 3.26 (1.26-8.38) | 0.014 |
| Age | 1.00 (0.97-1.03) | 0.850 | 1.00 (0.98-1.03) | 0.810 |
| Tumor size | 1.07 (1.00-1.14) | 0.050 | 1.03 (0.96-1.10) | 0.450 |
| Tumor grade (moderate + high) | 2.18 (1.04-4.59) | 0.040 | 1.26 (0.55-2.87) | 0.580 |

For 14-gene prognostic signature, hazard ratio compares high-risk vs. low-risk groups using median MS (CV) to classify patients. For age, hazard ratio is given as the hazard increase for each year increase in age. For tumor size, hazard ratio is given as hazard increase per each centimeter increase in diameter. For tumor grade, hazard of the group with medium and high-grade tumors vs. low-grade tumors.

TABLE 7

| Gene | M value |
|---|---|
| PPIG | 0.8046 |
| SLU7 | 0.8741 |
| NUP214 | 0.8886 |
| PPP1CA | 1.0256 |
| TERF2 | 1.1907 |
| EEF1A1 | 1.1994 |

TABLE 8

| Gene | M value |
|---|---|
| PPIG | 0.5697 |
| NUP214 | 0.5520 |
| SLU7 | 0.6075 |

TABLE 9

Prognostic values of the molecular prognostic signature using median MS (CV) as cut point to predict distant metastasis within 5 years and metastasis-free in more than 5 years for patients from CPMC (A). Distant metastasis within 5 years - prognosis vs. actual outcome

| Group | Distant Metastasis Within 5 yr (n = 21) | Disease-free >5 yr (n = 95) |
|---|---|---|
| High risk by MS | 18 | 39 |
| Low risk by MS | 3 | 56 |

TABLE 9-continued

Prognostic values of the molecular prognostic
signature using median MS (CV)
as cut point to predict distant metastasis within
5 years and metastasis-free in more than 5 years
for patients from CPMC (B). Diagnostic metrics of prognosis signature
to predict distant metastasis within 5 years

| | Value | 95% CI |
|---|---|---|
| Sensitivity | 0.86 | 0.65-0.95 |
| Specificity | 0.59 | 0.49-0.63 |
| Odds ratio | 8.62 | 2.37-31.26 |
| PLR | 2.09 | 1.55-2.81 |
| NLR | 0.24 | 0.084-0.70 |
| PPV* | 0.26 | 0.21-0.33 |
| NPV* | 0.96 | 0.89-0.99 |

*Predictive values were calculated with prevalence of distant metastasis at 5 years estimated to be 0.15 from the current data.
**Individuals with distant metastasis in more than 5 years and those censored before 5 years were not included.
PLR—positive likelihood ratio, NLR—negative likelihood ratio,
PPV—positive predictive value, NPV—negative predictive value

TABLE 10

Hazard ratios (unadjusted) (with 95% confidence interval) and p values for
various risk classification for untreated patients from Guy's Hospital

| Classification | Time to distant metastases | Overall Survival |
|---|---|---|
| Gene signature | 6.12 (2.23-16.83) | 2.49 (1.50-4.14) |
| (high risk vs. low risk) | p = 0.0004 | p = 0.0004 |
| Adjuvant! | 2.63 (1.30-5.32) | 2.89 (1.71-4.87) |
| (high risk vs. low risk) | p = 0.007 | p < 0.0001 |
| Age (≤55 yr vs. >55 yr) | 1.45 (0.89-2.36) | 2.91 (2.03-4.18) |
| | p = 0.13 | p < 0.0001 |
| Tumor size (T2 vs. T1) | 2.27 (1.39-3.69) | 1.60 (1.14-2.25) |
| | p = 0.001 | p = 0.0062 |
| Histologic grade | 2.56 (1.17-5.61) | 2.56 (1.44-4.54) |
| (grade 2 + 3 vs. grade 1) | p = 0.019 | p = 0.0013 |

TABLE 11

Univariate and multivariate Cox model of time to distant metastases for 14-gene
prognostic signature, tumor size, tumor grade and age for untreated patients from Guy's Hospital Table 11a Univariate and multivariate Cox model of time to distant metastases (DMFS) for
14-gene prognostic signature, tumor size, tumor grade and age

| | Univariate analysis | | Multivariate analysis | |
|---|---|---|---|---|
| Variable | Hazard ratio (95% CI) | p-value | Hazard ratio (95% CI) | p-value |
| 14-gene signature | 6.12 (2.23-16.83) | 0.0004 | 4.81 (1.71-13.53) | 0.003 |
| Age | 1.03 (1.00-1.05) | 0.024 | 1.01 (0.99-1.04) | 0.251 |
| Tumor size | 1.74 (1.24-2.44) | 0.001 | 1.39 (0.97-2.00) | 0.076 |
| Grade 2 | 2.45 (1.10-5.43) | 0.028 | 1.43 (0.63-3.23) | 0.390 |
| Grade 3 | 2.98 (1.21-7.30) | 0.017 | 1.40 (0.55-3.53) | 0.478 |

Table 11b Univariate and multivariate Cox model of time to distant metastases (DMFS) for
risk groups by MS and by Adjuvant!

| | Univariate analysis | | Multivariate analysis | |
|---|---|---|---|---|
| Variable | Hazard ratio (95% CI) | p-value | Hazard ratio (95% CI) | p-value |
| 14-gene signature | 6.12 (2.23-16.83) | 0.0004 | 5.32 (1.92-14.73) | 0.001 |
| Adjuvant! | 2.63 (1.30-5.32) | 0.007 | 2.06 (1.02-4.19) | 0.045 |

For 14-gene prognostic signature, hazard ratio compares high-risk vs. low-risk groups using formerly defined zero MS as cutpoint to classify patients. For age, hazard ratio is given as the hazard increase for each year increase in age. For tumor size, hazard ratio is given as hazard increase per each centimeter increase in diameter. For tumor grade, hazards of the groups with grade 2 and grade 3 tumors were compared to grade 1 tumors.
For 14-gene prognostic signature, hazard ratio compares high-risk vs. low-risk groups using formerly defined zero MS as cutpoint to classify patients. For Adjuvant!, hazard ratio compares high-risk vs low-risk groups using cut point of 20% relapse probability in 10 years as calcuated by Adjuvant! Online program.

TABLE 12

Distant metastasis free and overall survival rates for low-risk and high-risk groups by MS
at 5 and 10 years for untreated patients from Guy's Hospital
Distant metastasis-free and overall survival rates for low-risk and
high-risk prognosis group by MS at 5 and 10 years

| | | Metastsis-free survival rate | | Overall survival rate | |
|---|---|---|---|---|---|
| Group | No. of patients | 5-yr (std. error) | 10-yr (std. error) | 5-yr (std. error) | 10-yr (std. error) |
| Low risk | 71 | 0.99 (0.014) | 0.96 (0.025) | 0.97 (0.020) | 0.94 (0.028) |
| High risk | 209 | 0.86 (0.025) | 0.76 (0.031) | 0.92 (0.019) | 0.71 (0.032) |
| All | 280 | 0.89 (0.019) | 0.81 (0.024) | 0.93 (0.015) | 0.77 (0.026) |

TABLE 13

Subgroup analyses: hazard ratio of MS risk groups for time to distant metastases (DMFS) in different subgroups of Adjuvant!, histological grade, tumor size, age and menopausal status for untreated patients from Guy's Hospital

|  | no. of patients | no. of events | Hazard ratio of MS risk group (95% CI) | p-value |
|---|---|---|---|---|
| Adjuvant! | | | | |
| High risk | 205 | 57 | 3.72 (1.34-10.28) | 0.0114 |
| Low risk | 75 | 9 | Infinity* | 0.01 |
| Tumor grade | | | | |
| High grade (grade 2, 3) | 220 | 59 | 4.59 (1.44-14.67) | 0.010 |
| Low grade (grade 1) | 60 | 7 | 7.58 (0.91-63.08) | 0.061 |
| Tumor size | | | | |
| ≤2 cm | 167 | 28 | 14.16 (1.92-104.22) | 0.009 |
| >2 cm | 113 | 38 | 2.64 (0.81-8.58) | 0.110 |
| Age | | | | |
| ≤55 yrs | 144 | 30 | 13.58 (1.85-99.74) | 0.010 |
| >55 yrs | 136 | 36 | 3.45 (1.06-11.26) | 0.040 |
| Menopausal status | | | | |
| Premenopausal | 102 | 21 | 7.85 (1.05-58.49) | 0.044 |
| Postmenopausal | 157 | 40 | 4.88 (1.51-15.84) | 0.008 |

*34 MS low-risk with 0 events and 41 MS high-risk with 9 events

TABLE 14

Diagnostic accuracy and predictive values of MS and Adjuvant! risk groups for distant metastases within 10 years for untreated patients from Guy's Hospital

| Risk Classification | Distant Metastases within 10 years | | | |
|---|---|---|---|---|
| | Sensitivity 95% CI | Specificity 95% CI | PPV 95% CI | NPV 95% CI |
| MS risk group | 0.94 (0.84-0.98) | 0.3 (0.24-0.37) | 0.23 (0.21-0.25) | 0.97 (0.88-0.99) |
| Adjuvant! risk group | 0.90 (0.78-0.96) | 0.31 (0.26-0.38) | 0.23 (0.20-0.25) | 0.93 (0.85-0.97) |

TABLE 15

Clinical and Pathological Characteristics of both Untreated and Treated Patients from University of Muenster

| Characteristics | All Patients N = 96 | All Treated N = 62 | Tamoxifen Treated Only N = 54 |
|---|---|---|---|
| Age | | | |
| Mean (SD) | 56.64 (12.6) | 56.43 (12.4) | 57.63 (12.1) |
| >55 yrs | 38 (40.6%) | 26 (41.9%) | 26 (48.1%) |
| <55 yrs | 37 (38.5%) | 27 (43.5%) | 22 (40.7%) |
| Unknown | 20 (20.8%) | 9 (14.5%) | 6 (11.1%) |
| T Stage | | | |
| 1 | 56 (58.3%) | 37 (59.7%) | 33 (61.1%) |
| 1C | 1 (1.0%) | 1 (1.6%) | 1 (1.9%) |
| 2 | 37 (38.5%) | 22 (35.5%) | 18 (33.3%) |
| Unknown | 2 (2.1%) | 2 (3.2%) | 2 (3.7%) |
| Grade | | | |
| Poor | 15 (15.6%) | 11 (17.7%) | 9 (16.7%) |
| Moderate | 41 (42.7%) | 31 (50.0%) | 25 (46.3%) |
| Good | 9 (9.4%) | 6 (9.7%) | 6 (11.1%) |
| Unknown | 31 (32.3%) | 14 (22.6%) | 14 (25.9%) |
| Distant Metastasis | | | |
| Yes | 27 (28.1%) | 16 (25.8%) | 14 (25.9%) |
| Follow Up | | | |
| Median (months) | 60 | 70.4 | 66.5 |

TABLE 16

Distant-metastasis-free survival rates in MS high-risk and low-risk patients from University of Muenster

| Groups | No. of Patients | Risk Group | No. of Patients | 5-yr DMFS Rate (SE) |
|---|---|---|---|---|
| All Patients | 96 | High | 48 | 0.61 (0.072) |
| | | Low | 48 | 0.88 (0.052) |
| All Treated | 62 | High | 32 | 0.66 (0.084) |
| | | Low | 30 | 0.89 (0.060) |
| Tamoxifen Treated Alone | 54 | High | 26 | 0.65 (0.084) |
| | | Low | 28 | 0.88 (0.065) |

TABLE 17

Clinical and pathological characteristics of patients from 205 treated patients from Guy's Hospital

| Characteristics | Node-negative ER-positive (n = 205) |
|---|---|
| Menopausal Status | |
| Premenopausal | 31 (15.12%) |
| Perimenopausal | 4 (1.95%) |
| Postmenopausal | 165 (80.49%) |
| Unknown | 5 (2.44%) |
| Age | |
| ≤55 yrs | 74 (36.1%) |
| >55 yrs | 131 (63.9%) |
| Mean (Std. dev.) | 59.3 (10.4) |
| Min. - Max. | 33-86 |
| Tumor diameter | |
| ≤2 cm | 138 (67.32%) |
| >2 cm | 67 (32.68%) |
| Mean (Std. Dev.) | 1.67 (1.0) |
| Min. - Max. | 0-3.0 |
| Histological Grade | |
| Grade 1 | 60 (29.27%) |
| Grade 2 | 98 (47.8%) |
| Grade 3 | 47 (22.93%) |
| Stage | |
| I | 138 (67.32%) |
| II | 67 (32.68%) |
| Subtypes | |
| Ductal NOS | 164 (80.0%) |
| Lobular Classic | 22 (10.73%) |
| Lobular Varient | 3 (1.46%) |
| Tubular | 8 (3.9%) |
| Mucinous | 6 (2.93%) |
| Papillary | 1 (0.49%) |
| Apocrine | 1 (0.49%) |
| Distant Recurrence | |
| Yes | 17 (8.29%) |
| No | 188 (91.71%) |

TABLE 17-continued

Clinical and pathological characteristics of patients from 205 treated patients from Guy's Hospital

| Characteristics | Node-negative ER-positive (n = 205) |
|---|---|
| Any Recurrence | |
| Yes | 17 (8.9%) |
| No | 188 (91.71%) |
| Death (Any cause) | |
| Yes | 44 (21.46%) |
| No | 161 (78.54%) |
| Death (Breast Cancer) | |
| Yes | 16 (7.8%) |
| No | 189 (92.20%) |
| Median follow up | 9.3 yrs |

TABLE 18

Five-year and ten-year distant-metastasis-free survival rates in high, intermediate, and low MS groups in Guy's treated samples

| | No. of Patients | DM | 5 yr DMFS (SE) | 10 yr DMFS (SE) |
|---|---|---|---|---|
| High | 40 | 7 | 0.872 (0.054) | 0.804 (0.068) |
| Intermediate | 29 | 2 | 0.966 (0.034) | 0.966 (0.034) |
| Low | 136 | 8 | 0.970 (0.015) | 0.921 (0.028) |
| Int. + Low | 165 | 10 | 0.969 (0.014) | 0.928 (0.025) |
| All | 205 | 17 | 0.950 (0.015) | 0.904 (0.0239) |

TABLE 19

Univariate and multivariate Cox proportional hazard regression of MS risk groups, age, tumor size, and histological grade in Guy's treated samples

| | Univariate | | | Multivariate | | |
|---|---|---|---|---|---|---|
| | Hazard Ratio | 95% Cl | P-value | Hazard Ratio | 95% Cl | P-value |
| MS high vs. low risk | 3.25 | 1.24-8.54 | 0.017 | 5.82 | 1.71-19.75 | 0.0047 |
| Age (per year) | 1.03 | 0.98-1.08 | 0.27 | 1.03 | 0.98-1.08 | 0.31 |
| Tumor size (per cm) | 1.28 | 0.77-2.14 | 0.34 | 1.17 | 0.68-2.03 | 0.57 |
| Grade 2 vs. Grade 1 | 3.50 | 0.78-15.79 | 0.10 | 2.64 | 0.56-12.45 | 0.22 |
| Grade 3 vs. Grade 1 | 2.72 | 0.50-14.86 | 0.25 | 0.62 | 0.081-4.76 | 0.65 |

TABLE 20

Association of MS risk groups with age, tumor size and histological grade in Guy's treated patients

| | N | Mean | Std. Dev. |
|---|---|---|---|
| Age | | | |
| High | 40 | 59.3 | 8.3 |
| Int. + Low | 165 | 59.3 | 10.8 |
| One-way ANOVA | | p = 0.34 | |
| Tumor Size | | | |
| High | 40 | 1.87 | 0.92 |
| Int. + Low | 165 | 1.61 | 101 |
| One-way ANOVA | | p = 0.14 | |

TABLE 20-continued

Association of MS risk groups with age, tumor size and histological grade in Guy's treated patients

| Histological grade | Grade 1 | Grade 2 | Grade 3 |
|---|---|---|---|
| High | 0 | 9 | 31 |
| Int. + Low | 60 | 89 | 16 |
| Crammer's V = 0.65 | chi-sq test for association p-value <0.0001 | | |

TABLE 21

Performance of MS risk groups (High vs. low risk) in subgroups of age, tumor size, histological grade and menopausal status

| | N patient | N DM | HR | L95% Cl | U95% CL | P-Value |
|---|---|---|---|---|---|---|
| All | 205 | 17 | 3.25 | 1.24 | 8.54 | 0.017 |
| Histologic Grade | | | | | | |
| Grade 1 | 60 | 2 | NA | only low score | | |
| Grade 2 | 98 | 11 | 10.72 | 3.00 | 38.36 | 0.0003 |
| Grade 3 | 47 | 4 | 1.53 | 0.16 | 14.66 | 0.715 |
| Tumor size | | | | | | |
| <=2 cm | 138 | 11 | 3.66 | 1.07 | 12.57 | 0.0392 |
| >2 cm | 67 | 6 | 2.99 | 0.60 | 14.82 | 0.18 |
| Age | | | | | | |
| <=55 yrs | 74 | 5 | 7.38 | 1.00 | 54.66 | 0.0503 |
| >55 yrs | 131 | 12 | 2.78 | 0.88 | 8.75 | 0.0813 |
| Menopausal Status | | | | | | |
| premenopausal | 31 | 1 | NA | | | |
| postmenopausal | 165 | 15 | 2.84 | 1.01 | 7.99 | 0.0476 |

TABLE 22

Diagnostic values of MS risk groups (high vs. low risk) in Guy's treated samples

| | 5 yr | 10 yr |
|---|---|---|
| Sensitivity | 0.50 (0.24-0.76) | 0.44 (0.23-0.67) |
| Specificity | 0.82 (0.76-0.87) | 0.85 (0.76-0.92) |
| PPV | 0.128 (0.068-0.227) | 0.24 (0.13-0.41) |
| NPV | 0.969 (0.944-0.983) | 0.93 (0.90-0.96) |

TABLE 23

Clinicopathological characteristics of 234 Japanese samples

| | Post-menopause 112 (47.9%) | Pre-menopause 122 (52.1%) | All 234 (100%) |
|---|---|---|---|
| Age | | | |
| <=55 yrs | 32 (28.6%) | 122 (100%) | 154 (65.8%) |
| >55 yrs | 80 (71.4%) | 0 (0%) | 80 (34.2%) |
| Mean (Std. dev.) | 60.8 (7.8) | 44.8 (6.0) | 52.5 (10.6) |
| Min. - Max. | 43-81 | 25-54 | 25-81 |
| Tumor diameter | | | |
| <=2 cm | 65 (58.0%) | 81 (66.4%) | 146 (62.4%) |
| >2 cm | 47 (42.0%) | 41 (33.6%) | 88 (37.6%) |
| Mean (Std. Dev.) | 2.15 (1.0) | 1.96 (1.2) | 2.05 (1.1) |
| Min. - Max. | 0.3-8.4 | 0.1-6.5 | 0.1-8.4 |

TABLE 23-continued

Clinicopathological characteristics of 234 Japanese samples

|  | Post-menopause 112 (47.9%) | Pre-menopause 122 (52.1%) | All 234 (100%) |
|---|---|---|---|
| Histologic grade | | | |
| Grade 1 | 28 (25%) | 46 (37.7%) | 74 (31.6%) |
| Grade 2 | 56 (50%) | 57 (46.7%) | 113 (48.3%) |
| Grade 3 | 28 (25%) | 19 (15.6%) | 47 (20.1%) |
| Tumor subtype | | | |
| II a Papillotubular | 42 (37.5%) | 66 (54.1%) | 108 (46.2%) |
| II a Scirrhous | 41 (36.6%) | 36 (29.5%) | 77 (32.9%) |
| II a Solid-tubular | 24 (21.4%) | 14 (11.5%) | 38 (16.2%) |
| II b Invasive Lobular | 2 (1.8%) | 2 (1.6%) | 4 (1.7%) |
| II b Medullary | 1 (0.9%) | 0 (0%) | 1 (0.4%) |
| II b Mucinous | 2 (1.8%) | 4 (3.3%) | 6 (2.6%) |
| Stage | | | |
| I | 65 (58.0%) | 81 (66.4%) | 146 (62.4%) |
| IIA | 44 (39.3%) | 36 (29.5%) | 80 (34.2%) |
| IIB | 3 (2.7%) | 5 (4.1%) | 8 (3.4%) |
| PgR | | | |
| + | 65 (58%) | 113 (92.6%) | 178 (76.1%) |
| − | 47 (42%) | 9 (7.4%) | 56 (23.9%) |
| Therapy | | | |
| Tam/Tam comb. | 112 (100%) | 102 (83.9%) | 214 (91.5%) |
| ZOL | 0 (0%) | 20 (16.1%) | 20 (8.5%) |
| Distant Metastasis | | | |
| Yes | 21 (18.8%) | 10 (8.9%) | 31 (13.3%) |
| No | 91 (81.3%) | 112 (91.1%) | 203 (86.8%) |
| Death of Any Cause | | | |
| Yes | 10 (8.9%) | 9 (7.3%) | 19 (8.1%) |
| No | 102 (90.9%) | 115 (92.7%) | 215 (91.9%) |
| Recurrence (local and distant) | | | |
| Yes | 30 (26.8%) | 16 (13.1%) | 46 (19.7%) |
| No | 82 (73.2%) | 106 (86.9%) | 188 (80.%) |
| Follow-up (years) | | | |
| Median | 9 | 8 | 8.7 |
| High | 95 | 0.808 (0.042) | 0.747 (0.050) |

TABLE 24

Five-year and ten-year distant-metastasis-free survival rates in different MS groups in Japanese patients

| | No. of Patients | 5 yr DMFS (SE) | 10 yr DMFS (SE) |
|---|---|---|---|
| Intermediate | 62 | 0.965 (0.024) | 0.912 (0.044) |
| Low | 77 | 0.974 (0.018) | 0.887 (0.047) |
| Int. + Low | 139 | 0.97 (0.015) | 0.895 (0.034) |
| All | 234 | 0.905 (0.020) | 0.837 (0.029) |

TABLE 25

Univariate and multivariate Cox proportional hazard model of time to distant metastases for MS risk groups, age, tumor size and histological grade in Japanese patients

| | Univariate | | | Multivariate | | |
|---|---|---|---|---|---|---|
| | Hazard Ratio | 95% Cl | P-value | Hazard Ratio | 95% Cl | P-value |
| MS high vs. int. + low | 3.32 | 1.56-7.06 | 0.0018 | 3.79 | 1.42-10.1 | 0.0078 |
| Age (per year) | 1.04 | 1.00-1.08 | 0.032 | 1.03 | 0.99-1.07 | 0.087 |
| Tissue Size (per cm) | 1.45 | 1.14-1.83 | 0.0024 | 1.4 | 1.10-1.78 | 0.007 |
| Hist. grade 2 vs. 1 | 1.47 | 0.60-3.61 | 0.40 | 0.72 | 0.24-2.14 | 0.56 |
| Hist. grade 3 vs. 1 | 2.02 | 0.75-5.44 | 0.16 | 0.55 | 0.15-2.00 | 0.36 |

TABLE 26

Association of MS risk groups with age, tumor size and histological grade in Japanese patients

| | N | Mean | Std. Dev. |
|---|---|---|---|
| Age | | | |
| High | 95 | 53.4 | 10.4 |
| Int. + Low | 139 | 51.9 | 10.7 |
| One-way ANOVA | | p = 0.29 | |
| Tumor Size | | | |
| High | 95 | 2.23 | 1.04 |
| Int. + Low | 139 | 1.93 | 1.13 |
| One-way ANOVA | | p = 0.037 | |

| Histologic grade | Grade 1 | Grade 2 | Grade 3 |
|---|---|---|---|
| High | 4 | 54 | 37 |
| Int. + Low | 70 | 59 | 10 |
| Crammer's V = 0.54 | chi-sq test for association p-value < 0.0001 | | |

| Subtype | 2a Papillotular | 2a Scirrhous | 2a Solid-tubular | 2b Invasive lobular | Medullary | Mucinous |
|---|---|---|---|---|---|---|
| High | 45 | 23 | 24 | 1 | 1 | 1 |
| Int. + Low | 63 | 54 | 14 | 3 | 0 | 5 |
| Crammer's V = 0.25 | chi-sq test for association p-value = 0.01 | | | | | |

TABLE 27

Univariate and multivariate Cox proportional hazard model of time to distant metastases for MS risk groups, menopausal status, tumor size, PgR status and histological grade in Japanese patients

| | Univariate | | | Multivariate | | |
|---|---|---|---|---|---|---|
| | Hazard Ratio | 95% Cl | P-value | Hazard Ratio | 95% Cl | P-value |
| MS high vs. int. + low | 3.32 | 1.56-7.06 | 0.0018 | 3.44 | 1.27-9.34 | 0.015 |
| Pre, Tam vs. Post, Tam | 0.33 | 0.13-0.81 | 0.016 | 0.45 | 0.17-1.19 | 0.11 |
| Pre, ZOL vs. Post, Tam | 1.22 | 0.42-3.58 | 0.72 | 1.8 | 0.55-5.81 | 0.33 |
| Tissue_size (per cm) | 1.45 | 1.14-1.83 | 0.0024 | 1.45 | 1.12-1.88 | 0.0049 |
| PgR (−ve vs. +ve) | 2.3 | 1.13-4.7 | 0.022 | 1.7 | 0.75-3.86 | 0.2 |
| Hist. grade 2 vs. 1 | 1.47 | 0.6-3.61 | 0.4 | 0.53 | 0.17-1.62 | 0.26 |
| Hist. grade 3 vs. 1 | 2.02 | 0.75-5.44 | 0.16 | 0.49 | 0.13-1.76 | 0.27 |

TABLE 28

Subgroup analyses: hazard ratio of MS risk groups for time to distant metastases (DMFS) in different subgroups of tumorsize, age, menopausal status, histological grade and PgR status

| Strata | Hazard Ratio | 95% CI | P-value |
|---|---|---|---|
| ALL | 3.32 | 1.56-7.06 | 0.0018 |
| Tumor <=2 cm | 4.48 | 1.16-17.34 | 0.030 |
| Tumor >2 cm | 2.27 | 0.92-5.62 | 0.077 |
| Age <=55 | 4.03 | 1.38-11.81 | 0.011 |
| Age >55 | 2.34 | 0.81-6.74 | 0.12 |
| post-menopausal | 2.06 | 0.83-5.09 | 0.12 |
| pre-menopausal | 6.01 | 1.55-23.25 | 0.0094 |
| Grade 1 & 2 | 3.57 | 1.52-8.35 | 0.0034 |
| Grade 3 | 2.35 | 0.29-18.77 | 0.42 |
| PgR + | 3.48 | 1.35-9.0 | 0.0099 |
| PgR − | 2.06 | 0.57-7.49 | 0.27 |

TABLE 29

Diagnostic values of MS to predict distant metastasis in 5 years for Japanese samples

| | Cut 1 (int + low combined) |
|---|---|
| Sensitivity | 0.81 (0.60-0.92) |
| Specificity | 0.65 (0.58-0.71) |
| PPV | 0.19 (0.15-0.24) |
| NPV | 0.97 (0.93-0.99) |

TABLE 30

Progesterone receptor (PR) transcripts (PGR is the gene name for PR), including four exemplary variants.

| Gene Symbol | GenBank Accession Number | Exemplary Forward Primer Sequence (5'→3') | Exemplary Reverse Primer Sequence (5'→3') | Exemplary Probe Sequence (5'→3) |
|---|---|---|---|---|
| PGR* | NM_000926 (SEQ ID NO: 35) | TCGAGTCA TTACCTCAG AAGAT (SEQ ID NO: 39) | CCCACAGG TAAGGACA CCATA (SEQ ID NO: 40) | TGACAGCC TGATGCT TCAT (SEQ ID NO: 41) |
| PGR* | AB085683 (SEQ ID NO: 36) | | | |
| PGR* | AB085844 (SEQ ID NO: 37) | | | |
| PGR* | AB085845 (SEQ ID NO: 38) | | | |

*PGR has at least four alternative splice variants, including GenBank accession numbers NM_000926 (SEQ ID NO: 35), AB085683 (SEQ ID NO: 36), AB085844 (SEQ ID NO: 37), and AB085845 (SEQ ID NO: 38). Primers for amplifying PGR can optionally be designed to amplify a region shared by all listed splice variants, such as the exemplary RT-PCR primers provided in the first row of Table 30 above (which can be used to reverse transcribe and amplify all four alternative splice variants provided in Table 30). Probes can also optionally be designed to hybridize to a region shared by all listed splice variants, such as the exemplary probe sequence provided in the first row of Table 30 above (which can be used to detect all four alternative splice variants provided in Table 30).

TABLE 31

Composite metastasis score (cMS): univariate and multivariate Cox proportional analyses of distant-metastasis-free survival (DMFS) using continuous cMS for the validation dataset

| | Univariate analysis | | Multivariate analysis | |
|---|---|---|---|---|
| Variable | Hazard ratio (95% CI) | p-value | Hazard ratio (95% CI) | p-value |
| cMS (per 10 units) | 2.77 (1.69-4.53) | <0.0001 | 3.18 (1.67-6.06) | 0.0005 |
| Age (10 year scale) | 1.65 (1.09-2.49) | 0.018 | 1.31 (0.81-2.10) | 0.268 |
| Tumor size (cm) | 1.52 (1.00-2.34) | 0.053 | 1.63 (0.94-2.81) | 0.080 |
| Grade 2 | 1.90 (0.76-4.76) | 0.171 | 1.71 (0.52-5.69) | 0.380 |
| Grade 3 | 0.86 (0.25-2.96) | 0.815 | 0.56 (0.11-2.86) | 0.483 |

In univariate analysis, the hazard ratio (HR) per 10 unit increase was 2.77 (95% CI: 1.69-4.53, p<0.0001) for DMFS. After adjustment for age, tumor size and tumor grade in Cox multivariate analysis, the HR per 10 unit increase was 3.18 (95% CI: 1.67-6.06, p=0.0005)

TABLE 32

Composite metastasis score (cMS): Kaplan-Meier estimates of DMFS using the cMS in the ACC & Guy's validation dataset for the high-risk group (cMS cutpoint at 1.738 = high-risk group) (equal to a cutpoint at 17.38 using a cMS rescaled to a 0-40 scale)

Kaplan - Meier Estimates
Stratum 1: cMS cutpoint at 1.738 = high-risk group

| Years | YEARS_DM | Survival | Failure | Survival Standard Error | L95% | U95% | # Failed | # Left |
|---|---|---|---|---|---|---|---|---|
| 0  | 0       | 1      | 0      | 0      | .      | .      | 0  | 91 |
| 2  | 1.7769  | 0.9667 | 0.0333 | 0.0189 | 0.9297 | 1.0000 | 3  | 86 |
| 4  | 3.8412  | 0.8743 | 0.1257 | 0.0355 | 0.8047 | 0.9439 | 11 | 75 |
| 6  | 5.7851  | 0.8495 | 0.1505 | 0.0386 | 0.7738 | 0.9252 | 13 | 63 |
| 8  | 7.6304  | 0.8192 | 0.1808 | 0.0428 | 0.7353 | 0.9031 | 15 | 46 |
| 9  | 7.6304  | 0.8192 | 0.1808 | 0.0428 | 0.7353 | 0.9031 | 15 | 38 |
| 10 | 9.0021  | 0.7976 | 0.2024 | 0.0468 | 0.7059 | 0.8893 | 16 | 23 |
| 12 | 11.4689 | 0.6647 | 0.3353 | 0.1275 | 0.4148 | 0.9146 | 17 | 3  |
| 14 | 11.4689 | 0.6647 | 0.3353 | 0.1275 | 0.4148 | 0.9146 | 17 | 1  |
| 16 | 11.4689 | .      | .      | .      | .      | .      | 17 | 0  |
| 18 | 11.4689 | .      | .      | .      | .      | .      | 17 | 0  |

TABLE 33

Composite metastasis score (cMS): Kaplan-Meier estimates of DMFS using the cMS in the ACC & Guy's validation dataset for the low-risk group (cMS cutpoint at 1.738 = low-risk group) (equal to a cutpoint at 17.38 using a cMS rescaled to a 0-40 scale)

Kaplan-Meier Estimates
Stratum 2: cMS cutpoint at 1.738 = low-risk group

| Years | YEARS_DM | Survival | Failure | Survival Standard Error | L95% | U95% | # Failed | # Left |
|---|---|---|---|---|---|---|---|---|
| 0  | 0      | 1      | 0      | 0      | .      | .      | 0 | 109 |
| 2  | 0      | 1      | 0      | 0      | .      | .      | 0 | 106 |
| 4  | 0      | 1      | 0      | 0      | .      | .      | 0 | 104 |
| 6  | 4.3915 | 0.9904 | 0.0096 | 0.0096 | 0.9716 | .      | 1 | 96  |
| 8  | 7.7344 | 0.9785 | 0.0215 | 0.0152 | 0.9487 | .      | 2 | 73  |
| 9  | 7.7344 | 0.9785 | 0.0215 | 0.0152 | 0.9487 | .      | 2 | 58  |
| 10 | 9.5715 | 0.9581 | 0.0419 | 0.0250 | 0.9091 | .      | 3 | 36  |
| 12 | 9.5715 | 0.9581 | 0.0419 | 0.0250 | 0.9091 | .      | 3 | 15  |
| 14 | 9.5715 | 0.9581 | 0.0419 | 0.0250 | 0.9091 | .      | 3 | 4   |
| 16 | 9.5715 | 0.9581 | 0.0419 | 0.0250 | 0.9091 | .      | 3 | 2   |
| 18 | 9.5715 | .      | .      | .      | .      | .      | 3 | 0   |

TABLE 34

Composite metastasis score (cMS): Cox PH estimate of DMFS using the cMS in the ACC & Guy's validation dataset with a cMS cutpoint at 1.738 (equal to a cutpoint at 17.38 using a cMS rescaled to a 0-40 scale)
Cox PH Estimate [cMS cutpoint at 1.738 (= cMS_40 cutpoint at 17.38)]

|  | HR | L95% | U95% | p |
|---|---|---|---|---|
| cMS_cut_1.738 | 8.303 | 2.422 | 28.469 | 0.0008 |

Tables 35A-35B. 95% confidence intervals for exemplary MS and PR weighted coefficients (based on the ACC and Guys training dataset, such as described in the "Formulation of the Composite Metastasis Score" section of Example Six, using a Cox model for distant metastasis)

TABLE 35A

| Variable | est | L95% | U95% |
|---|---|---|---|
| MS | 0.0338 | 0.0009 | 0.0667 |
| PR | −0.2203 | −0.3908 | −0.0497 |

TABLE 35B

| Variable | est | std.err | L95% | U95% | Chi.sq | p | HR | HR_L95% | HR_U95% |
|---|---|---|---|---|---|---|---|---|---|
| MS | 0.0338 | 0.0168 | 0.0009 | 0.0667 | 4.0604 | 0.0439 | 1.034 | 1.001 | 1.069 |
| PR | −0.2203 | 0.0870 | −0.3908 | −0.0497 | 6.4078 | 0.0114 | 0.802 | 0.677 | 0.951 |

(MS plus the three housekeeping genes NUP214, PPIG and SLU7)

TABLE 36

95% confidence intervals for exemplary MS and PR weighted coefficients corresponding to Example Seven (based on using TaqMan ® assays for detecting gene expression)

| Variable | Estimate | L95 | U95 |
|---|---|---|---|
| MS | 0.0326 | 0.0006 | 0.0649 |
| PR | −0.2034 | −0.3614 | −0.0469 |

TABLE 37

Exemplary primers and probes for gene expression profiling.

| Pool | Gene | Amp Size | Upper primer | Lower primer | Probe |
|---|---|---|---|---|---|
| 1 | MYBL2 | 59 | GCGGAGCCCCATCAA (SEQ ID NO: 13) | CATCCTCATCCACAAT GTCAA (SEQ ID NO: 14) | 6FAM-TCCGGAAGTCTCTG-MGBNFQ (SEQ ID NO: 66) |
|  | PKMYT1 | 63 | CCTGCCCCCTGAGTTCA (SEQ ID NO: 42) | AGCATCATGACAAGG ACAGAA (SEQ ID NO: 18) | VIC-TCT GTC TTC CGA GCT G-MGBNFQ (SEQ ID NO: 67) |
|  | TK1 | 59 | GATGGTTTCCACAGGAA CAA (SEQ ID NO: 25) | CAGCAAGGTTGGTGCCA (SEQ ID NO: 43) | NED-ATC TTG GTG AAA GAT GC-MGBNFQ (SEQ ID NO: 68) |
| 2 | MELK | 64 | AGAGACGGGCCCAGAA (SEQ ID NO: 11) | CTGGATTCACTAATCTAG TTGTAGTCA (SEQ ID NO: 44) | 6FAM-TTA TAG TGA AGC TTT AGT C-MGBNFQ (SEQ ID NO: 69) |
|  | RACGAP1 | 60 | GAAAAGCTGGAACGAC AGA (SEQ ID NO: 45) | GCCAGATGTGTCACACA TGA (SEQ ID NO: 46) | VIC-AGCTGATTCGAGAGATG-MGBNFQ (SEQ ID NO: 70) |
|  | CCNB1 | 63 | GCCAAATACCTGATGGA ACTAA (SEQ ID NO: 3) | TTGAGAAGGAGGAAAGT GCA (SEQ ID NO: 47) | NED-CTATGTTGGACTATGACATG-MGBNFQ (SEQ ID NO: 71) |
|  | UBE2S | 61 | CCTAACCCCGAGTCTGCA (SEQ ID NO: 48) | CCTCGTAGTTCTCCAAG AGCA (SEQ ID NO: 49) | Quasar 670- CTC AAC GAG GAG GCG GGC C-BHQ-2 (SEQ ID NO: 72) |
| 3 | ORC6L | 69 | CACTTCTGCTGCACTGC TTT (SEQ ID NO: 15) | GCTACCATTTTGTTTTTAT CCACTT (SEQ ID NO: 50) | 6FAM-TCAGCTTTAGAATCTTGCAT-MGBNFQ (SEQ ID NO: 73) |
|  | PRR11 | 62 | TGTCCAAGCTGTGGTC AAA (SEQ ID NO: 19) | ACGCAGGCAGGCACA (SEQ ID NO: 51) | VIC-AGT TTA CCA CTC ATG TGA CAT G-MGBNFQ (SEQ ID NO: 74) |
|  | RFC4 | 65 | AGAACTCTTTGGGCCT GAA (SEQ ID NO: 52) | CACGTTCATCAGATGC ATTTAA (SEQ ID NO: 24) | NED-TTCCGATTAAGAGTTCTT-MGBNFQ (SEQ ID NO: 75) |
|  | CENPA | 63 | CAGTCGGCGGAGACAA (SEQ ID NO: 5) | AAGAGGTGTGTGCTCTT CTGAA (SEQ ID NO: 6) | Quasar 670-GCTTTCGGATCTCCTTT AGCCAACC-BHQ-2 (SEQ ID NO: 76) |
| 4 | BUB1 | 57 | TGGTGCCTTCAAGGGAT (SEQ ID NO: 53) | CCTGTTTTGGGCTTTTC TCT (SEQ ID NO: 54) | 6FAM-ATTCAGTCCAATTCAAG-MGBNFQ (SEQ ID NO: 77) |
|  | DIAPH3 | 64 | TTATCCCATCGCCTTGAA (SEQ ID NO: 9) | CCATGTTGTAAACATCA TATGCT (SEQ ID NO: 55) | VIC-ATATTAGAGCTGAACTTGAT-MGBNFQ (SEQ IDNO: 78) |
|  | DC13 | 76 | GTGAGAGATTGAACCAT GGAG (SEQ ID NO: 56) | CGCCCTGCCCAACAA (SEQ ID NO: 8) | NED-ATACTCAGAATCCAGGGTT-MGBNFQ (SEQ ID NO: 79) |
| 5 | ESR1 | 63 | TCTGCAGGGAGAGGAG TTT (SEQ ID NO: 57) | GTGTACACTCCAGAATT AAGCAAAATAA (SEQ ID NO: 58) | FAM-TGTGCCTCAAATCTA-MGB (SEQ ID NO: 80) |
|  | PGR | 61 | CGGGCACTGAGTGTTG AAT (SEQ ID NO: 59) | TGGGTAATTGTGCAGCAATA (SEQ ID NO: 60) | VIC-CTTCAGACATCATTTCTGGA-MGBNFQ (SEQ ID NO: 81) |
|  | ERBB2 | 75 | GCTTTGTGGTCATCCA GAA (SEQ ID NO: 61) | CCAGCAGTGAGCGGTAGAA (SEQ ID NO: 62) | Quasar 670-CCAGCCAGTCCCTTGGA CAGCACC-BHQ-2 (SEQ ID NO: 82) |
|  | NUP214 | 67 | CACTGGATCCCAAGAG TGAA (SEQ ID NO: 29) | GCAAATTTCACATACTGATGAA (SEQ ID NO: 63) | NED-AAT TTC CTG AAG CTG AGC-MGBNFQ (M1 probe) (SEQ ID NO: 83) |
|  | PPIG | 59 | TGGACAAGTAATCTCTG GTCAA (SEQ ID NO: 31) | CATCTGTTTTCTGGTTTTCAA (SEQ ID NO: 64) | NED-TCTCTCTTACAACTTC-MGBNFQ (SEQ ID NO: 84) |
|  | SLU7 | 64 | TGCCAATGCAGGAAAGAA (SEQ ID NO: 33) | TGTGTACCTAACAAAGTTATC TCCA (SEQ ID NO: 65) | NED-CAG ATG AAG TGA GTT ATG-MGBNFQ (SEQ ID NO: 85) |

Each probe is presented above in Table 37 with an exemplary reporter dye (6FAM/FAM, VIC, NED, or Quasar 670) preceding each probe sequence and an exemplary quencher dye (MGB-NFQ, BHQ-2, or MGB) following each probe sequence.

Each pool, as indicated in the first column of Table 37, represents an exemplary grouping for multiplex assays. For example, detection of the expression of the genes indicated in each pool can be carried out by combining the primers and probes corresponding to each gene in a single reaction vessel (e.g., tube). Thus, in exemplary embodiments, gene expression detection of all 20 genes listed in Table 37 can be carried out in five reaction vessels (tubes), as indicated in Table 37 by the five exemplary pools (in certain further embodiments, PGR is not included in pool 5 but is included in another pool or is detected by itself in a singleplex assay).

The invention claimed is:

1. A method for determining risk of tumor metastasis in a human having breast cancer, comprising:
   (a) detecting the expression levels of 14 genes comprising CENPA, PKMYT1, MELK, MYBL2, BUB1, RACGAP1, TK1, UBE2S, DC13, RFC4, PRR11, DIAPH3, ORC6L and CCNB1 in a breast tumor sample from said human, and determining a metastasis score ($MS_u$) based on the expression levels of said 14 genes;
   (b) detecting the expression level of progesterone receptor (PR) in said breast tumor sample; and
   (c) determining a composite metastasis score ($cMS_u$) that indicates risk of tumor metastasis, wherein said $cMS_u$ is calculated from said $MS_u$ and said expression level of PR as follows:

$$cMS_u = \beta_{MS} * MS_u + \beta_{PR} * PR$$

wherein $\beta_{MS}$ is a value between 0.0006 and 0.0667, and wherein $\beta_{PR}$ is a value between −0.3614 and −0.0497.

2. The method of claim 1, wherein $\beta_{MS}$ is a value between 0.0006 and 0.0649 or a value between 0.0009 and 0.0667, and wherein $\beta_{PR}$ is a value between −0.3614 and −0.0469 or a value between −0.3908 and −0.0497.

3. The method of claim 1, wherein $\beta_{MS}$ is 0.326 or 0.0338, and wherein $\beta_{PR}$ is −0.2034, −0.2203, or −0.22026.

4. The method of claim 1, wherein $\beta_{MS}$ is 0.03, 0.04, 0.032, 0.033, or 0.034, and wherein $\beta_{PR}$ is −0.2, −0.22, −0.203, −0.204, −0.2202, or −0.2203.

5. The method of claim 3, wherein $\beta_{MS}$ is 0.326, $\beta_R$ is −0.2034, and said detecting comprises using a real-time PCR (RT-PCR) assay, or wherein $\beta_{MS}$ is 0.0338, $\beta_{PR}$ is −0.2203 or −0.22026, and said detecting comprises using an intercalating dye assay.

6. The method of claim 1, further comprising comparing said $cMS_u$ to at least one predefined composite metastasis score threshold cutoff value ($cMS_u$ threshold), wherein said human is determined to have an increased risk of tumor metastasis if their $cMS_u$ is higher than said $cMS_u$ threshold, or wherein said human is determined to have a decreased risk of tumor metastasis if their $cMS_u$ is lower than said $cMS_u$ threshold.

7. The method of claim 6, wherein said $cMS_u$ threshold is 1.738 or 1.74.

8. The method of claim 1, further comprising re-scaling said $cMS_u$ to thereby obtain a re-scaled cMS.

9. The method of claim 8, further comprising comparing said re-scaled cMS to at least one predefined composite metastasis score threshold cutoff value (cMS threshold), wherein said human is determined to have an increased risk of tumor metastasis if their re-scaled cMS is higher than said cMS threshold, or wherein said human is determined to have a decreased risk of tumor metastasis if their re-scaled cMS is lower than said cMS threshold.

10. The method of claim 8, wherein said re-scaled cMS is obtained by re-scaling said $cMS_u$ to a 0-40 scale by applying either of the following calculations to said $cMS_u$:

$$cMS = (cMS_u + 3.1175) * 10; \text{ or}$$

$$cMS = (cMS_u + 3.28) * 10;$$

wherein cMS=0 if cMS<0, and cMS=40 if cMS>40.

11. The method of claim 10, wherein $\beta_{MS}$=0.326 and $\beta_{PR}$=−0.2034 is used in conjunction with equation cMS=$(cMS_u + 3.1175) * 10$, so that cMS=$0.326 * MS_u - 2.034 * PR + 31.175$; or wherein $\beta_{MS}$=0.0338 and $\beta_{PR}$=−0.22026 is used in conjunction with equation cMS=$(cMS_u + 3.28) * 10$, so that cMS=$0.338 * MS_u - 2.2026 * PR + 32.8$.

12. The method of claim 10, further comprising comparing said re-scaled cMS to a predefined composite metastasis score threshold cutoff value (cMS threshold) of 17.38 or 17.4, wherein said human is determined to have an increased risk of tumor metastasis if their re-scaled cMS is higher than said cMS threshold of 17.38 or 17.4, or wherein said human is determined to have a decreased risk of tumor metastasis if their re-scaled cMS is lower than said cMS threshold of 17.38 or 17.4.

13. The method of claim 1, wherein said expression level is a $\Delta(\Delta Ct)$ value that is calculated as follows for each of said 14 genes:

$$\Delta(\Delta Ct) = (Ct_{GOI} - Ct_{EC})_{test\ RNA} - (Ct_{GOI} - Ct_{EC})_{ref\ RNA}$$

and is calculated as follows for said PR:

$$\Delta(\Delta Ct) = (-1) \times (Ct_{GOI} - Ct_{EC})_{test\ RNA} - (Ct_{GOI} - Ct_{EC})_{ref\ RNA}$$

wherein Ct is the PCR threshold cycle of exponential target amplification, GOI=gene of interest, EC=endogenous control, test RNA=patient sample RNA, and ref RNA=reference RNA.

14. The method of claim 13, wherein said metastasis score ($MS_u$) is calculated by the following:

$$MS_u = -\left[\sum_{i=1}^{14} Gi\right]$$

wherein Gi is equal to said Δ(ΔCt) value for each gene (i) of said 14 genes and represents the expression level of each gene (i).

15. The method of claim 1, wherein the expression levels of said 14 genes and said PR are normalized against the expression level of at least one control gene, or an average of two or more control genes.

16. The method of claim 15, wherein said control gene comprises any one, any two, or all three housekeeping genes selected from the group consisting of NUP214, PPIG, and SLU7.

17. The method of claim 1, wherein said breast tumor sample is estrogen receptor (ER)-positive.

18. The method of claim 1, wherein said human has been treated with tamoxifen.

19. The method of claim 1, wherein said human has early stage (stage I or II) breast cancer or node-negative breast cancer.

20. The method of claim 1, wherein said breast tumor sample is obtained from formalin-fixed paraffin-embedded (FFPE) tumor tissue sections, from a tumor biopsy, or from frozen tumor tissues.

21. The method of claim 1, wherein said detecting comprises reverse transcribing mRNA of said 14 genes and said PR to cDNA, and amplifying said cDNA by polymerase chain reaction (PCR).

22. The method of claim 21, further comprising enriching said mRNA prior to said reverse transcribing and amplifying.

23. The method of claim 1, wherein mRNA of said 14 genes and said PR is reverse transcribed and amplified by primers for each corresponding gene as provided in any of Tables 3, 30, and 37, and/or is detected by a probe for each corresponding gene as provided in either of Tables 30 and 37.

24. The method of claim 23, wherein said probe is detectably labeled.

25. A method for determining a composite metastasis score ($cMS_u$) that indicates risk of tumor metastasis in a human having breast cancer, the method comprising calculating said $cMS_u$ from a metastasis score ($MS_u$) value and a progesterone receptor (PR) value as follows:

$$cMS_u = \beta_{MS}*MS_u + \beta_{PR}*PR$$

wherein $\beta_{MS}$ is a value between 0.0006 and 0.0667, and wherein $\beta_{PR}$ is a value between −0.3614 and −0.0497, and wherein said $MS_u$ value represents the expression level of 14 genes comprising CENPA, PKMYT1, MELK, MYBL2, BUB1, RACGAP1, TK1, UBE2S, DC13, RFC4, PRR11, DIAPH3, ORC6L and CCNB1 in a breast tumor sample from said human, and said PR value represents the expression level of PR in said breast tumor sample.

26. A test kit for determining risk of breast cancer metastasis, comprising one or more containers enclosed in a package, wherein said one or more containers contain:
a) reagents for detecting the expression levels of 14 genes comprising CENPA, PKMYT1, MELK, MYBL2, BUB1, RACGAP1, TK1, UBE2S, DC13, RFC4, PRR11, DIAPH3, ORC6L, and CCNB1, wherein said reagents comprise primers and/or probes that are optionally detectably labeled;
b) reagents for detecting the expression level of progesterone receptor (PR), wherein said reagents comprise primers and/or probes that are optionally detectably labeled;
c) reagents for detecting the expression level of at least one control gene, wherein said at least one control gene is optionally a housekeeping gene selected from the group consisting of NUP214, PPIG, and SLU7, and wherein said reagents comprise primers and/or probes that are optionally detectably labeled; and
d) one or more components selected from the group consisting of a polymerase or other enzyme, buffer, and dNTPs;
and wherein the following are enclosed in said package:
i) instructions for calculating a composite metastasis score (cMS);
ii) an insert setting forth a predefined composite metastasis score threshold cutoff value (cMS threshold); and
iii) instructions for determining risk of breast cancer metastasis by comparing said cMS to said cMS threshold.

* * * * *